(12) United States Patent
Vescovi et al.

(10) Patent No.: US 11,357,840 B2
(45) Date of Patent: *Jun. 14, 2022

(54) METHODS AND COMPOSITIONS FOR REDUCING GROWTH, MIGRATION AND INVASIVENESS OF BRAIN CANCER STEM CELLS AND IMPROVING SURVIVAL OF PATIENTS WITH BRAIN TUMORS

(71) Applicant: HYPERSTEM SA, Lugano (CH)

(72) Inventors: Angelo Luigi Vescovi, Maroggia (CH); Elena Binda, Bergamo (IT)

(73) Assignee: HYPERSTEM SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,081

(22) Filed: May 13, 2020

(65) Prior Publication Data

US 2020/0345821 A1 Nov. 5, 2020

Related U.S. Application Data

(63) Continuation of application No. 15/533,842, filed as application No. PCT/IB2015/002577 on Dec. 9, 2015, now Pat. No. 10,688,167.

(60) Provisional application No. 62/090,029, filed on Dec. 10, 2014.

(51) Int. Cl.
| | |
|---|---|
| *A61K 39/00* | (2006.01) |
| *A61P 35/00* | (2006.01) |
| *A61K 38/17* | (2006.01) |
| *A61K 38/08* | (2019.01) |
| *C07K 7/06* | (2006.01) |

(52) U.S. Cl.
CPC .......... *A61K 39/0011* (2013.01); *A61K 38/08* (2013.01); *A61K 38/1709* (2013.01); *A61P 35/00* (2018.01); *C07K 7/06* (2013.01)

(58) Field of Classification Search
CPC ................ A61K 39/0011; A61K 38/08; A61K 38/1709; A61K 39/001102; A61K 39/395; A61P 35/00; A61P 1/04; A61P 1/16; A61P 1/18; A61P 11/00; A61P 13/08; A61P 15/00; A61P 17/00; A61P 19/00; A61P 25/00; A61P 43/00; C07K 7/06
See application file for complete search history.

(56) References Cited

U.S. PATENT DOCUMENTS

| | | |
|---|---|---|
| 4,105,027 A | 8/1978 | Lundquist |
| 4,192,309 A | 3/1980 | Poulsen |
| 4,227,522 A | 10/1980 | Cams |
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 6,921,527 B2 | 7/2005 | Platz et al. |
| 9,278,119 B2* | 3/2016 | Andersson ............. A61P 35/00 |
| 10,688,167 B2* | 6/2020 | Vescovi .................... A61P 1/04 |
| 2014/0171356 A1 | 6/2014 | Habib et al. |
| 2014/0206623 A1* | 7/2014 | Andersson ........... C07K 14/475 |
| | | 514/19.5 |

FOREIGN PATENT DOCUMENTS

| | | |
|---|---|---|
| EP | 2446895 | 5/2012 |
| WO | WO-1991/16038 | 10/1991 |
| WO | WO-2001/32708 | 5/2001 |
| WO | WO-2006/130082 | 12/2006 |
| WO | WO-2010/019103 | 2/2010 |
| WO | WO-2011/088127 | 7/2011 |

OTHER PUBLICATIONS

Zhan et al., Oncogene, 36:1461-1473, published online Sep. 2016. (Year: 2016).
Clinical Trial Identifier: NCT02020291, first published Dec. 24, 2013. Retrieved online from: <https://clinicaltrials.gov/ct2/results?cond=&term=NCT02020291>. Retrieved on Apr. 9, 2018.
Yu et al., Cancer Letters, 257:172-181, published Jul. 11, 2007.
Nomizu, M., et al. Structure-activity study of a laminin alpha 1 chain active peptide segment Ile-Lys-Val-Ala-Val (IKVAV). FEBS Lett. May 29, 1995;365(2-3):227-31.
Anido J., et al., TGF-b Receptor Inhibitors Target the CD44high/Id1high Glioma-Initiating Cell population in Human Glioblastoma, Cancer Cell 2010, 18:656-668.
Bartek, J. Jr., et al., Key concepts in glioblastoma therapy, J. Neural Neurosurg Psychiatry, 2012, 83:753-760.
Binda E., et al., The EphA2 Receptor Drives Self-Renewal and Tumorigenicity in Stem-like Tumor-Propagating Cells ram Human Glioblastomas, Cancer Cell 2012, 22(6): 765-780.
Bittner M., et al., Molecular classification of cutaneous malignant melanoma by gene expression profiling Nature, 2000, 106:S36-S40.
Brescia P., Identification of Glioma Stem Cells: What is Already Known and How Far do We Still Need to Go? The Biomarkers Dilemma, J Carcinogene Mutagene 2011, S1.

(Continued)

*Primary Examiner* — Kimberly Ballard
*Assistant Examiner* — Stacey N MacFarlane
(74) *Attorney, Agent, or Firm* — Saliwanchik, Lloyd & Eisenschenk

(57) ABSTRACT

The described invention relates to a pharmaceutical composition comprising a therapeutically effect amount of a therapeutic agent, wherein the therapeutic agent is effective (1) to reduce tumor growth, migration, invasion or a combination and (2) improve subject survival relative to a control. The described invention also relates to a method of treating a subject with a tumor, the method comprising: (1) providing a pharmaceutical composition; and (2) administering the pharmaceutical composition, wherein the composition comprises a therapeutically effective amount of a therapeutic agent which is effective to reduce tumor growth, migration, invasion or a combination. The method may further comprise preparing therapeutic agent and preparing the pharmaceutical composition. The therapeutic agents include but are not limited to Wnt5a derivative peptides or Wnt5a antagonists or Wnt5a blocking antibody. The tumor comprises a population of cancer stem cells.

18 Claims, 23 Drawing Sheets

Specification includes a Sequence Listing.

(56) References Cited

OTHER PUBLICATIONS

C.Hirschmann-Jax, A distinct "side population" of cells with high drug efflux capacity in human tumor cells, Proc Natl Acad Sci 2004, 101 (39): 14228-233.
Camilli, T. C.,Striking the Target in Wnt-y Conditions: Intervening in Wnt Signaling During Cancer Progression, Biochem. 2010, Pharmacol. 80(5): 702-711.
Carpino and Han, The 9-Fluo1-en ylmethoxycarhonyl Amino-Protecting Group, 1972, J. Org. Chem.37:3403-3409.
Carreira-Barbosa F., et al., Prickle 1 regulates cell movements during gastrulation and neuronal migration in zebrafish, Development 2003, 130(17):4037-4046.
Chen, J., A restricted cell population propagates glioblastoma growth after chemotherapy, Nature, 2012, 7412:522-526.
Cho, et al., Targeting Cancer Stem Cells for Treatment of Glioblastoma Multiforme, Cell Transplant 2013, 22(4):731-9.
Cruceru, M.L., et al., Therapy targets in glioblastoma and cancer stem cells: lessons from haematopoietic neoplasms, J. of Cellular & Molecular Medicine, 2013,17(10):1218-1235.
Driessens G., Defining themode of tumourgrowthby clonal analysis, Nature, 2012, 742:527-530.
Endo K, et al, Hum Pathol 2003, 31 (5):558-565.
Fields and Noble, Solid phase peptide synthesis utilizing 9-fluorenylmethoxycarbonyl amino acids, 1990, Int. J. Pept. Protein Res. 35: 161-214.
Galli et al., Isolation and Characterization of Tumorigenic, Stem-like Neural Precursors from Human Glioblastoma, Cancer Research (2004) 64: 7011-7021.
Gilbertson, Nature, Cancer: Resolving the stem-cell debate, 2012, 488(7412): 462-463.
Haas-Kogan, D.A. et al., Epidermal Growth Factor Receptor, Protein Kinase B/Akt, and Glioma Response to Erlotinib, J_ Natl. Cancer Inst. 2005, 97, 880-887.
Habu, M., et al., Ryk is essential for Wnt-5a-dependent invasiveness in human glioma, J. Biochem, 2014, 1S6(1):29-38.
Hall et al., Stem cells: the generation and maintenance of cellular diversity, Development 106: 619-33, 1989.
Huelsken et al., b-Catenin Controls Hair Follicle Morphogenesis and Stem Cell Differentiation in the SkinCell, 105: 533-45, 2001.
Inagawa S., et al., Expression and Prognostic Roles of b-Catenin in Hepatocellular Carcinoma: Correlation with Tumor Progression and Postoperative Survival, Clin Cancer Res 2002, 8(2):450-456.
International Search Report and Written Opinion for Application No. PCT/IB2015/002577 dated May 2, 2016.
Jenei, V. et al., A t-butyloxycarbonyl-modified Wnt5a-derived hexapeptide functions as a potent antagonist of Wnt5a-dependent melanoma cell invasion, PNAS, 2009,106(46):19473-9478.
Kamino, M., et al., Wnt-5a signaling is correlated with infiltrative activity in human glioma by inducing cellular migration and MMP-2, Cancer Sci, 2011, 102(3):540-548.
Kandel E.R., et al., Principles of Neural Science, 4th Ed. McGrawHill New York (2000), Ch. 2, pp. 20-21.
Katoh, M. et al., Oncol Rep., 2005 14(6):1583-1588.
Kikuchi A., et al., Tumor formation due to abnormalities in the b-catenin-independent pathway of Wnt signaling, Cancer Sci 2008, 99(2):202-208.
Lee, S. E., et al., Prognostic Significance of Ror2 and Wnt5a Expression in Medulloblastoma, Brain Pathology, 2013, 13:445-453.
Louis D.N., et al., The 2007 WHO ClassiWcation of Tumours of the Central Nervous System, Acta Neuropathol, 2007, 114(2):97-109.
Marion G. Macey, Flow cytometry: principles and applications, Humana Press, 2007.
McNamara. M.G. et al., Emerging Biomarkers in Glioblastoma, Cancers, 2013, 5:1103-1119.
Merrifield, Solid Phase Peptide Synthesis. I. The Synthesis of a Tetrapeptide, 1963, J. Am. Chem. Soc. 85:2149-2154.
Miller J.R., et al., Mechanism and function of signal transduction by the Wnl/b-catenin and Wnl/Ca2+ pathways, Oncogene 1999, 18(55):7860-72.

Miyagi C., et al., STAT3 noncell-autonomously controls planar cell polarity during zebrafish convergence and extension, J Cell Bioi 2004,166(7):975-981.
Morrison et al., The Biology of Hematopoietic Stem Cells, Annu Rev Cell Dev Bioi 11: 35-71, 1995.
Nakada, M. et al., Aberrant Signaling Pathways in Glioma, Cancers, 2011, 3:3242-3278.
P.J. Houghton et al. Antitumor Activity of Temozolomide Combined with Irinotecan Is Partly Independent of O6-Methylguanine-DNA Methyltransferase and Mismatch Repair Phenotypes in Xenograft Models1, Clin. Cancer Res. (2000) 6:4110-4118.
Polakis P., The many ways of Wnt in cancer, Curr Opin Genet Dev 2007:17(1):45-51).
Potten et al., Stem cells: attributes, cycles, spirals, pitfalls and uncertainties Lessons for and from the Crypt, Development 110: 1001-20, 1990.
Qian D., et al., Wnt5a functions in planar cell polarity regulation in mice Dev Bioi 2007, 306(1):121-133).
Ramnarain,D.B.; Differential Gene Expression Analysis Reveals Generation of an Autocrine Loop by a Mutant Epidermal Growth Factor Receptor in Glioma Cells, Cancer Res. 2006,66, 867-874.
Reardon, D.A., et al., Multicentre phase II studies evaluating imatinib plus hydroxyurea in patients with progressive glioblastoma Br. J. Cancer 2009, 101, 1995-2004.
Reardon, D.A., et al., Phase II Study of Imatinib Mesylate Plus Hydroxyurea in Adults With Recurrent Glioblastoma Multiforme, J. Clin. Oncol. 2005, 23, 9359-9368.
Reynolds and Weiss, Generation of Neurons and Astrocytes from Isolated Cells of the Adult Mammalian Central Nervous System, Science 255:1707-10, 1992.
Rich, J.N., et al., EGFR Mutations and Sensitivity to Gefitinib, N. Engl. J. Med. 2004, 351, 1260-1261.
Richards et al., De novo generation of neuronal cells from the adult mouse brain, Proc Natl Acad Sci USA 89: 8591-5, 1992.
Serrano, M., et al., A new regulatory motif in cell-cycle control causing specific inhibition of cyclin D/CDK4, Nature, 1993,366:704-707.
Siar C.H., Differential expression of canonical and non-canonical Wnt ligands in ameloblastoma, J Oral Pathol. Med., 2012, 41 (4):332-339).
Singh et al., Identification of human brain tumour initiating cells, Nature (2004) 532:396-401.
Singh S.K., et al., Identification of a Cancer Stem Cell in Human Brain Tumors, Cancer Res 2003, 63:5821-5828.
Suzuki H., et al., A genomic screen for genes upregulated by demethylation and histone deacetylase inhibition in human colorectal cancer, 2002, 31(2):141-9.
Takeuchi M., et al., The prickle-Related Gene in Vertebrates Is Essential for Gastrulation Cell Movements, Curr Bioi 2003:, 13(8):674-679.
Tapash K. Ghosh et al. eds., 1997, Transdermaland Topical Drug Delivery Systems, pp. 249-297.
TCGA Research Network, Comprehensive genomic characterization defines human glioblastoma genes and core pathways, Nature, 2008, 455:1061-1068.
U.S. Appl. No. 08/423,568, filed Apr. 14, 1995.
Van Den Bent, M.J. et al., Randomized Phase II Trial of Erlotinib Versus Temozolomide or Carmustine in Recurrent Glioblastoma: EORTC Brain Tumor Group Study 26034, J. Clin. Oncol. 2009, 27, 1268-1274.
Veeman M.T., et al., Zebrafish Prickle, a Modulator of Noncanonical Wnt/Fz Signaling, Regulates Gastrulation Movements, Curr Biol 2003, 13(8):680-685.
Verhaak, R.G., et al., Integrated Genomic Analysis Identifies Clinically Relevant Subtypes of Glioblastoma characterized by Abnormalities in PDGFRA, IDH1, EGFR, and NF1, Cancer Cell, 2010, 17(1):98-110.
Wang C.M., et al., b-Catenin Mutation and Overexpression in Hepatocellular Carcinoma Clinicopathologic and Prognostic Significance, Cancer 2001, 92(1):136-145.
Wang Y., Wnt/Planar cell polarity signaling: A new paradigm for cancer therapy, Mol Cancer Ther, 2009; 8 (8):2103-2109.

(56) References Cited

OTHER PUBLICATIONS

Weeraratna A.T. et al., Wnt5a signaling directly affects cell motility and invasion of metastatic melanoma, Cancer Cell, 2002, 1(3): 279-288.
Weissman, Stem Cells: Units of Development, Units of Regeneration, and Units in Evolution, Cell 100: 157-68, 2000.
Weissman, Translating Stem and Progenitor Cell Biology to the Clinic: Barriers and Opportunities, Science 287: 1442-6, 2000.
Wu, W., et al., Mutual antagonism between dickkopf1 and dickkopf2 regulates Wnl/?-catenin signalling, Curr Bioi 2000, 10(24):611-1614.
Yu, J.M., et al., Role of Wnt5a in the proliferation of human glioblastoma cells, Cancer Lett., 2007, 257(2): 172-181.
Safholma., et al., "The Wnt-5a—derived hexapeptide foxy-5 inhibits breast cancer metatastass in vivo by targeting cell motility", Clin. Cancer Res., 2008, vol. 14, pp. 6556-6563.
Binda, E. et al. "Wnt5a Drives an Invasive Phenotype in Human Glioblastoma Stem-like Cells" *Cancer Res*, 2016, 77(4):996-1007.

\* cited by examiner

```
SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Met Asp Gly Cys Glu Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Leu Glu Cys Gly Asp Met
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Leu Glu Gly Asp Met
1               5
```

METHODS AND COMPOSITIONS FOR REDUCING GROWTH, MIGRATION AND INVASIVENESS OF BRAIN CANCER STEM CELLS AND IMPROVING SURVIVAL OF PATIENTS WITH BRAIN TUMORS

CROSS REFERENCE TO RELATED APPLICATIONS

The present application is a continuation of U.S. application Ser. No. 15/533,842, filed Jun. 7, 2017, which is a National Stage application filed under 35 U.S.C. § 371 of International Application No. PCT/IB2015/002577, filed on Dec. 9, 2015, which claims the benefit of priority to U.S. Provisional Ser. No. 62/090,029 filed Dec. 10, 2014, entitled "METHODS AND COMPOSITIONS FOR REDUCING GROWTH, MIGRATION AND INVASIVENESS OF BRAIN CANCER STEM CELLS AND IMPROVING SURVIVAL OF PATIENTS WITH BRAIN TUMORS", the content of which is incorporated by reference herein in its entirety.

FIELD OF THE INVENTION

The described invention relates to methods and compositions for reducing tumor growth, migration, invasion or a combination thereof and improving subject survival relative to a control.

BACKGROUND OF THE INVENTION

Malignant Tumor/Cancer

Cancer is a disease involving abnormal cell growth in terms of cell number (proliferation) or in cell size with the potential to invade or spread to other parts of the body (metastasis). Cancer cell proliferation is well known but the mechanism(s) driving metastasis is (are) not well known. Cancer is a disease of genomic alterations: DNA sequence changes, copy number aberrations, chromosomal rearrangements and modification in DNA methylation together drive the development and progression of human malignancies. (The Cancer Genome Atlas Network (TCGA), Nature 2008, 455(23): 1061-68.)

Glioma

A glioma is a type of tumor, which arises from glial cells in the brain or spine. The most common site of gliomas is the brain. Gliomas make up about 30% of all brain and central nervous system tumors and 80% of all malignant brain tumors.

Glial cells, the most abundant cell type in the central nervous system, are supportive cells that surround neurons and provide support for and insulation between them. Unlike neurons, glial cells do not conduct electrical impulses. There are two major classes of glial cells in the central nervous system: astrocytes and oligodendrocytes (Kandel E R, et al., Principles of Neural Science, 4$^{th}$ Ed. McGraw-Hill New York (2000), Ch. 2, pp. 20-21).

Gliomas are named according to the specific type of cell with which they share histological features, but not necessarily from which they originate. The main types of gliomas are: astrocytomas—which share histological features with astrocytes (e.g., glioblastoma multiforme is a malignant astrocytoma and the most common primary brain tumor among adults); oligodendrogliomas—which share histological features with oligodendrocytes; brainstem glioma—a glioma that develops in the brain stem; optic nerve glioma—a glioma that develops in or around the optic nerve; and mixed gliomas, such as oligoastrocytomas, that contain cells that share histological features with oligodendrocytes and astrocytes.

Gliomas are further categorized according to their grade, which is determined by pathologic evaluation of the tumor. Of numerous grading systems in use, the most common is the World Health Organization (WHO) grading system for Glioma, under which tumors are graded from I to IV (Louis D N, et al., Acta Neuropathol, 2007, 114(2):97-109).

Grade I tumors are slow-growing, nonmalignant, and associated with long-term survival (e.g., pilocytic astrocytoma).

Grade II tumors are relatively slow-growing but sometimes recur as higher grade tumors. They can be nonmalignant or malignant (e.g., diffuse astrocytoma).

Grade III tumors are malignant and often recur as higher grade tumors (e.g., anaplastic astrocytoma).

Grade IV tumors reproduce rapidly and are very aggressive malignant tumors (e.g., glioblastoma, giant cell glioblastoma, and gliosarcoma).

Medulloblastoma is the most common type of primary brain tumor occurring in children. The term "medulloblastoma" refers to a series of tumors found in the cerebellum of children. Originally classified as a glioma, medulloblastoma (WHO grade IV tumor) is referred to now as an embryonal tumor. Thought to arise from the malignant transformation of progenitors of the external granular layer of the cerebellum, this tumor accounts for approximately 7-8% of all intracranial tumors and 30% of pediatric brain tumors, and, opposed to glial tumors, is primarily characterized by neuronal differentiation.

Glioblastoma

Glioblastoma multiforme (GBM), a WHO grade IV malignant glioma, classification name "glioblastoma", is the most common and most aggressive primary brain tumor in adults. GBM arises from glial cells and accounts for 40%-60% of all diffuse astrocytic tumors and 10%-15% of all intracranial neoplastic lesions. The biological characteristics of this tumor are exemplified by prominent proliferation, active invasiveness, and rich angiogenesis. (Nakada, M. et al., Cancers, 2011, 3: 3242-3278). GBM is composed of poorly differentiated neoplastic astrocytes. The presence of microvascular proliferation and/or necrosis is essential for histopathological diagnosis of GBM.

GBM is one of the most aggressive human cancers and is very difficult to treat due to several complicating factors: the tumor cells are very resistant to conventional therapies; the brain is susceptible to damage by conventional therapy; the brain has a very limited capacity to repair itself; and many drugs cannot cross the blood-brain barrier to act on the tumor.

Although treatment can involve radiation, surgery and chemotherapy with temozolomide, which is a methylating agent (P. J. Noughton et al. Clin. Cancer Res. (2000) 6:4110-4118), decades of surgical therapy, radiotherapy, and chemotherapy have failed to drastically change survival for GBM. The medium survival of patients with GBM in clinical trial populations treated with multimodal treatment approaches is approximately 12-15 months, with only 3%-5% of patients surviving longer than 36 months. (McNamara. M. G. et al., Cancers, 2013, 5: 1103-1119).

Based on clinical experience, two subgroups of GBMs have been established, primary glioblastoma and secondary glioblastoma, although these two groups are histologically indistinguishable. Primary glioblastoma, which comprises more than 90% of biopsied or resected cases, arise de novo without antecedent history of low-grade disease, whereas secondary glioblastoma progresses from previously diagnosed low-grade gliomas.

According to a gene-expression-based molecular classification described by The Cancer Genome Atlas (TCGA) Network, Glioblastoma multiforme has four distinct molecular subtypes: Classical, Proneural, Mesenchymal and Neural (TCGA Research Network, Nature, 2008, 455: 1061-1068).

Classical GBM tumors are characterized by abnormal amplification and high levels of epidermal growth factor receptor (EGFR) which is a protein found on the surface of some cells that, when bound by epidermal growth factor, sends signals for the cell to keep growing in number (proliferation). The EGFR abnormalities occur at a much lower rate in the three other GBM subtypes. The TP53 gene codes for tumor protein p53 that normally suppresses tumor growth. TP53 is rarely mutated in classical GBM tumors subtype, but is the most frequently mutated gene in other subtypes of GBM.

Proneural GBM tumors are characterized by alterations of platelet derived growing factor receptor A (PDGFRA) and point mutations in IDH1. The gene IDH1 which encodes isocitrate dehydrogenase-1, when mutated, codes for a protein that can contribute to abnormal cell growth. PDGFRA, which plays an important role in cell proliferation, cell migration, and angiogenesis, was also found to be mutated and expressed in abnormally high amounts. PDGFRA alteration only occurs in Proneural tumors and not in any other subtypes. When PDGFRA is altered, too much of its protein can be produced, leading to uncontrolled tumor growth. The patients of this subtype tend to be younger and to survive longer than in other subtypes.

The Mesenchymal subgroup contains the most frequent number of mutations in the neurofibromatosis type 1 (NF1) tumor suppressor gene. Frequent mutations in the PTEN (phosphatase and tensin homolog) and TP53 tumor suppressor genes also occur in the Mesenchymal subgroup. PTEN protein acts as a tumor suppressor, helping regulate the cycle of cell division.

While the Neural subgroup has mutations in many of the same genes as the other groups, the group does not stand out from the others as having significantly higher or lower rates of mutations. The Neural group is characterized by the expression of several markers that are also typical of the brain's normal, noncancerous nerve cells, or neurons, such as NEFL, GABRA1, SYT1 and SLC12A5.

These molecular subtypes of glioblastoma multliforme appear to differ in their clinical courses and therapeutic responses. For example, the different subtypes show varying responses to aggressive chemotherapy and radiotherapy, with a difference of around 50% between the subtypes. It has been suggested that the pathology of each subtype might begin from different types of cells, which might explain the variation in response to therapy. The greatest benefit was seen in the Classical and Mesenchymal subtypes, where intensive therapy has significantly reduced mortality; and there was a suggestion of efficacy in the Neural subtype; but the Proneural subtype was less responsive to intensive therapy including conventional chemotherapy or chemoradiation therapy. (Verhaak, R G, et al., Cancer Cell, 2010, 17(1):98-110.)

TABLE 1

Summary of Four Subtypes of Glioblastoma according to TOGA classification (Bartek, J. Jr., et al., J. Neurol Neurosurg Psychiatry, 2012, 83:753-760)

| Phillips et al | Pro-neural | | Proliferative | Mesenchymal |
|---|---|---|---|---|
| Verhaak et al | Pro-neural | Neural | Classical | Mesenchymal |
| Signature | Olig2/DLL3/SOX2 | MBP/MAL | EGFR/AKT2 | YKL40/CD44 |
| Mutations | TP53 mutations | | Chrom 7 gain | NFkB |
| | PI3K | | Chrom 10 loss | NF1 |
| | PDGFRA | | PDGRRA | |
| Clinical features | Non-responder to chemotherapy | | Clinical outcome improved with temozolomide/ radiation | Clinical outcome improved with temozolomide/ radiation |

Conversely, a mesenchymal phenotype is the hallmark of tumor aggressiveness in human malignant glioma. Mesenchymal and Classical subclasses exhibit a worse prognosis compared to Proneural tumors, which may be related to the fact that a subset of Proneural tumors displays mutations in the IDH1 gene as well as the glioma-CpG island methylator phenotype (G-CIMP), both favorable prognostic factors (Verhaak, R G, et al., Cancer Cell, 2010, 17(1):98-110).

Aggressive Proliferation, Active Invasiveness, and Angiogenesis of GBM

The aggressive proliferation, active invasiveness, and angiogenesis of GBM are mainly due to highly deregulated signaling pathways in the tumor.

Proliferative activity with histopathologically detectable mitoses is prominent in almost all GBM cases. Two of the most important proliferation signaling cascades frequently deregulated in glioma are the PI3K/Akt/mTOR and Ras/MEK/MAPK pathways which will be discussed later.

Ubiquitous angiogenesis is an outstanding feature of GBMs. The degree of vascularization is significantly correlated with glioma malignancy, tumor aggressiveness, and clinical prognosis. Pro-angiogenic pathways include a sequence of coordinated events that is initiated by expression of angiogenic factors such as vascular endothelial growth factor (VEGF) with subsequent binding to its cognate receptors on endothelial cells.

GBM is highly invasive. Glioma invasion is a complex process involving (1) detachment from the original site; (2) adhesion to the extracellular matrix (ECM); (3) remodeling of the ECM; and (4) cell migration. Migrating glioma cells tend to move along the vessels, dendrites, and fibers in white matter. These characteristics suggest that GBM possesses specific biological mechanisms that mediate its invasive nature. The highly infiltrative nature of human gliomas recapitulates the migratory behavior of glial progenitors during development of the CNS, suggesting that the activators, receptors, and signaling proteins that contribute to neural crest cell migration may be key players in glioma invasion. Accumulating studies have shown that invasion signaling is induced by several kinds of membrane type protein, such as tyrosine kinase receptor (RTK), integrin, CD44, and G protein-coupled receptor (GPCR), as well as intracellular signaling molecules, including PI3K/Akt, and small GTPases, such as Rac1, cdc42, and RhoA. The CD44 antigen is a cell-surface glycoprotein involved in cell-cell interactions, cell adhesion and migration.

EGFR and EphA2 (ephrin type-A receptor 2) RTK are expressed in GBM and are co-localized to the cell surface. EphA2 phosphorylation is dependent on EGFR activity, and EphA2 down-regulation inhibits EGFR phosphorylation, downstream signaling, and EGF-induced cell viability (Ramnarain, D. B.; Cancer Res. 2006, 66, 867-874).

Major Glioma Signaling Pathways

Several major signaling pathways have been associated with Glioma (Nakada, M. et al., Cancers, 2011, 3: 3242-3278).

1. Receptor Tyrosine Kinase Pathway (RTK/PI3K/Akt/mTOR Pathway).

The RTK/PI3K/Akt pathway regulates various fundamental cellular processes such as proliferation, growth, apoptosis, and cytoskeletal rearrangement. The pathway involves receptor tyrosine kinases (RTKs), for example, epidermal growth factor receptor (EGFR), platelet derived growing factor receptor (PDGFR), and vascular endothelial growth factor receptor (VEGFR), etc., as well as tumor suppressor protein phosphatase, for example, phosphatase and tension homolog (PTEN), and protein kinases PI3K, Akt, and mTOR. The Receptor Tyrosine Kinase pathway (RTK/PI3K/Akt/mTOR Pathway) is shown in FIG. 1.

EGFR gene amplification is the most frequent alteration (approximately 40%) in GBM. EGFR is a transmembrane glycoprotein member of the ErbB receptor family. In GBM, EGFR is dysregulated through overexpression, which arises because of EGFR gene amplification or activating mutations such as EGFRvIII that lead to ligand-independent signaling. EGFR aberrations have been correlated with a classical subtype of GBM (TCGA Research Network, Nature 455: 1061-68; Verhaak, Roel G. W. et al., Cancer Cell, 2010, 17: 98-110). Although it has been suggested that alterations of EGFR may be correlated with increased aggressiveness of GBM (Nakada, M. et al., Cancers, 2011, 3: 3242-3278), EGFR inhibitors (e.g., Gefinitib, Erlotinib) have not elicited clinical responses in patients with GBMs in clinical trials (Rich, J. N., et al., N. Engl. J. Med. 2004, 351, 1260-1261; Haas-Kogan, D. A. et al., J. Natl. Cancer Inst. 2005, 97, 880-887; van den Bent, M. J. et al., J. Clin. Oncol. 2009, 27, 1268-1274).

Overexpression of platelet-derived growth factor receptor (PDGFR), especially PDGFR-α, and platelet-derived growth factor (PDGF) have been observed in astrocytic tumors of all grades, and their association with malignant progression has been suggested (Nakada, M. et al., Cancers, 2011, 3: 3242-3278). PDGFRA amplification (14%), as well as IDH1 mutation, are major features of the Proneural subtype of GBM according to the TCGA classification (TCGA Research Network, Nature 455: 1061-68; Verhaak, R. G. et al., Cancer Cell, 2010, 17: 98-110). Despite deep association of this molecule with GBM, anti-PDGFR therapy using Imatinib yielded only limited clinical responses (Reardon, D. A., et al., J. Clin. Oncol. 2005, 23, 9359-9368; Reardon, D. A., et al., Br. J. Cancer 2009, 101, 1995-2004).

The PI3Ks are widely expressed lipid kinases that promote diverse biological functions. The binding of PI3Ks and RTKs results in activation of Akt through phosphatidylinositol 3,4,5-triphosphate (PiP3) and 3-phosphoinositide dependent protein kinase-1 (PDK1), which affects multiple fundamental cellular processes including cell survival, proliferation, and motility. According to the integrated genomic classification of GBM, PI3K mutations (15%) are associated with the Proneural subtype (TCGA Research Network, Nature, 2008, 455: 1061-68; Verhaak, R. G. et al., Cancer Cell, 2010, 17: 98-110).

Decreased PTEN activity can activate the RTKs/PI3K/Akt pathway since PTEN negatively regulates the pathway by antagonizing PI3K function. Homozygous deletion or mutation of PTEN is a common genetic feature in GBM (40%), resulting in constitutive activation of the RTKs/PI3K/Akt pathway. PTEN loss is associated with both classical and mesenchymal subtypes of GBM, according to the TOGA study (TCGA Research Network, Nature 455 (23): 1061-68).

Akt is an STK (Serine/threonine specific protein kinase) that regulates cell growth, proliferation, and apoptosis. Akt activation has been reported in approximately 80% of human GBMs and correlates with the fact that RTKs/PI3K/Akt signaling is altered in 88% of GBM (TCGA Research Network, Nature 455(23): 1061-68). Oncogenic Akt mutations have not been detected in GBM. Akt inhibitor perifosine is undergoing clinical evaluation in malignant gliomas (Nakada, M. et al., Cancers, 2011, 3: 3242-3278).

2. $p14^{ARF}$/MDM2/p53 Pathway.

The p53 gene encodes a protein that responds to diverse cellular stresses to regulate target genes that induce cell cycle arrest, cell death, cell differentiation, senescence, DNA repair, and neovascularization. Following DNA damage, p53 is activated and induces transcription of genes (such as p21Waf1/Cip1) that function as regulators of cell cycle progression at G1 phase. Mouse double minute 2 homolog (MDM2) oncogene inhibits p53 transcriptional activity by forming a tight complex with the p53 gene, and participates in the degradation of p53. The $p14^{ARF}$ gene codes a protein that directly binds to MDM2 and inhibits MDM2-mediated p53 degradation. In turn $p14^{ARF}$ expression is negatively regulated by p53. Thus, inactivation of $p14^{ARF}$/MDM2/p53 is caused by altered expression of any of the p53, MDM2, or p14ARF genes. The p53 pathway plays a crucial role in the development of secondary GBMs. The p53 gene is the most commonly mutated p53 pathway gene in glioma; however, molecular abnormalities involving other genes in the pathway have also been described. (Nakada, M. et al., Cancers, 2011, 3: 3242-3278). The $p14^{ARF}$/MDM2/p53 Pathway is shown in FIG. 2.

3. RB Pathway.

The RB (retinoblastoma tumor suppressor protein) pathway suppresses cell cycle entry and progression, as well as the p53 pathway. The 107-kDa RB1 protein encoded by RB1 (at 13q14) controls progression through G1 into the S-phase of the cell cycle (Serrano, M., et al., Nature, 1993, 366: 704-707). The CDKN2A protein (i.e. $p16^{INKa4}$ which is cyclin-dependent kinase inhibitor 2A) binds to cyclin-dependent kinases 4 (CDK4) and inhibits the CDK4/cyclin D1 complex, thus inhibiting cell cycle transition from G1 to S phase. Thus, alteration of RB1, CDK4, or CDKN2A can cause dysregulation of the G1-S phase transition. However, alteration of only the RB pathway is insufficient to induce tumor formation. EGFR amplification enhances the PI3K pro-growth pathway and is typically associated with CDKN2A deletions. CDKN2A loss is associated with the classical subtype of GBM, according to the TOGA study. (Nakada, M. et al., Cancers, 2011, 3: 3242-3278). The RB pathway is shown in FIG. 2.

4. Ras/MEK/MAPK Pathway.

RAS (Rat sarcoma) proteins act as on/off (RAS-GDP/RAS-GTP) switches controlled by RTKs and neurofibromatosis type 1 tumor suppressor gene (NF-1). Activated RAS (RAS-GTP) then activates serine/threonine kinase RAF. RAF activates mitogen-activated protein kinase kinase (MAPKK), also called MEK, which in turn activates MAPK. MAPK activation results in activation of various transcription factors, such as Elk1, c-myc, Ets, STAT1/3, and PPAR.

The NF-1 tumor suppressor gene encodes neurofibromin, which functions primarily as a RAS negative regulator and plays a role in adenylate cyclase- and Akt-mTOR-mediated pathways. There is increasing evidence that the NF-1 gene is involved in the tumorigenesis of not only NF-1-related, but also sporadically occurring, gliomas. In the TOGA pilot study, NF-1 mutation/homozygous deletions were identified in 18% of GBM. Mesenchymal GBMs, having frequent inactivation of the NF-1 (37%), p53 (32%), and PTEN genes, respond to aggressive chemo-radiation adjuvant therapies. (Nakada, M. et al., Cancers, 2011, 3: 3242-3278). The Ras/MAPK pathway is shown in FIG. 3. A global view of the signaling pathways mentioned above is shown in FIG. 4.

In addition to the signaling pathways mentioned above, other signaling pathways may play a role in GBM initiation, migration, and invasion.

Wnt (Wingless-Related/Mouse Mammary Tumor Virus Integration Family) Signaling Pathways The proteins encoded by the WNT genes play a role in normal embryonic development. The embryonic processes they control include body axis patterning, cell fate specification, cell proliferation, and cell migration. These processes are necessary for proper formation of important tissues including bone, heart, and muscle. Wnt signaling pathways, which are complex, are aberrantly activated across a vast range of malignancies. Wnt proteins also have been implicated in tumorigenesis, and the inappropriate activation of the Wnt pathway results in the onset of several types of cancer, including breast cancer, prostate cancer, glioblastoma, and others. (Camilli, T. C., Biochem. 2010, Pharmacol. 80(5): 702-711; Polakis P., Curr Opin Genet Dev 2007: 17(1):45-51).

The Wnt signaling pathways are a group of signal transduction pathways of proteins that pass signals from outside of a cell through cell surface receptors to the inside of the cell. The variety of receptors and ligands involved in Wnt signaling lead to a multitude of diverse signal transduction cascades.

The Wnt family of proteins consists of 19 known human members (Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16). These secreted lipid-modified signaling glycoproteins are 350-400 amino acids in length, share 20-85% amino acid identity, and have a conserved pattern of 23-24 cysteine residues. The type of lipid modification that occurs on these proteins is palmitoylation of cysteine in the conserved pattern of 23-24 cysteine residues. Palmitoylation initiates targeting of Wnt protein to the plasma membrane for secretion and allows the Wnt protein to bind its receptor due to the covalent attachment of fatty acids. Following their synthesis, secreted Wnt proteins are modified by glycosylation. In Wnt signaling, these secreted proteins act as ligands to activate the different Wnt pathways via paracrine and autocrine routes.

The Wnt signaling pathways are activated by the binding of a Wnt-protein ligand to a Frizzled ("Fz") family receptor, which passes the biological signal to the protein Dishevelled inside the cell. To date, at least ten members of Frizzled family receptors have been identified, all of which are seven-pass transmembrane proteins characterized by an extracellular N-terminal conserved cysteine-rich domain (CRD) that interacts with Wnts. However, to facilitate Wnt signaling, co-receptors may also be required alongside the interaction between the Wnt protein and Fz receptor. Examples include low density lipoprotein receptor-related protein (Lrp5/6), receptor tyrosine kinase (Ryk), and Ror2.

Interaction of Wnts with their receptors and co-receptors is associated with at least three signaling pathways, namely the canonical Wnt/β-catenin pathway, the non-canonical (or heretical) planar cell polarity (PCP) pathway, and the non-canonical (or heretical) Wnt/$Ca^{2+}$ pathway. FIG. 5 shows these three representative Wnt signaling pathways. The Fz receptors have the ability to discriminate between different Wnt ligands, and as such, activation of one of these three pathways is dictated by the nature of the ligand/receptor interaction. (Camilli, T. C., Biochem. 2010, Pharmacol. 80(5): 702-711). The canonical Wnt pathway leads to regulation of gene transcription, the noncanonical planar cell polarity pathway regulates the cytoskeleton that is responsible for the shape of the cell, and the noncanonical Wnt/calcium pathway regulates calcium inside the cell. Wnt signaling pathways use either nearby cell-cell communication (paracrine) or same-cell communication (autocrine).

Canonical Wnt Signaling Pathway

The canonical Wnt signaling pathway is a well-established, β-catenin-dependent signaling pathway which involves a key mediator, β-catenin. In the absence of Wnt signaling, β-catenin is phosphorylated by casein kinase 1 (CK1) and glycogen synthase kinase 3 beta (GSK3β) within a "destruction complex" formed by several proteins, including the scaffolding protein Axin and the tumor suppressor gene product APC (Adenomatous Polyposis coli). Phosphorylated β-catenin is then recognized by the ubiquitination machinery and sent for degradation in the proteasome. When Wnts bind to their receptors Fz and Lrp5/6, Lrp5/6 are phosphorylated and Dishevelled is activated, which leads to inactivation or disassembly of the β-catenin "destruction complex" such that β-catenin phosphorylation is reduced and β-catenin is stabilized. The stabilized β-catenin then translocates to the nucleus where it regulates downstream gene expression by biding to Lef (Lymphoid enhanced transcription factor) and Tcf (T-cell factor), leading to the transcription of Wnt target genes involved in proliferation and tumor progression. Several members of the pathway can be regulated independently of Wnt signaling. For example, GSK-3β can be inhibited by ILK (Integrin Linked Kinase), and is at the intersection of numerous pathways that might regulate its expression. The Canonical Wnt proteins include Wnt1, Wnt2, Wnt3a, Wnt8a, Wnt8b, Wnt10a, Wnt10b (Jiar C H, J Oral Pathol. Med., 2012, 41(4):332-339).

The Canonical Wnt Pathway in Cancer

The stabilization of β-catenin, lack of degradation and ultimately nuclear accumulation has been linked to poorly differentiated morphology (Endo K, et al., Hum Pathol 2003, 31(5):558-565), high proliferative activity (Inagawa S., et al., Clin Cancer Res 2002, 8(2):450-456), and poor prognosis (Wang C M, et al., Cancer 2001, 92(1):136-145). The fate of β-catenin, namely, its accumulation or degradation, is regulated by numerous proteins, which, if not regulated or expressed appropriately, would account for increased β-catenin expression in cancer. This dysregulation may occur due to mutations in the various members of the signaling pathway, or to epigenetic events. Mutations in Wnts themselves are rare. Mutations affecting downstream targets however, are quite frequent in cancer.

The first described, and perhaps best well known role for Wnt/β-catenin signaling is in colon cancer, where nearly 90% of these tumors harbor mutations that result in β-catenin mutation.

Several Wnt therapeutics that target β-catenin pathways have been the subjects of clinical trials in humans.

Non-Canonical Signaling Pathway

The non-canonical signaling pathway is an umbrella term for all Wnt-activated cellular signaling pathways that do not promote β-catenin-mediated transcription, and numerous such pathways have been identified. Unlike the canonical Wnts, non-canonical pathways are unable to transform mammary epithelial cells and are thought to be involved primarily in cell movement and polarity (Veeman M T, et al., Curr Biol 2003, 13(8):680-685; Kikuchi A, et al., Cancer Sci 2008, 99(2):202-208). There are at least two major non-canonical Wnt pathways, the planar cell polarity (PCP) pathway, and the Wnt/Ca2+ pathway. However, because both involve key molecules such as Wnt5A and ROR2, it is quite difficult to discern the Wnt/PCP and Wnt/$Ca^{2+}$ pathways in human cancer.

The Wnt/PCP pathway has been best described in development, where it coordinates the polarization of cells along embryonic axes. This involves the activation of STAT3, and JAK/STAT signaling (Miyagi C, et al., J Cell Biol 2004, 166(7):975-981). Wnts that play a role in Wnt/PCP signling include Wnt5A, Wnt11, and Wnt 7a (Wang Y., Mol Cancer Ther, 2009; 8(8):2103-2109). During Wnt/PCP signaling, Wnt/Fz/Ror2 interactions recruit disheveled (Dsh/Dvl) to the membrane, trigger the recruitment of yang and prickle to the membrane of adjacent cells, and the balance between these regulates polarity. Disheveled-dependent Wnt/PCP signaling then transduces signals via JNK, Jun, Daam, RhoA, Rac, Cdc42 and Profilin, and these have cytoskeletal effects that ultimately control both polarity and motility (Carreira-Barbosa F, et al., Developmetn 2003, 130(17): 4037-4046; Takeuchi M, et al., Curr Biol 2003, 13(8):674-679; Qian D, et al., Dev Biol 2007, 306(1):121-133). Since these features (meaning polarity and motility) are critical for tumor progression, Wnt/PCP signaling has been implicated in cancer. (Camilli, T. C., Biochem. 2010, Pharmacol. 80(5): 702-711).

The Wnt/$Ca2^+$ pathway involves the release of intracellular calcium downstream of Wnt signaling. Members of the Wnt family involved in the Wnt/$Ca^{2+}$ signaling pathway include Wnt5a, Wnt11, and Wnt4, and activation of the Fz receptors by these Wnts was shown to result in the activation of calcium-dependent signaling molecules, such as calmodulin-dependent protein kinase II (CAMKII) and protein kinase C (PKC). These molecules can have a cornucopia of effects on downstream signaling that is often dependent on the cellular context. (Camilli, T. C., Biochem. 2010, Pharmacol. 80(5): 702-711).

More Noncanonical Wnt cascades (pathways) have been suggested including Wnt-RAP1 signaling; Wnt-receptor tyrosine kinase-like orphan receptor 2 (Ror2) signaling; Wnt-protein kinase A signaling; Wnt-GSK-3-mirotubule signaling; Wnt-atypical protein kinase C (PKC) signaling; Wnt-receptor-like tyrosine kinase signaling; and Wnt-mammalian target of rampamycin signaling. These classifications are not rigid since the pathways overlap and intersect with one another and are evolving. (Semenov, M. V.; Cell 2007, 131: 1378).

Endogenous Wnt Antagonists

Activation of the Wnt pathway is regulated by secreted Wnt inhibitors (Miller J R, et al., Oncogene 1999, 18(55): 7860-72). These inhibitors affect the binding of the Wnt ligands to their receptors or co-receptors. These Wnt antagonists include the members of the secreted frizzled related proteins (sFRPs) that bind to Wnt proteins directly, and the members of the Dikkopf (Dkk) family that bind to the Wnt co-receptors LRPs. The transcriptional inaction of sFRPs has been detected in a number of cancers, including colorectal cancer (Suzuki H, et al., 2002, 31(2):141-9). Members of the Dkk family have also been shown to have an inhibitory effect on Wnt signaling (Wu, W, et al., Curr Biol 2000, 10(24):611-1614).

Role and Function of Wnt5a

Wnt5a, in accordance with its different effects in the presence of different receptors, has been shown to have either a tumor suppressive or an oncogenic function, depending on the type of cancer. For example, its expression is down-regulated in colorectal cancer, ductal breast cancer, leukemia, and neuroblastoma. (Blanc, E. et al., Oncol Rep., 2005 14(6):1583-1588). Conversely, Wnt5a was shown to be overexpressed in gastric cancer, pancreatic cancer, non-small cell lung cancer, and prostate cancer. Wnt5a gene expression was found to be increased in more metastatic melanoma cells and increased expression led to increased motility. (Weeraratna A T et al., Cancer Cell, 2002, 1(3): 279-288).

Loss of Wnt5a protein expression is associated with shorter recurrence-free survival in breast carcinoma patients and increased motility in mammary cell lines. Based on sequence analysis of Wnt5a, 14 peptide fragments and a variety of peptide derivatives have been identified and their ability to mimic the effects of Wnt5a on mammary cell adhesion and impaired migration in a breast cancer cell line have been reported. Foxy-5, a hexapeptide (formyl-Met-Asp-Gly-Cys-Glu-Leu), derived from the 12-amino acid long peptide fragment 175 (Asn-Lys-Thr-Ser-Glu-Gly-Met-Asp-Gly-Cys-Glu-Leu) of Wnt5a, acting as an agonist of Wnt5a, was developed for use in breast cancer. It was reported that the Foxy-5 peptide restored adhesion and reduced tumor cell motility via a Frizzled-5 receptor-dependent mechanism. This formylated hexapeptide ligand induced a rapid cytosolic calcium signal, but it did not affect the cellular levels of unphophorylated β-catenin or active JNK. Foxy-5 specifically activates the G-protein-coupled protease-activated receptors 1 and 4. In mammalian cells, the hexapeptide sequence Met-Asp-Gly-Cys-Glu-Leu is present solely in Wnt-5 proteins. N-formylation of the hexapeptide cannot be found in mammalian cells. In vitro analyses revealed that both recombinant Wnt5a and Wnt5a-derived Foxy-5 peptide impaired migration and invasion without affecting apoptosis or proliferation of 4T1 breast cancer cells. In vivo experiments showed that i.p. injections of Foxy-5 inhibited metastasis of inoculated 4T1 breast cancer cells from the mammary fat pad to the lungs and liver by 70% to 90% (Safholm, A, et al., Clin Cancer Res, 2008, 14(20):6556-6563).

In melanoma, elevated Wnt5a expression promotes cell motility and drives metastasis. Two approaches were explored to counteract these effects: inhibition of Wnt5a expression or direct blockage of Wnt5a signaling. Box5, a hexapeptide (t-butoxycarbonyl-Met-Asp-Gly-Cys-Glu-Leu), modified from Foxy-5, developed for use in melanoma, is a potent, selective antagonist of Wnt5a-mediated migration and invasion of melanoma cells, both of which are essential components of the metastatic process in melanoma (Jenei, V. et al., PNAS, 2009, 106 (46): 19473-19478).

Gene expression profiling has indicated that Wnt5a may be a marker of aggressiveness in melanomas (Bittner M, et al., Nature, 2000, 406:536-540), where Wnt5a overexpression correlates significantly with the survival and the development of metastases.

Although it has been implicated in metastatic processes for non-brain cancers, Wnt5a has not been extensively studied in gliomas.

Brain Cancer (Glioma and Medulloblastoma) and Wnt5a Pathways

Immunohistochemical analyses revealed that Wnt5a expression was higher in human GBM than in normal brain tissue and in low-grade astrocytoma. The overexpression of Wnt5a increased the proliferation of GBM-05 and U87MG cells in vitro. In contrast, the downregulation of Wnt5a expression as the result of RNA interference reduced proliferation of GBM-05 and U87MG cells in vitro, and reduced tumorigenicity of these cells in vivo. The data suggested that Wnt5a signaling is an important regulator in the proliferation of human glioma cells (Yu, J. M., et al., Cancer Lett., 2007, 257(2):172-181).

Gliomas exhibit a progression associated with widespread infiltration into surrounding neuronal tissues. An independent study of the role of Wnt5a signaling in human glioma has been conducted to unravel the mechanism that stimulates this invasiveness. The results showed that Wnt5a was predominantly and commonly overexpressed among all 19 Wnt families in glioma-derived cell lines; Fz-2, -6, and -7 were dominantly expressed among 10 Fz members in glioma-derived cell lines; and expression of Ror2, a Wnt5a receptor, was very low. These findings suggest that signaling pathways could be activated in glioma cells through overexpression of Wnts or Fz. An immunohistochemical study also revealed high expression of Wnt-5a in 26 (79%) of 33 human glioma cases. The positivity of Wnt-5a expression was correlated with the clinical grade. Knockdown of Wnt-5a expression suppressed migration, invasion and expression of matrix metalloproteinase-2 of glioma cells. Reciprocally, treatment with purified Wnt5a ligand resulted in stimulation of cell migration and invasion. MMP-2 inhibitor suppressed the Wnt5a-dependent invasion of U251 cells (Kamino, M., et al., Cancer Sci, 2011, 102(3): 540-548).

The receptors of Wnt5a that mediate cellular responses of glioma have not been identified. It has been reported that knockdown of receptor-like tyrosine kinase (Ryk), but not of Ror2, suppressed the activity of MMP-2 and Wnt5a-dependent invasive activity in glioma cells. These results suggest that Ryk is important for the Wnt5a-dependent induction of MMP-2 and invasive activity in glioma-derived cells, and that Ryk might have a novel patho-physiological function in adult cancer invasion (Habu, M., et al., J. Biochem, 2014, 156(1): 29-38).

Medulloblastoma (MB), the most common type of primary brain tumor occurring in children, is the most common infratentorial primitive neuroectodermal tumor (PNET) originating in the brain and is a highly malignant primary brain tumor. The canonical signaling pathway is well known in MB. In contrast, very little research about the non-canonical Wnt signaling pathways in MB has been done. Recent studies in MB demonstrate that Wnt5a and Ror2 are additional mechanisms contributing to dysregulation of the non-canonical Wnt signaling pathway, and that Ror2 may play a role as an oncosuppressor (Lee, S. E., et al., Brain Pathology, 2013, 23: 445-453).

In each case, the aforementioned studies targeted Wnt5a signaling pathway in bulk brain glioma tumor cells.

Brain Cancer Stem Cells (or CNS Cancer Stem Cells)

Traditionally, stem cells were thought to be located only in tissues where differentiated cells were most susceptible to loss and the need for replacement great, such as the skin (Huelsken et al., Cell 105: 533-45, 2001), intestinal epithelia (Potten et al., Development 110: 1001-20, 1990) and the blood (Morrison et al., Annu Rev Cell Dev Biol 11: 3-71, 1995). Indeed, the best-known example of an adult stem cell is the hematopoietic stem cell (HSC), which is found in the bone marrow and is ultimately responsible for the generation of al blood cell types throughout the life of the animal (Morrison et al., supra.; Weissman, Cell 100: 157-68, 2000; Weissman, Science 287: 1442-6, 2000). Since the adult central nervous system (CNS) was thought not to exhibit a significant amount of neuronal death, and to have no regenerative capacity, the existence of neural stem cells seemed both unlikely, and unnecessary. However, in 1992 two independent groups successfully demonstrated the existence of precursor cells within the adult mammalian CNS with the ability to give rise to new neurons (Reynolds and Weiss, Science 255: 1707-10, 1992; Richards et al., Proc Natl Acad Sci USA 89: 8591-5, 1992). The source of the new neurons was identified as stem cells that line the entire ventricular neuroaxis of the adult mammalian CNS (Reynolds and Weiss, 1992).

Like stem cells found in other tissues, CNS stem cells (or neural stem cells (NSCs)) have been shown to demonstrate the defining in vitro stem cell characteristics (Hall et al., Development 106: 619-33, 1989; Potten et al, supra.) of proliferation, extensive self-renewal, generation of a large number of progeny, multi-lineage differentiation potential and the in vivo characteristic of regenerating tissue after injury.

One role of stem cells is to divide and give rise to more committed precursor cells with the ability to proliferate and generate a large number of undifferentiated cells. Ultimately, it is the progeny of these more committed precursor cells types that give rise to differentiated progeny. Thus, stem cells can be thought of as a relatively quiescent reservoir of uncommitted cells with the ability to divide throughout the lifespan of the animal and with an extensive proliferation potential, while progenitor cells are more committed and divide more frequently but have more limited proliferation potential over time. Both during development, and in the adult, the proliferation of stem and progenitor cells underpins cell genesis.

The concept of tumors arising from a small population of cells with stem cell characteristics that contribute to the growth and propagation of the tumor is not new to the cancer biology field. The idea was proposed in early 1970's and experimentally confirmed in studies on acute myelogenous leukemia (AML), where low frequency tumor initiating cells were demonstrated to resemble normal hematopoietic stem cells (HSCs). These studies suggested that leukemia stem cells were the direct descendants of HSC or the produce of a more differentiated cell that had acquired HSC features. Discovery of stem cells outside of the blood system raised the possibility that cancers of solid tissues may also contain stem like cells. The existence and isolation of tumor initiating stem-like cells in solid tumors was first demonstrated in human breast cancer tissue, an approach that has also been applied to tumors of the CNS.

Several groups have reported on the ability of cells derived from human glioma tissue to generate neurosphere-like cells in culture, suggesting the presence of NSCs within CNS tumors. It has been demonstrated, based on fluorescence activated cell sorting (FACS) isolation of "side-population" cells, that the well-established glioma cell line U87MG contains a minor population of neurosphere-forming cells that retain in vivo malignancy (C. Hirschmann-Jax, Proc Natl Acad Sci 2004, 101(39):14228-233). Galli and colleagues (Galli et al., Cancer Research (2004) 64: 7011-7021) reported on the isolation, propagation and serial transplantation of tumor neural stem cells (tNSCs) from human glioblastoma multiforme (GBM) that exhibit near identical functional properties as NSCs derived from embryonic and adult CNS. These GBM tNSCs are prominin positive precursors, which display the critical neural stem cell features in vitro, can be expanded in a stable fashion and, throughout serial transplantation-culturing cycles, reproduce the original tumor-initiating characteristics. Together, these studies strongly support the hypothesis that CNS tumors contain a population of stem cells that may be responsible for tumor initiation and malignancy. The tNSCs can be sorted from other GBM cells using FACS by virtue of the expression of CD133 on the tNSCs (Singh et al., Nature (2004) 532:396-401).

The cancer stem cell (CSC) hypothesis suggests that cancers are organized into aberrant cell hierarchies in which "differentiated" daughter cells that have limited capacity to proliferate are produced by a subset of parent CSCs that replicate indefinitely, i.e., only CSCs have the capacity to sustain tumor growth and are responsible for recurrence after therapy fails (Gilbertson, Nature, 2012, 488(7412): 462-463). Until 2012, evidence for the existence of cancer stem cells had been controversial. Drissens (Driessens, G., Nature, 2012, 742: 527-530) and Chen (Chen, J, Nature, 2012, 7412: 522-526) provided elegant evidence to support the existence of CSCs, which offers a sea change in the way we think about and treat cancers.

Cancer Stem Cell Markers

CD133 is considered a marker of stem cells in diverse normal tissues and cancer types. With regard to brain tumors, Singh et al. were the first to describe a CD133 positive tumor cell population, with stem cells characteristics, that is capable of self-renewal and exact recapitulation of the original tumor when transplanted into immunodeficient mouse brains (Singh S K, et al., Nature 2004, 432: 396-401; Singh S K, et al., Cancer Res 2003, 63:5821-5828). Other putative markers of GCSCs include L1CAM, CD44, CD15, Integrin α6 (Brescia P., J Carcinogene Mutagene 2011, 51), and EphA2 (Binda E., et al., Cancer Cell 2012, 22(6): 765-780). The neuronal cell adhesion molecule L1CAM (L1, CD171) is required for maintaining the growth and survival of CD 133 positive glioma cells with stem-like properties. Several reports have shown the utility of the cell surface marker CD44 in the identification of cancer stem cells in different type of tumors, including one example of the use of CD44 as a stem cell marker in glioblastoma (Anido J, et al., Cancer Cell 2010, 18:656-668). CD15 is a cell surface protein selectively expressed in cells with tumor initiation capacity. Integrin α6, important for the interaction with laminin expressing endothelial cells in the microenvironment, is a component of the extracellular matrix whose contact is important for glioma stem cells maintenance. The integrin-α6-laminin interaction has been reported to play an important role in the subventricular zone (SVZ) of the lateral ventricles in the adult brain. EphA2 receptor tyrosine kinase is overexpressed in hGBM TPCs and drives self-renewal and tumorigenicity in hGBM TPCs (Binda E., et al., Cancer Cell 2012, 22(6):765-780).

Gliomas Cancer Stem Cells (GCSC) Targeting Treatment

GCSCs are distinguished by the ability to self-renew, the ability to initiate brain tumors, the expression of neural stem cell markers, and multipotency, which is the capacity to differentiate into cells with a neuronal, astrocytic, or oligodendroglial phenotype. GCSCs express antigens specific for neural stem and progenitor cells: Nestin, CD133 (prominin-1), Musashi-1, and Bmi-1. Sonic hedgehog homolog (SHH) and Notch are key regulators of neural progenitors and have been found to be altered or overexpressed in GCSCs (Nakada, M. et al., Cancers, 2011, 3: 3242-3278). FIG. 6 shows Gliomas cancer stem cell pathways.

GCSCs are radioresistant and chemoresistant, which eventually results in tumor recurrence. Targeting GCSCs for treatment is critical. Five general methods have been proposed for targeting the GSCs: (1) to develop new therapeutic agents to target signaling pathways of CSCs; (2) to use a radio-sensitizer to enhance the radiotherapy effect on CSCs; (3) to use immune cells to attack the CSCs: (4) to use a differentiation agent to promote the CSCs to differentiate into normal cells; and (5) gene therapy (Cho, et al., Cell Transplant. 2013, 22(4):731-9).

Therapeutic agents have been used to target signal pathways to treat GBM, include Wnt pathways, sonic hedgehog (shh), Notch, homeobox (HOx) family, B-lymphoma Mo-MLV insertion region 1 homolog (Bmi-1), PTEN, telomerase, efflux transporters, EGF, micro-RNA, and VEGF receptors (Cho, et al., Cell Transplant. 2013, 22(4):731-9).

Canonical Wnt-signalling activates the translocation of β-catenin to the nucleus, where it acts as a transcription factor of specific target genes, and Wnt-β-catenin signaling has proven roles in both normal stem cells and GCSCs. Wnt-β-catenin signaling can contribute to radio-resistance in GCSCs and may be a therapeutic target for GCSCs in brain tumors, as this pathway supports motility/invasiveness of gliomas and drives changes resembling epithelial to mesenchymal transition. (Cruceru, M. L., et al., J. of Cellular & Molecular Medicine, 2013, 17(10): 1218-1235).

To date, the pathways/mechanism behind the migration, invasion, and metastasis of brain gliomas are still not understood. It is now accepted that cancer stem cells are responsible for resistance to chemo- and radio-therapy and re-occurrence of tumor cells, but to date, no research targeting the Wnt5a non-canonical signaling pathways to reduce invasiveness of glioma cancer stem cells has been reported, and no therapeutic agent that specifically targets Wnt5a non-canonical signaling pathway in brain cancer stem cells has been identified. The described invention addresses these problems and provides peptide derivatives of Wnt5a that reduce invasiveness of glioma cancer stem cells, at least in part by directly or indirectly affecting Wnt5a signaling.

SUMMARY

The described invention provides a pharmaceutical composition comprising a therapeutic agent, wherein the therapeutic agent is effective (1) to reduce tumor growth, migration, invasion or a combination and (2) improve subject survival relative to a control.

According to one aspect, the described invention provides a pharmaceutical composition to treat a solid tumor comprising a population of tumor-propagating cells with stem-like characteristics (TPCs) in a subject comprising a therapeutic amount of a therapeutic agent and a pharmaceutically acceptable carrier, wherein the therapeutic agent is a peptide derivative of Wnt5a, wherein the therapeutic amount of the therapeutic agent is effective (1) to reduce tumor growth, migration, invasion or a combination thereof relative to a control by affecting a level of expression of Wnt5a; and (2) to increase survival of the subject relative to a control.

According to another aspect, the described invention provides a method for treating a solid tumor comprising a population of tumor-propagating cells with stem-like characteristics (TPCs) in a subject comprising administering to the subject a pharmaceutical composition comprising a therapeutic amount of a therapeutic agent and a pharmaceutically acceptable carrier, wherein the therapeutic agent is a peptide derivative of Wnt5a, wherein the therapeutic amount of the therapeutic agent is effective (1) to reduce tumor growth, migration, invasion or a combination thereof relative to a control by affecting a level of expression of Wnt5a; and (2) to increase survival of the subject relative to a control.

According to another aspect, the described invention provides a pharmaceutical composition for use in treating a solid tumor comprising a population of tumor-propagating cells with stem-like characteristics (TPCs) in a subject comprising a therapeutic amount of a therapeutic agent and a pharmaceutically acceptable carrier, wherein the therapeutic agent is a peptide derivative of Wnt5a, wherein the therapeutic amount of the therapeutic agent is effective (1) to reduce tumor growth, migration, invasion or a combination thereof relative to a control by affecting a level of expression of Wnt5a; and (2) to increase survival of the subject relative to a control.

According to another aspect, the described invention provides a use of a pharmaceutical composition in the manufacture of a medicament for treating a solid tumor comprising a population of tumor-propagating cells with stem-like characteristics (TPCs) in a subject comprising administering to the subject a pharmaceutical composition comprising a therapeutic amount of a therapeutic agent and a pharmaceutically acceptable carrier, wherein the therapeutic agent is a peptide derivative of Wnt5a, wherein the therapeutic amount of the therapeutic agent is effective (1) to reduce tumor growth, migration, invasion or a combination thereof relative to a control by affecting a level of expression of Wnt5a; and (2) to increase survival of the subject relative to a control.

According to one embodiment, the solid tumor is selected from the group consisting of a brain tumor, a colon tumor, a prostate tumor, a breast tumor, a lung tumor, a skin tumor, a liver tumor, a bone tumor, an ovary tumor, a pancreas tumor, a head tumor, a neck tumor, a nerve tumor and a lymphoma. According to another embodiment, the solid tumor is a brain tumor. According to another embodiment, the brain tumor is a glioma. According to another embodiment, glioma is selected from the group consisting of an astrocytoma, an oligodendroglioma and an ependymoma. According to another embodiment, astrocytoma oligodendroglioma and ependymoma are anaplastic. According to another embodiment, astrocytoma is a glioblastoma multiforme. According to another embodiment, the brain tumor is selected from the group consisting of a medulloblastoma, a meningioma, a schwannoma, a craniopharyngioma, a germ cell tumor and a pineal region tumor.

According to one embodiment, the peptide is a Wnt5a antagonist. According to another embodiment, the peptide is synthetic. According to another embodiment, peptide is selected from the group consisting of a hexapeptide, a pentapeptide and a combination thereof. According to another embodiment, the peptide derivative of Wnt5a is a derivative of Box 5 (SEQ ID NO: 1). According to another embodiment, the hexapeptide consists of amino sequence MDGCEL (SEQ ID NO: 1). According to another embodiment, the hexapeptide consists of amino sequence LECGDM (SEQ ID NO: 2). According to another embodiment, the pentapeptide consists of amino acid sequence LEGDM (SEQ ID NO: 3).

According to one embodiment, the control is a subject not treated with the pharmaceutical composition.

According to one embodiment, the glioma comprises the glioma comprises mesenchymal tissue, proneural tissue, classical tissue or a combination thereof. According to another embodiment, the mesenchymal tissue and the proneural tissue are characterized by an increased level of expression of Wnt5a ligand relative to classical tissue. According to another embodiment, the increased level of expression of Wnt5a ligand is indicative of cell migration.

According to one embodiment, the population of tumor-propagating cells with stem-like characteristics (TPCs) is of an invasive phenotype.

According to one embodiment, modulation of Wnt5a expression and/or activity by the peptide derivative is effective to decrease invasiveness of GFI TPCs in a dose-dependent fashion.

According to one embodiment, the glioma comprises cells positive for Wnt5a ligand. According to another embodiment, the cells positive for Wnt5a ligand co-express the putative neuroblast marker PSA-NCAM with up to 60% of Wnt5a and Dlx2 positive cells immunoreactive for PSA-NCAM. According to another embodiment, the cells positive for Wnt5a ligand are characterized by an increased level of expression of CD44 relative to a control. According to another embodiment, the cells positive for Wnt5a ligand do not co-express the putative stem-like tumor propagating cells (TPCs) marker EphA2.

According to one embodiment, the invasive phenotype comprises expression of invasion marker FRAS1-related extracellular matrix protein 2 (Frem2).

According to one embodiment, the peptide derivative is effective to reduce invasion of the tumor comprising the population of tumor-propagating cells with stem-like characteristics (TPCs) through the brain parenchyma compared to an untreated control.

According to one embodiment, the method further comprising the step of measuring at least one selected from the group consisting of tumor growth, migration and invasion. According to another embodiment, the method further comprising the step of administering a second therapeutic agent. According to another embodiment, the second therapeutic agent is a chemotherapeutic agent. According to another embodiment, the second therapeutic agent is a Wnt5a antagonist. According to another embodiment, the Wnt5a antagonist is an antibody. According to another embodiment, the Wnt5a antagonist is Wnt3a. According to another embodiment, Wnt5a antagonist is a frizzled-related protein.

According to one embodiment, the composition is administered orally, buccally, parenterally, intranasally, rectally, or topically.

DETAILED DESCRIPTION OF THE INVENTION

Figure 1:
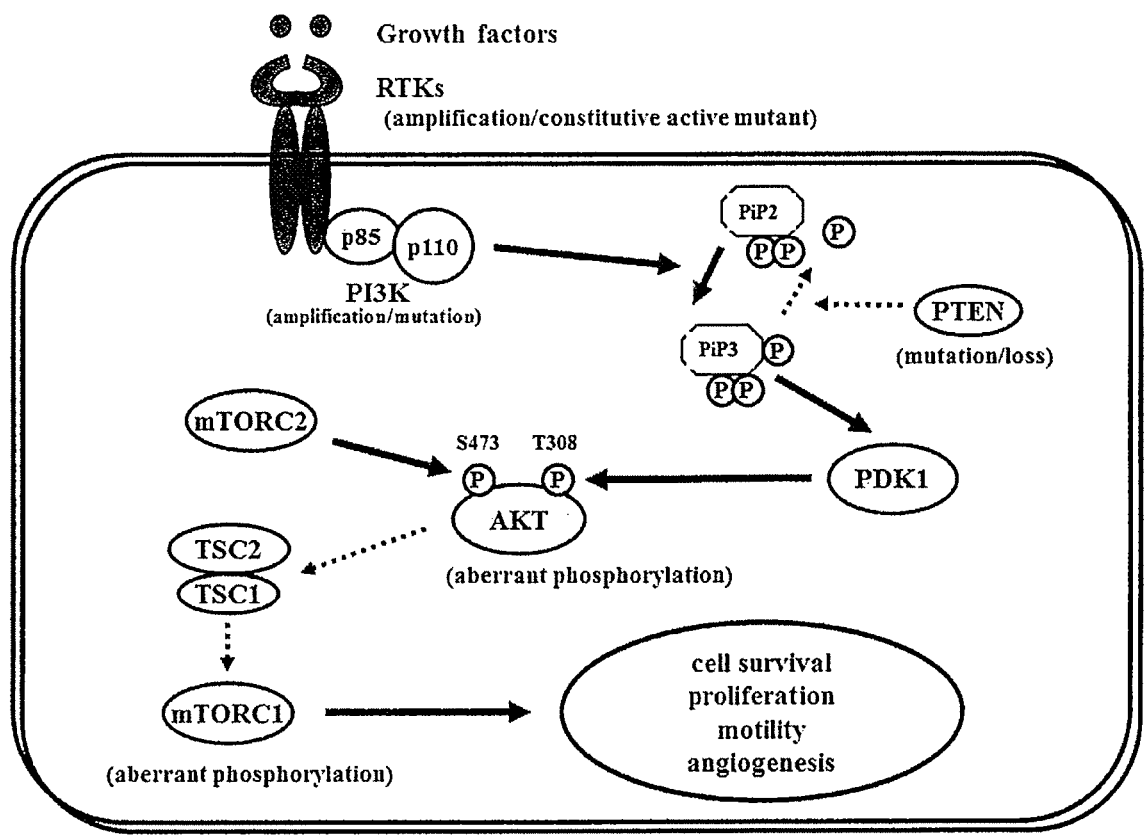
FIG. 1 shows the Receptor Tyrosine Kinase pathway (RTK/PI3K/Akt/mTOR Pathway).
Figure 2:
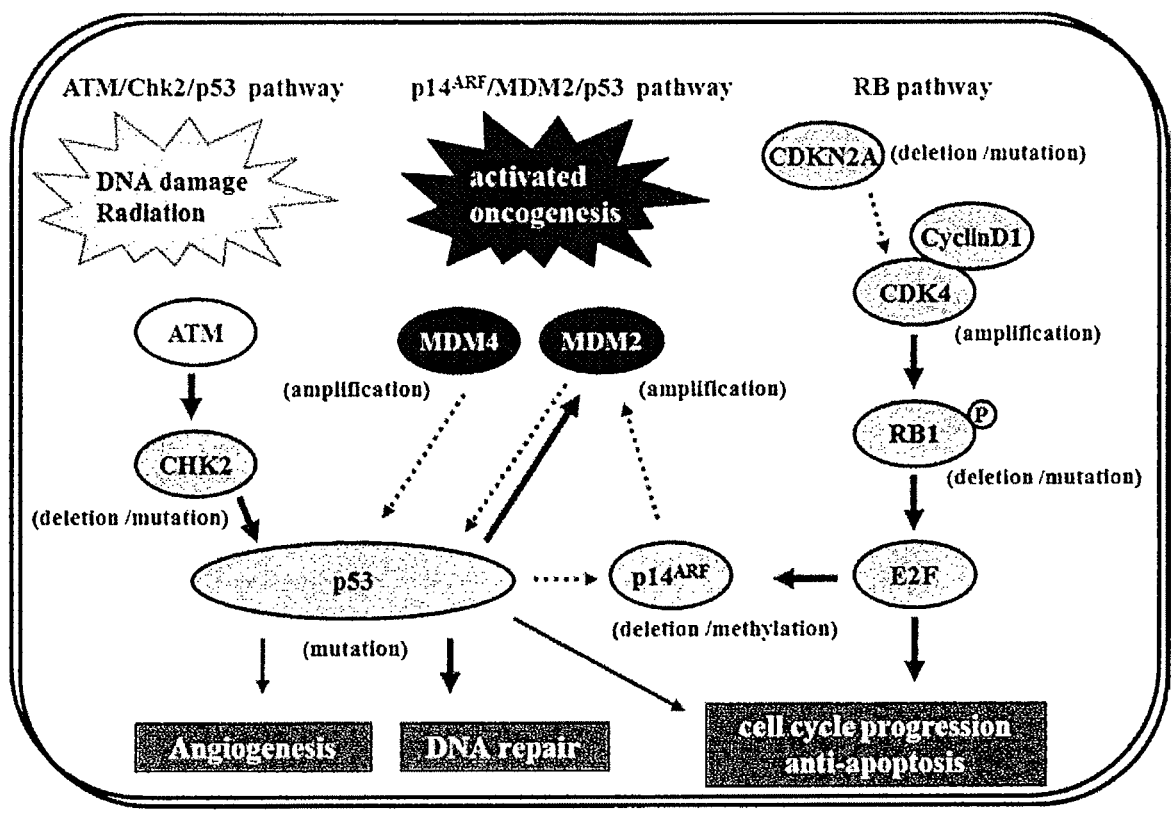
FIG. 2 shows the p14ARF/MDM2/p53 Pathway and the RB Pathway.
Figure 3:
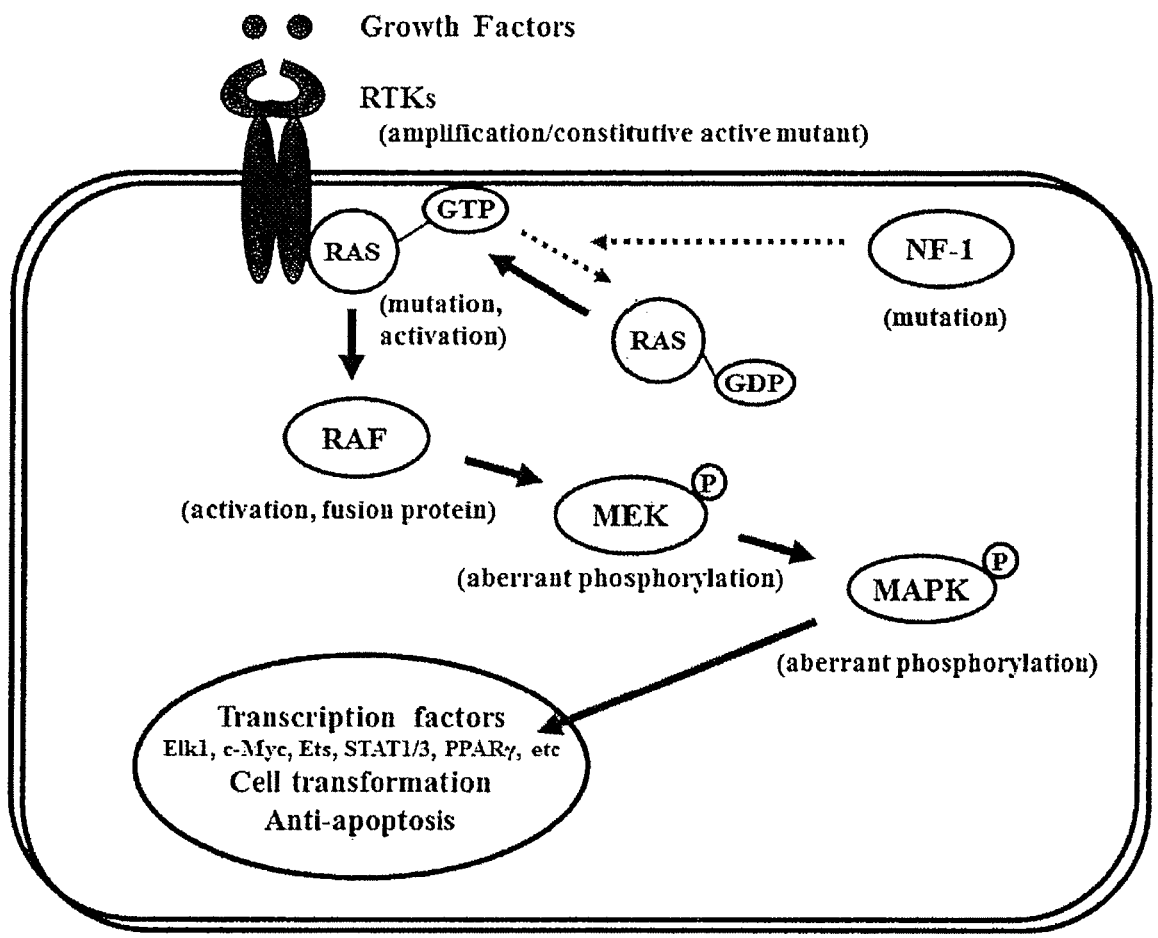
FIG. 3 shows the Ras/MEK/MAPK Pathway
Figure 4:
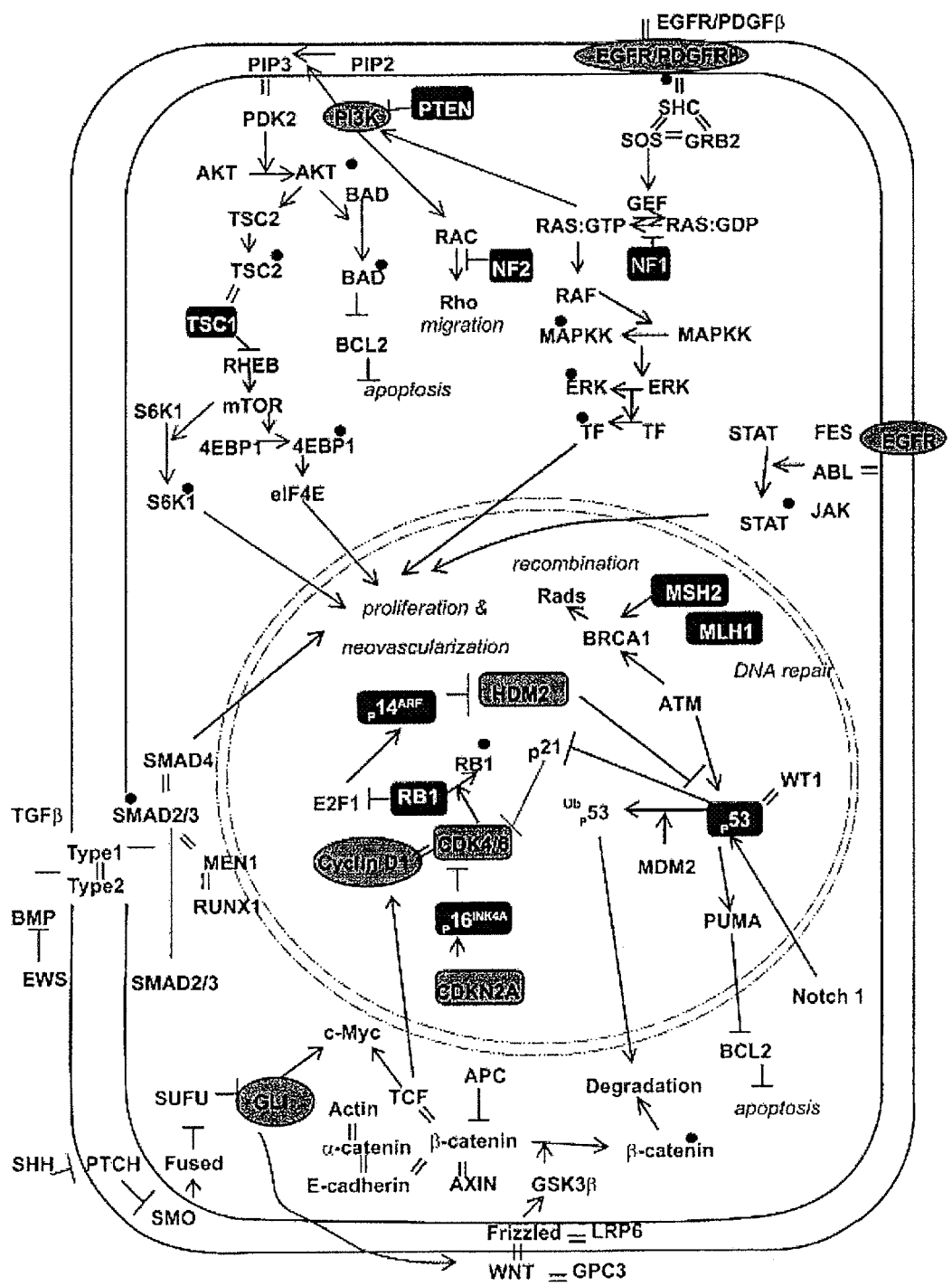
FIG. 4 shows the Global Signaling pathways implicated in GBM.
Figure 5:
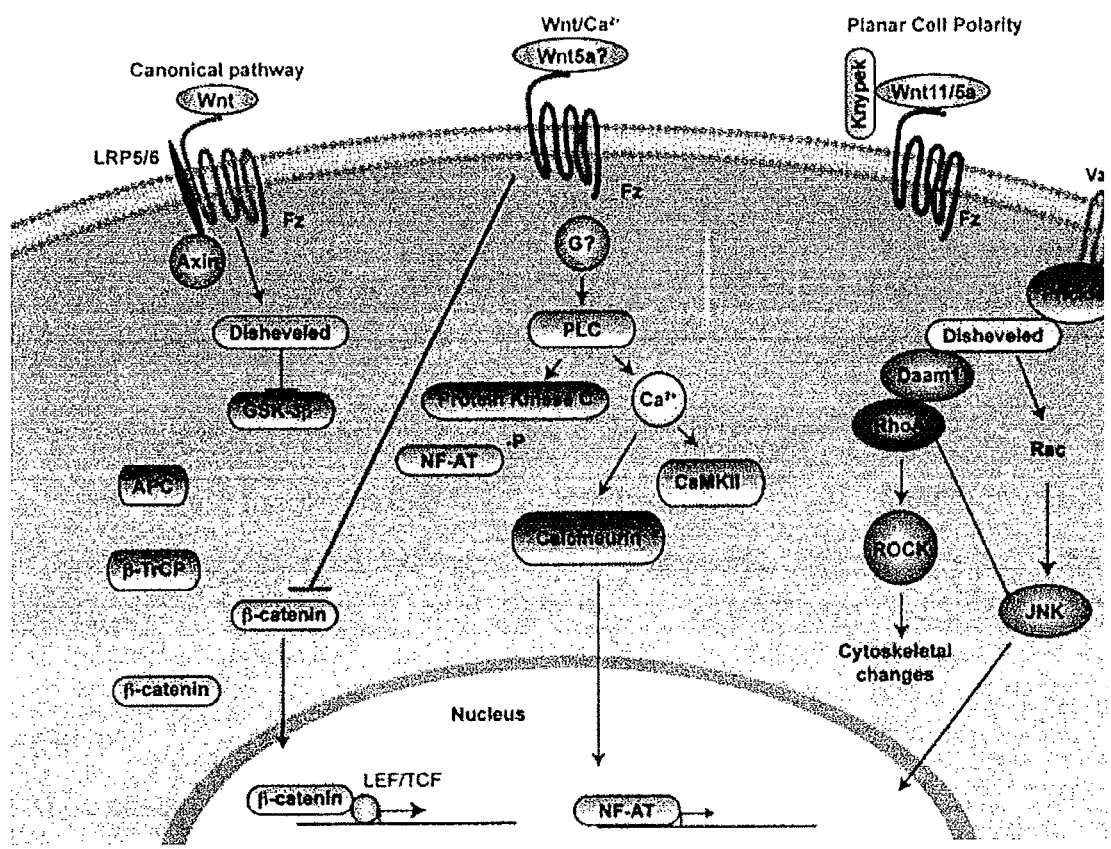
FIG. 5 shows three representative Wnt signaling pathways.
Figure 6:
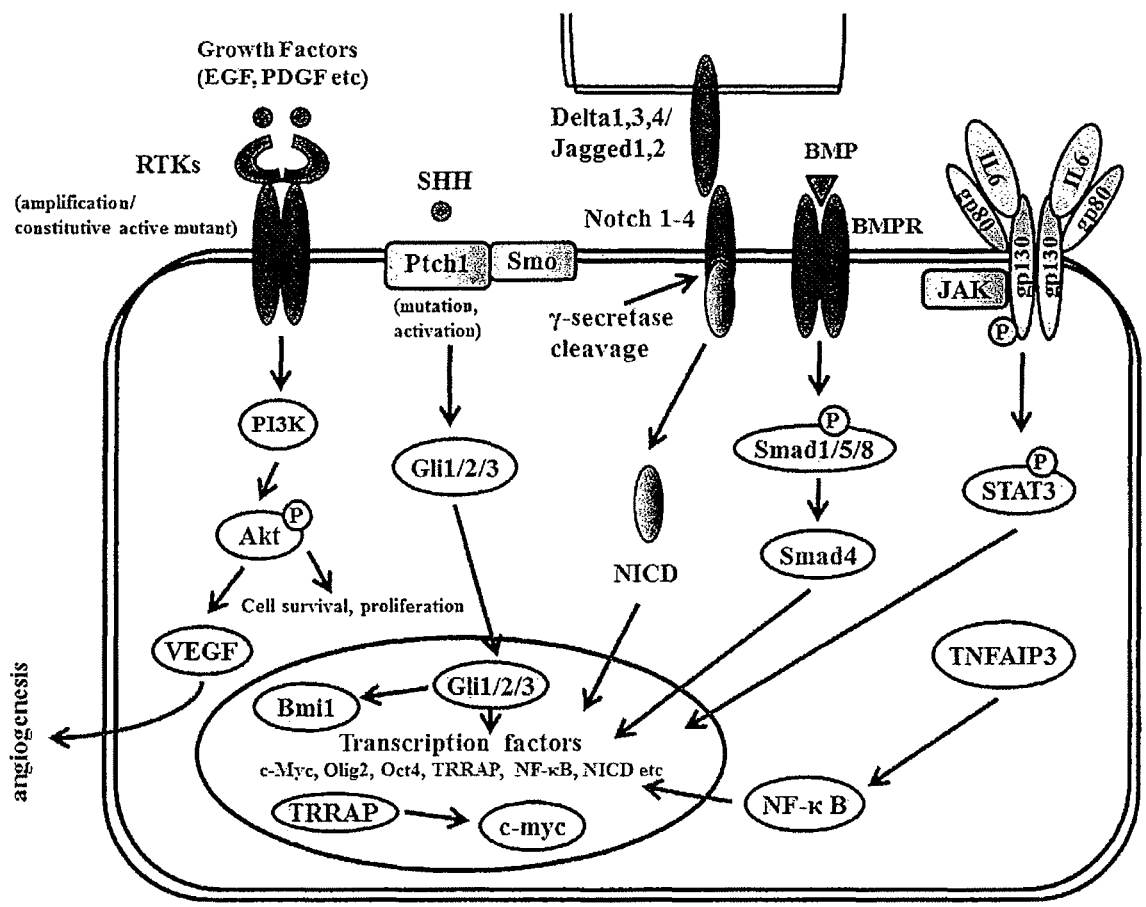
FIG. 6 shows glioma cancer stem cell pathways.

The terms "administering" or "administration" as used herein are used interchangeably to mean the giving or applying of a substance and include in vivo administration, as well as administration directly to tissue ex vivo.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A super-agonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:
Alanine (A), Serine (S), Threonine (T);
Aspartic Acid (D), Glutamic Acid (E);
Asparagine (N), Glutamine (Q);
Arginine (R), Lysine (K);
Isoleucine (I), Leucine (L), Methionine (M), Valine (V); and
Phenylalanine (F), Tyrosine (Y), Tryptophan (W).

The term "antagonist" as used herein refers to a substance that counteracts the effects of another substance. The term "antagonists of Wnt5a" as used herein refer to a peptide, protein, or antibody that can bind to Wnt5a, a Wnt5a receptor or a Wnt5a co-receptor, competitively or noncompetitively through a covalent bond, ionic bond, hydrogen bond, hydrophobic interaction, or a combination thereof and either directly or indirectly deactivate a Wnt5a signaling pathway. A Wnt5a antagonists may be formulated per se or in salt form.

The terms "cancer" or "malignancy" as used herein refer to diseases in which abnormal cells divide without control and can invade nearby tissues. Cancer cells also can spread to other parts of the body through the blood and lymph systems. Central nervous system cancers are cancers that begin in the tissues of the brain and spinal cord.

The term "cancer stem cells" as used herein refers to a population of cells that are capable of self-renewal and exact recapitulation of the original tumor when transplanted into immunodeficient mouse brains.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "cell" is used herein to refer to the structural and functional unit of living organisms and is the smallest unit of an organism classified as living.

The term "cell line" as used herein refers to an immortalized cell, which have undergone transformation and can be passed indefinitely in culture.

The term "chemotherapeutic agent" as used herein refers to chemicals useful in the treatment or control of a disease.

The term "chemotherapy" as used herein refers to a course of treatment with one or more chemotherapeutic agent.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "compatible" as used herein means that the components of a composition are capable of being combined with each other in a manner such that there is no interaction that would substantially reduce the efficacy of the composition under ordinary use conditions.

The term "composition" as used herein refers to a mixture of ingredients, or a material formed of two or more substances.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)). The term "peptide derivative" as used herein refers to an amino acid sequence produced from a Wnt5a derived peptide, either directly or by modification or partial substitution of the Wnt5a peptide. For example, and without limitation, peptide derivatives of Wnt5a include truncated and fusion Wnt5a products. Peptide derivatives of Wnt5a may be formulated per se or in salt form.

The term "effective amount" as used herein refers to the amount necessary or sufficient to realize a desired biologic effect.

The term "formulation" as used herein refers to a mixture prepared according to a specific procedure, formula, prepared according to a particular formula, recipe or rule.

The term "flow cytometry" as used herein refers to a tool for interrogating the phenotype and characteristics of cells. Flow cytometry is a system for sensing cells or particles as they move in a liquid stream through a laser (light amplification by stimulated emission of radiation)/light beam past a sensing area. The relative light-scattering and color-discriminated fluorescence of the microscopic particles is measured. Analysis and differentiation of the cells is based on size, granularity, and whether the cells is carrying fluorescent molecules in the form of either antibodies or dyes. As the cell passes through the laser beam, light is scattered in all directions, and the light scattered in the forward direction at low angles)(0.5-10° from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007).

The term "fragment" or "peptide fragment" as used herein refers to a small part derived, cut off, or broken from a larger peptide, polypeptide or protein, which retains the desired biological activity of the larger peptide, polypeptide or protein.

The term "glioma" as used herein refers to a type of tumor, which arises from glial cells in the brain or spine.

The term "growth" as used herein refers to a process of becoming larger, longer or more numerous, or an increase in size, number, or volume.

The term "interfere" or "to interfere with" as used herein refers to the hampering, impeding, dampening, hindering, obstructing, blocking, reducing or preventing of an action or occurrence. By way of example, a receptor antagonist interferes with (e.g., blocks or dampens) an agonist-mediated response rather than provoking a biological response itself.

The term "invasion" or "invasiveness" as used herein refers to a process in malignant cells that includes penetration of and movement through surrounding tissues.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "ligand" as used herein refers to a molecule that can bind selectively to a molecule, such that the binding interaction between the ligand and its binding partner is detectable over nonspecific interactions by a quantifiable assay. Derivatives, analogues and mimetic compounds are intended to be included within the definition of this term.

The terms "marker" and "cell surface marker" are used interchangeably herein to refer to a receptor, a combination of receptors, or an antigenic determinant or epitope found on the surface of a cell that allows a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Cell sorting techniques are based on cellular biomarkers where a cell surface marker(s) may be used for either positive selection or negative selection, i.e., for inclusion or exclusion, from a cell population.

The term "migration" as used herein refers to a movement of a population of cells from one place to another.

The term "mitotic index" as used herein refers to the ratio of the number of cells undergoing mitosis (cell division) to the number of cells not undergoing mitosis in a population of cells.

The term "peptide" is used herein to refer to two or more amino acids joined by a peptide bond.

The term "pharmaceutical composition" is used herein to refer to a composition that is employed to prevent, reduce in intensity, cure or otherwise treat a target condition or disease.

The term "polypeptide" is used herein in its broadest sense to refer to a sequence of subunit amino acids, amino acid analogs or peptidomimetics, wherein the subunits are linked by peptide bonds.

The term "protein" is used herein to refer to a large complex molecule or polypeptide composed of amino acids. The sequence of the amino acids in the protein is determined by the sequence of the bases in the nucleic acid sequence that encodes it.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "proliferation-inducing growth factor" is used herein to refer to Epidermal Growth Factor [EGF], basic Fibroblastic Growth Factor [bFGF] etc.

The term "subject" as used herein includes animal species of mammalian origin, including humans. It further includes cells and tissues derived from these species.

The phrase "subject in need thereof" as used herein refers to a patient that (i) will be administered at least peptide analog of the described invention, (ii) is receiving at least peptide analog of the described invention; or (iii) has received at least one peptide analog of the described invention, unless the context and usage of the phrase indicates otherwise.

The term "target" as used herein refers to a biological entity, such as, for example, but not limited to, a protein, cell, organ, or nucleic acid, whose activity can be modified by an external stimulus. Depending upon the nature of the stimulus, there may be no direct change in the target, or a conformational change in the target may be induced.

The term "therapeutic agent" as used herein refers to a drug, molecule, nucleic acid, peptide, protein, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein.

The terms "therapeutically effective amount", an "amount effective", or "pharmaceutically effective amount" of one or more of the active agents and used interchangeably to refer to an amount that is sufficient to provide the intended benefit of treatment. An effective amount of the active agents that can be employed according to the described invention generally ranges from generally about 0.01 mg/kg body weight to about 100 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition resulting from accumulation of an amyloid peptide in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "truncated" as used herein refers to shorten by cutting off residues; being cut short.

The term "tumor" as used herein refers to a diseases involving abnormal cell growth in numbers (proliferation) or in size with the potential to invade or spread to other parts of the body (metastasis).

According to one aspect, the described invention provides a pharmaceutical composition comprising a therapeutic amount of a therapeutic agent, wherein the therapeutic agent is a peptide, and wherein the therapeutic agent is effective (1) to reduce tumor growth, migration, invasion or a combination thereof and (2) to improve subject survival relative to a control.

According to one embodiment, the peptide is a peptide derivative of Box5. Such peptide derivatives include, but are not limited to, a peptide of amino acid sequence Met-Asp-Gly-Cys-Glu-Leu (MDGCEL) [SEQ ID No: 1], a peptide of sequence Leu-Glu-Cys-Gly-Asp-Met (LECGDM) [SEQ ID No: 2], a peptide of sequence Leu-Glu-Gly-Asp-Met (LEGDM) [SEQ ID No: 3], and truncated and fusion products thereof.

According to one embodiment, the peptide is a Wnt5a antagonist. Wnt5a antagonists can function to interfere with a Wnt5a-activated signaling pathway directly or indirectly, e.g., by binding to Wnt5a, by binding to a Wnt5a receptor, by preventing or reducing expression of a Wnt5a gene, by preventing or reducing expression of a Wnt5a target gene and the like. Wnt5a-activated signaling pathways include, but are not limited to, signaling pathways associated with growth, migration, invasion or a combination thereof, signaling pathways that comprise Wnt5a, canonical pathways, noncanonical pathways, and the like. According to one embodiment, the Wnt5a antagonist interferes with a signaling pathway associated with growth, migration, invasion or a combination thereof of a cancer stem cell (CSC). According to another embodiment, the Wnt5a antagonist interferes with a signaling pathway associated with growth of a cancer stem cell (CSC). According to another embodiment, the Wnt5a antagonist interferes with a signaling pathway associated with migration of a cancer stem cell (CSC). According to another embodiment, the Wnt5a antagonist interferes with a signaling pathway associated with invasion of a cancer stem cell (CSC).

According to one embodiment of the described invention, the signaling pathway is a Wnt-activated cellular signaling pathway that does not promote β-catenin-mediated transcription. According to one embodiment, the Wnt-activated cellular signaling pathway that does not promote β-catenin-mediated transcription is a noncanonical Wnt signaling pathway. According to another embodiment, the noncanonical Wnt signaling pathway involves Wnt5a.

Peptides of the described invention can be recombinantly expressed or chemically synthesized. Methods for producing recombinantly expressed or chemically synthesized peptides are known in the art.

According to one embodiment, the described invention provides synthetic peptides. Examples of methods for preparing synthetic peptides are described, for example, in Peptide Synthesis Protocols, Methods in Molecular Biology, Vol. 35, Pennington, M W and Dunn, B M, 1995, XII, Humana Press, Inc. Totowa, N.J. and Peptides: Synthesis, Structures and Applications, Gutte, B, 1995, Academic Press, Inc., San Diego, Calif.). Synthetic peptides, prepared using the techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, J. Org. Chem. 37:3403-3409). Both Fmoc and Boc N-α-amino protected amino acids can be obtained commercially, for example, from Sigma, Cambridge Research Biochemical, or other such chemical companies. Alternatively, the peptide may be synthesized with any other N-α-protecting groups.

Solid phase peptide synthesis may be accomplished as provided, for example, in Stewart and Young, 1984, Solid Phase Synthesis, Second Edition, Pierce Chemical Co., Rockford, Ill.; Fields and Noble, 1990, Int. J. Pept. Protein Res. 35:161-214, or using automated synthesizers. The peptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine.

In addition, the peptides can have peptidomimetic bonds, such as ester bonds, to prepare peptides with novel properties. For example, a peptide may be generated that incorporates a reduced peptide bond, i.e., R1-CH2-NH—R2, where R1 and R2 are amino acid residues or sequences. A reduced peptide bond may be introduced as a dipeptide subunit. Such a peptide would be resistant to protease activity, and would possess an extended half-life in vivo.

It is understood that synthetic peptides can be from about two (2) to about thirty (30) amino acids in length. According to one embodiment, the described invention provides the synthetic peptide set forth in SEQ ID NO: 1 and its variants. According to one embodiment, the described invention provides the synthetic peptide set forth in SEQ ID NO: 2 and its variants. According to one embodiment, the described invention provides the synthetic peptide set forth in SEQ ID NO: 3 and its variants. The synthetic peptide variants can contain a substitution, deletion or addition of an amino acid. The substitution can include a conservative amino acid substitution. The deletion or addition can include a single amino acid or several amino acids.

The described invention contemplates both linear and cyclic forms of peptides. Cyclic peptides can be formed, for example, by an amide bond or disulfide bridge. A disulfide bridge can be formed between two residues of the amino acid cysteine.

The described invention contemplates a second therapeutic agent in addition to the described peptides. Non-limiting examples of the second therapeutic agent include a chemotherapeutic agent, an antagonist of Wnt5a and the like. Non-limiting examples of Wnt5a antagonists include antibodies (e.g., a Wnt5a blocking antibody), frizzled-related protein or protein analogs, or Wnt3a protein or protein analogs. Wnt5a antagonists can function to interfere with a Wnt5a-activated signaling pathway directly or indirectly, e.g., by binding to Wnt5a, by binding to Wnt5a receptors, by preventing or reducing expression of a Wnt5a gene, by preventing or reducing expression of a Wnt5a target gene and the like. Wnt5a-activated signaling pathways include, but are not limited to, signaling pathways associated with growth, migration, invasion or a combination thereof, signaling pathways that comprise Wnt5a, canonical pathways, noncanonical pathways, and the like. According to one embodiment, the Wnta antagonist interferes with a signaling pathway associated with growth, migration, invasion or a combination thereof of a cancer stem cell (CSC). According to one embodiment, the Wnt5a antagonist interferes with a signaling pathway associated with growth of a cancer stem cell (CSC). According to one embodiment, the Wnt5a antagonist interferes with a signaling pathway associated with migration of a cancer stem cell (CSC). According to one embodiment, the Wnt5a antagonist interferes with a signaling pathway associated with invasion of a cancer stem cell (CSC).

According to one embodiment of the described invention, the signaling pathway is a Wnt-activated cellular signaling pathway that does not promote. β-catenin-mediated transcription. According to one embodiment, the Wnt-activated cellular signaling pathway that does not promote β-catenin-mediated transcription is a noncanonical Wnt signaling pathway. According to another embodiment, the noncanonical Wnt signaling pathway involves Wnt5a.

According to one embodiment, the tumor is a solid tumor. Solid tumors include, but are not limited to, a brain tumor, a colon tumor, a prostate tumor, a breast tumor, a lung tumor, a skin tumor, a liver tumor, a bone tumor, an ovary tumor, a pancreas tumor, a head tumor, a neck tumor, a nerve tumor and a lymphoma. Non-limiting examples of brain tumors include a medulloblastoma, a meningioma, a schwannoma, a craniopharyngioma, a germ cell tumor, a pineal region tumor and a glioma. Exemplary gliomas include astrocytoma, oligodendroglioma, ependymoma and the like. A non-limiting example of an astrocytoma is a glioblastoma multiforme.

According to one embodiment, the glioma comprises tumor cells. According to another embodiment, the tumor cells comprise cancer stem cells.

According to one embodiment, the tumor comprises a population of live tumor cells. According to another embodiment, the population of live tumor cells comprises a population of cancer stem cells.

According to one embodiment, the population of cancer stem cells is characterized by an invasive phenotype. The invasive phenotype can be characterized by expression of a Ki67 marker, a CD147 marker a Frem2 marker or a combination thereof. According to another embodiment, the population of cancer stem cells shows infrequent coexpression of Wnt5a and EphA2.

According to one embodiment, the cancer stem cells invasive phenotype shows a high level of expression of Wnt5a.

According to another embodiment, the population of tumor cells is characterized by at least one of (1) a high level of expression of Wnt5a and CD44, (2) a high level of expression of Wnt5a or EphA2 or (3) a high level of expression of Wnt5a and Dlx2. According to another embodiment, the population of tumor cells is characterized by the presence of three (3) over-expressing Wnt5a cell types: (1) subventricular zone (SVZ) astrocyte, Type B: Glial fibrillary acidic protein (GFAP+); (2) transient amplifying progenitor, Type C: GFAP−, Dlx2+, PSA-NCAM− and (3) neuroblast, Type A: GFAP−, Dlx2+, PSA-NCAM+.

According to one embodiment, the population of cancer stem cells is cultured without exposure to a growth factor. According to another embodiment, the population of cancer stem cells cultured without exposure to a growth factor shows a high level of expression of Wnt5a when compared to a population of cancer stem cells cultured with growth factor (control).

According to one embodiment, the described invention provides a pharmaceutical composition comprising a therapeutic agent that reduces invasion of the cancer stem cells.

According to one embodiment, the described invention provides a therapeutic agent that reduces a level of Wnt5a expression.

According to another embodiment, the pharmaceutical composition of the described invention further comprises a pharmaceutically acceptable carrier. According to another embodiment, the pharmaceutical composition further comprises a chemotherapeutic agent.

According to one embodiment, the pharmaceutical composition of the described invention is effective to interfere with one or more steps in a signaling pathway associated with tumor growth, migration and invasion. According to another embodiment, the pharmaceutical composition of the described invention is effective to interfere with a step in a Wnt5a signaling pathway.

According to another aspect, the described invention provides a method for reducing tumor growth, migration, invasion, or a combination thereof in a subject in need thereof, the method comprising (1) administering to the subject a pharmaceutical composition comprising a therapeutic amount of a peptide, wherein the therapeutic amount is effective to interfere with a step in a signaling pathway associated with tumor growth, migration, invasion, or a combination thereof.

According to one embodiment, the described invention also provides a method for treating a subject with a solid CNS tumor, the method comprising: (1) providing a pharmaceutical composition comprising a therapeutic amount of a therapeutic agent, wherein the therapeutic agent is a peptide, the therapeutic amount of which is effective to reduce tumor growth, migration, invasion or a combination thereof; and (2) administering the composition to a subject in need thereof.

According to one embodiment, the method comprises administering a composition to a subject, wherein the composition comprises (1) a therapeutic amount of a Box5 peptide derivative, a Wnt5a blocking antibody, a Wnt5a antagonist, a protein binding to Wnt5a receptor, a protein binding to Wnt5a co-receptor, or Wnt3a and (2) pharmaceutically acceptable carriers.

According to one embodiment, the described invention provides a method of treating a subject with a tumor comprising a population of cancer stem cells of an invasive phenotype, the method comprises administering a pharmaceutical composition to a subject in need thereof; wherein the cancer stem cells of the invasive phenotype have a high level of expression of Wnt5a.

According to one embodiment, the pharmaceutical composition comprises a therapeutically effective amount of a peptide derivative of Boxy, wherein the derivative is selected from peptide A (SEQ ID NO: 2), peptide B (SEQ ID NO: 3), or a combination thereof.

According to one embodiment, the described invention provides a route for administering the pharmaceutical composition. Routes of administration include, but are not limited to, oral, buccal, parenteral, intranasal, rectal and topical.

The pharmaceutical compositions of the described invention may be in a form suitable for oral use, for example, as tablets, troches, lozenges, aqueous or oily suspensions, dispersible powders or granules, emulsions, hard or soft capsules or syrups or elixirs. As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled release.

Compositions of the described invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the described invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for, example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the described invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Compositions of the described invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, or example, sweetening, flavoring and coloring agents also may be present.

The compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the described invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded (meaning torn or cut) tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the described invention may take the form of tablets or lozenges formulated in a conventional manner.

The compositions of the described invention may be in the form of a sterile injectable aqueous or oleaginous suspension. The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the described invention is delivered using a needle, e.g., a surgical needle. The term "surgical needle" as used herein, refers to any needle adapted for delivery of fluid (i.e., capable of flow) compositions of the described invention into a selected anatomical structure. Injectable preparations, such as sterile injectable aqueous or oleaginous suspensions, may be formulated according to the known art using suitable dispersing or wetting agents and suspending agents.

The sterile injectable preparation also may be a sterile injectable solution or suspension in a nontoxic parenterally acceptable diluent or solvent, for example, as a solution in 1,3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. Spray drying, for example, is a process in which a homogeneous aqueous mixture of drug and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. The solvent, generally water, rapidly evaporates from the droplets producing a fine dry powder having particles from about 1 µm to 5 µm in diameter. The spray drying is done under conditions that result in a substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 µm or less with about 90% of the mass being in particles having a diameter less than 5 µm. Alternatively, about 95% of the mass will have particles with a diameter of less than 10 µm with about 80% of the mass of the particles having a diameter of less than 5 µm. Dry powder compositions also may be prepared by lyophilization and jet milling, as disclosed in International Patent Publication No. WO 91/16038, the disclosure of which are incorporated by reference.

The term "dispersibility" or "dispersible" means a dry powder having a moisture content of less than about 10% by weight (% w) water, usually below about 5% w and preferably less than about 3% w; a particle size of about 1.0-5.0 µm mass median diameter (MMD), usually 1.0-4.0 μm MMD, and preferably 1.0-3.0 μm MMD; a delivered dose of about >30%, usually >40%, preferably >50%, and most preferred >60%; and an aerosol particle size distribution of about 1.0-5.0 μm mass median aerodynamic diameter (MMAD), usually 1.5-4.5 μm MMAD, and preferably 1.5-4.0 μm MMAD. Methods and compositions for improving dispersibility are disclosed in U.S. application Ser. No. 08/423,568, filed Apr. 14, 1995, the disclosure of which is hereby incorporated by reference.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns (μm) in diameter with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content such that the particles are readily dispersible in an inhalation device to form an aerosol. This moisture content is generally below about 10% by weight (% w) water, usually below about 5% w and preferably less than about 3% w.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. Preferably about 5% w to about 95% will be used. The carrier may be one or a combination of two or more pharmaceutical excipients, but generally will be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the described invention are readily absorbed in the lungs without the need to employ penetration enhancers.

The types of pharmaceutical excipients that are useful as carriers for pulmonary delivery include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable for pulmonary delivery include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose, maltodextrins, and mannitol. Suitable polypeptides include aspartame. Amino acids include alanine and glycine, with glycine being preferred.

Additives, which are minor components of the composition for pulmonary delivery, may be included for conformational stability during spray drying and for improving dispersibility of the powder. These additives include hydrophobic amino acids such as tryptophan, tyrosine, leucine, phenylalanine, and the like.

For delivery by inhalation or insufflation, the composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the described invention may be used in the form of drops or sprays (e.g., a nasal spray, aerosol spray, or pump spray) or other vehicles for nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention, especially those formulated for intranasal administration, can also be provided as solutions, suspensions, or viscous compositions (e.g., gels, lotions, creams, or ointments).

The compositions of the described invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system," transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation.

Patches suitable for use in the described invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

In some embodiments, the compositions of the described invention may be formulated with an excipient, vehicle or carrier selected from solvents, suspending agents, binding agents, fillers, lubricants, disintegrants, and wetting agents/surfactants/solubilizing agents. The terms "excipient", "vehicle", or "carrier" refer to substances that facilitate the use of, but do not deleteriously react with, the active compound(s) when mixed with it. The term "active" refers to the ingredient, component or constituent of the compositions of the described invention responsible for the intended therapeutic effect. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to pregelatinized maize starch, polyvinylpyrrolidone or hydroxypropyl methylcellulose); fillers (including but not limited to lactose and other sugars, microcrystalline cellulose, pectin, gelatin, calcium sulfate, ethyl cellulose, polyacrylates or calcium hydrogen phosphate); lubricants (including, but not limited to magnesium stearate, talc, silica, sollidal silicon dioxide, stearic acid, metallic stearates, hydrogenated vegetable oils, corn starch, polyethylene glycols, sodium benzoate, sodium acetate); disintegrants (including but not limited to starch, sodium starch glycolate) and wetting agents (including but not limited to sodium lauryl sulfate). Additional suitable carriers for the compositions of the described invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

The term "pharmaceutically acceptable carrier" as used herein refers to any substantially non-toxic carrier conventionally useful for administration of pharmaceuticals in which the active component will remain stable and bioavailable. In some embodiments, the pharmaceutically acceptable carrier of the compositions of the described invention include a release agent such as a sustained release or delayed release carrier. In such embodiments, the carrier can be any material capable of sustained or delayed release of the therapeutic amount of the therapeutic agent to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The therapeutically active peptides of the described invention can be formulated per se or in salt form. The term "pharmaceutically acceptable salts" refers to nontoxic salts of the peptides of the described invention. The peptide salts which can be used for the invention are pharmaceutically acceptable salts of organic acids or pharmaceutically acceptable salts of inorganic acids. Examples of such pharmaceutically acceptable peptide salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Additional compositions of the described invention can be prepared readily using technology known in the art, such as that which is described in Remington's Pharmaceutical Sciences, 18th or 19th editions, published by the Mack Publishing Company of Easton, Pa., which is incorporated herein by reference.

According to some embodiments, the compositions of the described invention can further include one or more compatible active ingredients aimed at providing the composition with another pharmaceutical effect in addition to that provided by a Wnt5a derivative peptide, Wnt5a mimic peptide, a Wnt5a antagonist, or a Wnt5a blocking antibody. "Compatible" as used herein means that the active ingredients of such a composition are capable of being combined with each other in such a manner so that there is no interaction that would substantially reduce the efficacy of each active ingredient or the composition under ordinary use conditions.

The composition of the described invention also may be administered serially or in combination with other compositions for treating brain tumors. For example, without limitation, such other compositions may include bone morphogenetic protein 4 (BMP4); and anti-inflammatory compounds (including, but not limited to nonsteroidal anti-inflammatory drugs (NSAIDs), such as ibuprofen, indomethacin, and flurbiprofen).

The composition of the described invention, alone or in combination with other active ingredients, may be administered to a subject in a single dose or multiple doses over a period of time. As used herein, the terms "therapeutically effective amounts," "therapeutic amount", and "pharmaceutically effective amounts" are used interchangeably to refer to the amount of the composition of the invention that results in a therapeutic or beneficial effect following its administration to a subject. Additionally, the terms "therapeutically effective amount", "therapeutic amount" and "pharmaceutically effective amount" include prophylactic or preventative amounts of the compositions of the described invention. In prophylactic or preventative applications of the described invention, pharmaceutical compositions or medicaments are administered to a patient susceptible to, or otherwise at risk of tumors comprising a population of cancer stem cells with an invasive phenotype in an amount sufficient to eliminate or reduce the risk, lessen the severity, or delay the onset of the tumors, including biochemical, histologic and/or behavioral symptoms of the tumors, its complications and intermediate pathological phenotypes presenting during development of the tumors.

The concentration of the active substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the described invention to be used for an intended purpose. Additionally, in therapeutic applications of the described invention, compositions or medicants are administered to a patient suspected of, having, or already suffering from, such a disease, disorder or condition in an amount sufficient to cure, or at least partially arrest, the symptoms of the disease, disorder or condition, including its complications and intermediate pathological phenotypes in development of the disease, disorder or condition. In some methods, administration of the composition of the described invention reduces or eliminates cognitive impairment in patients that have not yet developed characteristic pathology of the disease, disorder or condition.

An amount adequate to accomplish therapeutic or prophylactic treatment is defined herein as a therapeutically-effective dose. In both prophylactic and therapeutic regimes, an amount of the compositions of the described invention is usually administered in several dosages until a sufficient beneficial response has been achieved. Typically, the response is monitored and repeated dosages are given if the response starts to wane. A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the described invention to achieve the desired response, and "maximum efficacy" refers to the maximum achievable effect. The amount of compounds in the compositions of the described invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, N.Y., 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the described invention are those large enough to produce the desired therapeutic effect. The therapeutically effective amount of the compositions of the described invention can be administered one or more times per day on a regular basis. A typical dose administered to a subject is between about 0.01 mg of the composition per kg (of body weight) per day and about 0.5 mg of the composition per kg (of body weight) per day. For example, without limitation, the minimum dose of the composition is contemplated as about 0.01 mg/kg/day, about 0.025 mg/kg/day, about 0.05 mg/kg/day, about 0.075 mg/kg/day, about 0.08 mg/kg/day, about 0.1 mg/kg/day, about 0.125 mg/kg/day, about 0.15 mg/kg/day, about 0.175 mg/kg/day, about 0.2 mg/kg/day, about 0.225 mg/kg/day, about 0.25 mg/kg/day, about 0.275 mg/kg/day, about 0.3 mg/kg/day, about 0.325 mg/kg/day, about 0.35 mg/kg/day, about 0.375 mg/kg/day, about 0.4 mg/kg/day, about 0.45 mg/kg/day, about 0.475 mg/kg/day, or about 0.5 mg/kg/day and the maximum dose is contemplated as about 0.5 mg/kg/day, about 0.475 mg/kg/day, about 0.45 mg/kg/day, about 0.4 mg/kg/day, about 0.375 mg/kg/day, about 0.35 mg/kg/day, about 0.325 mg/kg/day, about 0.3 mg/kg/day, about 0.275 mg/kg/day, about 0.25 mg/kg/day, about 0.225 mg/kg/day, about 0.2 mg/kg/day, about 0.175 mg/kg/day, about 0.15 mg/kg/day, about 0.125 mg/kg/day, about 0.1 mg/kg/day, about 0.08 mg/kg/day, about 0.075 mg/kg/day, about 0.05 mg/kg/day, about 0.025 mg/kg/day, or about 0.01 mg/kg/day. In some embodiments of the invention in humans, the dose may be about 0.01 mg to about 0.3 mg of the composition per kg (of body weight) per day, and in other embodiments in humans, between 0.01 and 0.08 mg of the composition per kg (of body weight) per day.

Those skilled in the art will recognize that initial indications of the appropriate therapeutic dosage of the compositions of the described invention can be determined in in vitro and in vivo animal model systems, and in human clinical trials. The goal of such studies is to identify a dosage that can safely be administered without generating toxicity or other side effects. For acute treatment, the therapeutic dosage be close to the maximum tolerated dose. For chronic treatment, lower dosages may be desirable because of concerns about long term toxic effects.

The therapeutic effect, i.e., of reducing tumor growth, migration, invasion, or a combination thereof in a human subject, can be determined by methods known in the art. Tumor growth can be determined by techniques, including, without limitation, doubling time (DT) (i.e., the time it takes for a tumor to double in volume), specific growth rate (i.e., the percentage growth of the tumor per day), Response Evaluation Criteria in Solid Tumors (RECIST) and the like. Such techniques typically involve one or more imaging techniques known in the art. Exemplary imaging techniques include computerized tomography (CT) or computerized axial tomography (CAT) scan, positron emission tomography (PET), magnetic resonance imaging (MRI), optical imaging and the like. Optical imaging techniques include, without limitation, bioluminescence imaging (BLI) and fluorescence imaging (FLI). Tumor migration can be determined by techniques, including, without limitation, transwell system or Boyden chamber, wound healing, durotaxis assay, micropipette, 3D extracellular matrix (ECM), micropatterned, microfluidic and intravital imaging. Intravital imaging includes imaging techniques routinely used in the art, including, but not limited to, multiphoton microscopy. Tumor invasion can be determined by techniques, including without limitation, Matrigel™ (solubilized basement membrane preparation extracted from Engelbreth-Holm-Swarm mouse sarcoma cells), Laminin I, Collagen I, and Collagen IV assays.

Where a range of values is provided, it is understood that each intervening value, to the tenth of the unit of the lower limit unless the context clearly dictates otherwise, between the upper and lower limit of that stated range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods

Immunolabelinq/Immunofluorescence Labeling

Immunolabeling/Immunofluorescence labeling are biochemical processes that enable the detection and localization of an antigen to a particular site within a cell, tissue, or organ. Cell staining can be divided into four steps: cell preparation, fixation, application of antibody, and evaluation.

First, cells are attached to a solid support to allow easy handling in subsequent procedures. This can be achieved by several methods, for example, adherent cells may be grown on microscope slides, coverslips, or on an optically suitable plastic support. Suspension cells can be centrifuged onto glass slides, bound to solid support using chemical linkers, or in some cases handled in suspension. Then, the cells are fixed and permeabilized to ensure access of the antibody to its antigen. Wide ranges of fixatives are available, and the correct choice of method will depend on the nature of the antigen being examined and on the properties of the antibody used. Fixation methods fall generally into two classes: organic solvents and cross-linking reagents. Organic solvents such as alcohols and acetone remove lipids and dehydrate the cells, while precipitating the proteins on the cellular architecture. Cross-linking reagents (such as paraformaldehyde) form intermolecular bridges, normally through free amino groups, thus creating a network of linked antigens. Cross-linkers preserve cell structure better than organic solvents, but may reduce the antigenicity of some cell components, and require the addition of a permeabilization step to allow access of the antibody to the specimen. Fixation with both methods may denature protein antigens, and for this reason, antibodies prepared against denatured proteins may be more useful for cell staining. The appropriate fixation method can be chosen according to the relevant application. The following is an exemplary protocol for immunofluorescence and labeling.

Cells are removed from an incubator and rinsed in PBS. Excess solution is removed and cells are fixed in 3-4% paraformaldehyde for 10-20 minutes and then rinsed briefly with PBS. The cells are then permeabilized with 0.5% Triton X-100 for 2-20 minutes and then washed three times (at least 5 minutes each) with PBS. Primary antibody is diluted in PBS to an appropriate dilution, applied with coverslips and incubated for 60 minutes at room temperature. The cells are then washed three times (at least 5 minutes each) with PBS. The fluorescence labeled secondary antibody is diluted to an appropriate dilution in PBS, applied with coverslips and incubated for 30 minutes at room temperature. The cells are then washed three times (at least 5 minutes each) with PBS. Excess PBS is removed, coverslips mounted with mounting medium and inverted onto glass slides.

Neurosphere Assay (NA)—to Identify, Propagate and Enumerate Neural Stem Cells (NSCs) In Vitro Due to the lack of any specific morphological, molecular or antigenic signature, stem cells have been identified based on a functional criterion. A culture methodology referred to as a Neurosphere Assay (NA) (Renolds and Weiss, Science, 1992, 225: 1707-1710) can be used to identify, propagate and enumerate NSCs in vitro. Briefly, the NA involves the microdissection of CNS tissue (e.g., embryonic through adult), disruption of cell to cell contacts, and the generation of a suspension of single cells. Cells are plated (typically at a low density) in tissue cultureware in a defined serum-free medium in the presence of at least one proliferation-inducing growth factor (i.e. Epidermal Growth Factor [EGF], basic Fibroblastic Growth Factor [bFGF] etc.). Under these conditions, within 2-5 days a multipotent NSC population begins to divide giving rise to a clonally derived cluster of undifferentiated cells referred to as a neurosphere. In the continued presence of the proliferation inducing factor, the cells in the neurosphere continue to divide, resulting in an increase in the number of cells comprising the neurosphere and consequently the size of the neurosphere. Neurospheres are collected, disrupted to a single cell suspension, and the cells replated in culture to generate new neurospheres. Passing of NSC in this manner results in an arithmetic increase in viable CNS precursor cells. The NA assay allows for NSCs to be isolated and expanded in defined conditions so the behavior of the putative stem cells can be studied under different experimental conditions.

Invasion Assays—Matrigel Invasion Assays

An Invasion Assay is an in vitro system to study invasion capability of malignant and normal cells. Specific applications include assessment of the metastatic potential of tumor cells, inhibition of metastasis by extracellular matrix components or antineoplastic drugs, altered expression of cell surface proteins, or matrix metalloproteinases in metastatic cells; and invasion of normal cells such as embryonic stem cells, cytotrophoblasts, endothelial cells, and fibroblasts.

According to one embodiment, the following Matrigel invasion assay protocol is one example of an invasion assay. A coating buffer is prepared and a Matrigel Matrix aliquot is thawed at 4° C. Then, a coating solution is prepared by mixing the Matrigel Matrix with the coating buffer. A number of permeable supports are transferred into the wells of a 24-well plate and 100 ul of the diluted Matrigel is put into each well of the 24-well plate. The plate is then incubated with the coated permeable support at 37° C. for 2 h for gelling. Cells are cultured and prepared for the invasion assay, for example, growth factor dependent hGBM tumor-propagating cells with stem-like characteristic (GFD TPCs) are pretreated with saturating concentrations of recombinant Wnt5a protein (GFD+R5); lentiviral-mediated over-expression GFD cells (GFD+LV5); growth factor independent (GFI) TPCs are treated with saturating concentrations of a Wnt5a-blocking antibody (AbW5) or of a recombinant Wnt3a protein (R3) or of a recombinant secreted frizzled-related protein 1 (SFRP1), or GFI TPCs exposed to Wnt5a-derived peptides termed Box5 (SEQ ID NO: 1), Peptide A (SEQ ID NO: 2) and Peptide B (SEQ ID NO: 3) Cell suspensions are prepared in culture medium containing 5×104 cells/mL for the 24 well invasion chambers. An aliquot of 0.5 mL of cell suspension (2.5×104 cells) is then added to each 24 well invasion chamber. A chemoattractant is added to the wells of the plate (such as fibronectin as an adhesive substrate). The Cell invasion chambers are then incubated overnight in a humidified tissue culture incubator at 37° C., 5% CO2 atmosphere. The noninvaded cells on the top of the Matrigel coated permeable support are scraped off with a cotton swab. Then the permeable supports from 24-well plates are removed and stained with a cell staining solution and the invaded cells are counted under a light microscope.

Quantitative Flow Cytometry Analysis

TPCs or tumor associated macrophages are dissected and digested in a papain solution and a single-cell suspension is obtained. For cell sorting analysis, cells are centrifuged and resuspended in PBS containing DNase. Cells are then incubated with a "cocktail" of fluorochrome conjugated monoclonal antibodies detecting Wnt5a, CD44, EphA2 for 30 min at 4° C., sorted and analyzed by FACS. Cells are identified and electronically gated on forward and orthogonal light scatter signals (FSC and SSC) and fluorescent signatures (FITC or PE) into separate population based on Wnt5a, CD44, or EphA2 expression. Background fluorescence was estimated by substituting primary antibodies with specific isotype controls. Measurement of autofluorescence was also routinely conducted for each condition tested. The instrument raw data were stored electronically for archiving and data processing.

Evaluation of Tumorigenic Ability and Invasiveness In Vivo by Orthotopic Implantation Tumorigenicity was determined by injecting tumor cells into immunodeprived adult severe combined immunodeficiency (SCID) mice. (Galli et al., Cancer Res. 2004, 65:7011-7021). Tumor cells, for example, GFI TPCs, GFD TPCs, GFI TPCs pretreated with Box5 (SEQ ID NO: 1), GFI TPCs pretreated with PeptideA (SEQ ID NO: 2) were injected into SCID mice orthotopically to evaluate the tumorigenic ability and invasiveness in vivo. Also, GFD or GFI TPCs and Wnt5a-blocking protein (AbWt), alone or in combination with BMP4 (B4), Box5 (SEQ ID NO: 1) and PeptideA (SEQ ID NO: 2) were co-injected into the SCID mice.

Mice were sacrificed at different times. Serial histological reconstruction of mouse brain sections were immunolabeled for luciferase for evaluation.

Results from in vivo experiments were all subjected to statistical analysis. Survival curves were estimated using the Kaplan-Meier method.

High Performance Liquid Chromatograph (HPLC)

According to one embodiment, the following HPLC conditions are used to determine the purity of peptides: C18 Vydac column, mobile phase A: 0.1% TFA in water, mobile phase B: 0.1% TFA in acetonitrile, gradient from 5% B to 65% B in 20 minutes.

Matrix-Assisted Laser Desorption/Ionization (Maldi-Tof)

Matrix-assisted laser desorption/ionization (MALDI) is a soft ionization technique used in mass spectrometry in which a short laser pulse is used to analyze biomolecules (biopolymers such as DNA, proteins, peptides and sugars) and large organic molecules (such as polymers, dendrimers and other macromolecules), which tend to be fragile and fragment when ionized by more conventional ionization methods using a continuous laser. According to one embodiment, the following parameters for Maldi-Tof are used to determine the molecular weight of peptides: Accelerating voltage: 20000, grid voltage: 93.7%, guide wire voltage: 0.070%, low mass gate: off, delay: 100 off, negative ion: off.

Materials

Wnt5a-blocking antibody (R&D Systems, Minneapolis, Minn.), recombinant Wnt3a protein (R&D Systems, Minneapolis, Minn.), recombinant secreted frizzled-related protein 1 (R&D System), Box5 (Primm srl Peptide Synthesis, Peptide A (Primm srl Peptide Sunthesis), Peptide B (Primm srl Peptide Sunthesis).

Box5 (SEQ ID NO: 1), Peptide A (SEQ ID NO: 2) and Peptide B (SEQ ID NO: 3) were synthesized by Primm srl (Milan, Italy) via solid-phase peptide synthesis. The synthesized peptides were quality controlled by RP-HPLC and mass spectrometry.

hGBM tumor-propagating cells with stem-like characteristic (TPCs), Mesenchymal and Proneural hGBM-derived TPCs were prepared by Neurosphere Assay (NA) (Renolds and Weiss, Science, 1992, 225: 1707-1710).

Enhanced Wnt5a expression is achieved both by treating GFD cells with saturating concentrations of recombinant Wnt5a protein (GFD+R5) or by lentiviral-mediated over-expression (GFD+LV5).

Example 1

Correlation of Wnt5a Gene Expression with Histology-Graded Tumor Samples from Glioma Patients In this study, The Cancer Genome Atlas Network (TOGA) (Nature 2008, 455(23): 1061-68), Phillips (Cancer cell 2006; 9: 157-173), Freije (Cancer Res. 2004; 64: 6503-6510), Murat (J. Clin. Oncol. 2008; 26: 3015-3024), Lee (BMC med. Genomics 2008; 1:52) and Beroukhim (PNAS 2007; 104(50): 20007-20012) publicly available data sets were used to evaluate the level of Wnt5a gene expression in histology-graded tumor samples obtained from glioma patients.

Figure 7:
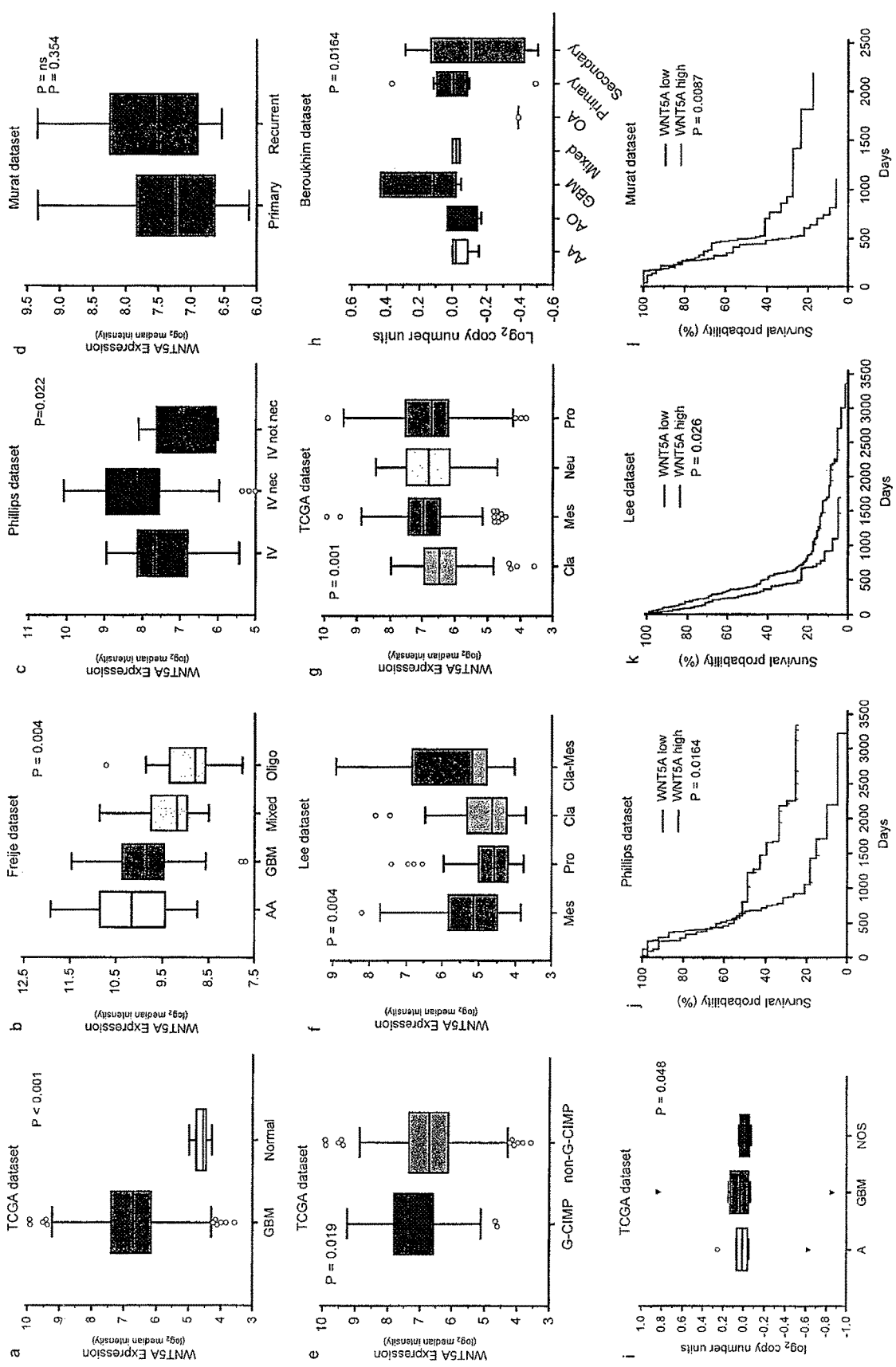
FIG. 7 shows Wnt5a expression correlates with histology of glioma patients and correlated with survival of glioma patients based on publically available data sets.

FIG. 7 shows Wnt5a gene expression in human normal brain, glioblastoma (GBM), and other brain tumor histology. Based on the publically available data sets, expression of Wnt5a was statistically significantly greater in human glioblastoma (hGBM) compared to non-malignant brain (FIG. 7a), in glioblastoma compared to other brain tumor histology (FIG. 7b), and in high necrotic glioblastoma compared to WHO grade IV non necrotic glioma (FIG. 7c). Expression of Wnt5a was not statistically significantly greater in recurrent glioblastoma compared to primary glioblastoma (FIG. 7d). Z-scores calculated on the expression levels of Wnt5a positively and significantly correlated with the existence of concerted hypermethylation at a large number of loci (glioma CpG island methylator phenotype; G-CIMP) compared to non-G-CIMP (FIG. 7e). Within subgroups of the TOGA data set, Wnt5a gene expression was significantly greater in Mesenchymal subtype as compared to Proneural and Classical subtypes (FIG. 7f-g). Wnt5a copy number correlated with malignancy in glioma patients (Beroukhim and TOGA Brain Statistics) (FIG. 7h-i). Among patients with glioblastoma, a high level of Wnt5a gene expression was associated with significantly shorter survival as compared to a low level of Wnt5a gene expression (Philips (FIG. 7j), Lee (FIG. 7k) and Murat data sets (FIG. 7l).

Figure 8:
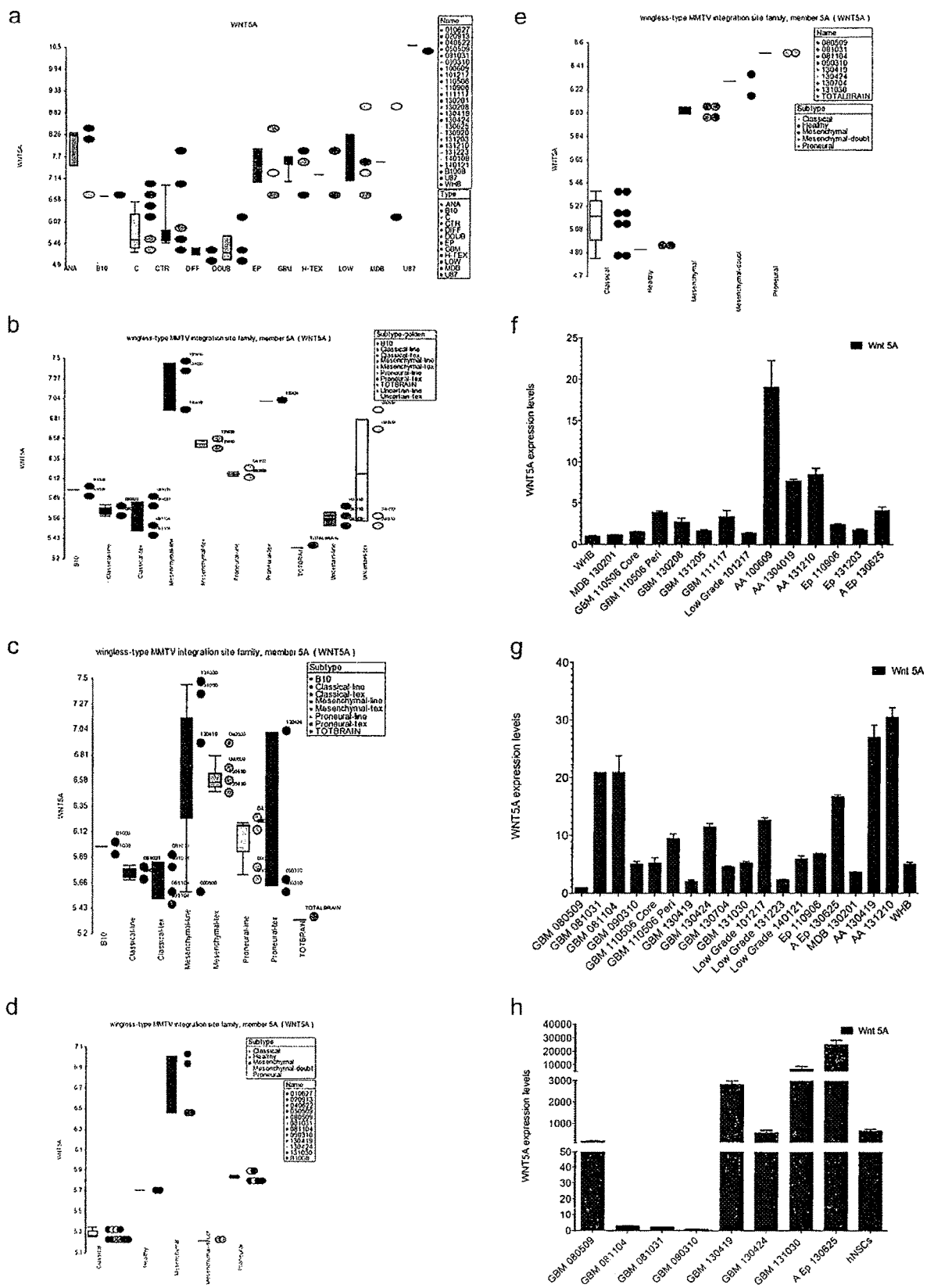
FIG. 8 shows level of Wnt5a mRNA as detected by in-silico expression profiling in anaplastic astrocytomas (ANA) and hGBM (GBM H-TEX) versus ependimoma (EP), low grade glioma (LOW) and medulloblastoma (MDB) tissues.

FIG. 8 shows the level of Wnt5a mRNA expression in histology-graded tumor samples. FIG. 8a shows higher levels of Wnt5a mRNA in anaplastic astrocytomas (ANA) and hGBM (GBM H-TEX) compared to ependimoma (EP), low grade glioma (LOW) and medulloblastoma (MDB) tissues as detected by in-silico expression profiling. hGBM tumor-propagating cells with stem-like characteristic (TPCs) cultured without the simultaneous exposure to specific combinations of growth factors (growth factor independent; GFI) (CTR) displayed higher Wnt5a levels as compared to their sibling growth factor dependent (GFD) TPCs (FIG. 8c). TPC differentiation did not cause any detectable changes in Wnt5a expression (DOUB vs. DIFF). Normal neural stem cells (hNSCs; B10) and human astrocytoma U87MG were used as control cells. Bioinformatic analysis showed that Mesenchymal and Proneural hGBM tissues and their related TPCs had the highest level of Wnt5a mRNA expression as compared to Classical tissues or cell lines and total brain or neural stem cells (B10, Healthy) (FIG. 8b-e). As shown in FIGS. 8f and 8g, quantification of Wnt5a mRNA levels by real-time PCR (qPCR) confirmed that Wnt5a was up-regulated in anaplastic astrocytomas (AA) and primary hGBMs as compared to whole human normal brain (WHB), low grade gliomas and to other types of brain tumors (Ep; ependimoma). Without being bound by theory, this evidence suggests that Wnt5a regulates the ability of a tumor cell to extensively infiltrate normal brain tissue. FIG. 8h shows that hGBM Mesenchymal (130419-131030) and Proneural (130424) tumor-propagating cells with stem-like characteristics (TPCs) expressed a greater level of Wnt5a mRNA compared to Classical TPCs (081104-081031-090310) and to human neural stem cells (hNSCs).

Figure 9:
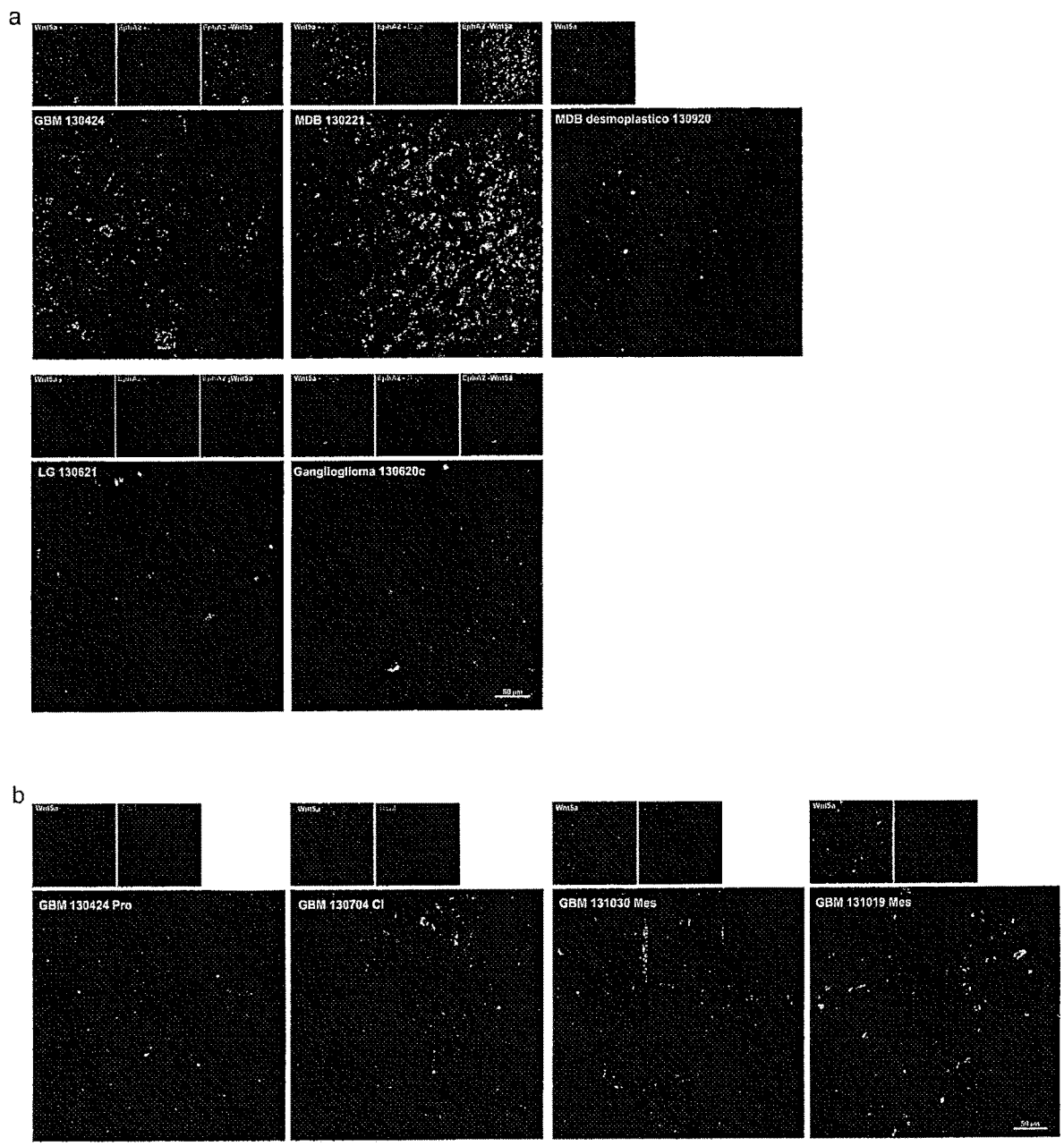
FIG. 9 shows immunolabeling of surgery specimens for Wnt5a and ephrin type-A receptor 2 (EphA2) in hGBM, MDB, low grade (LG), and ganglioglioma tissues.

FIG. 9 shows immunolabeling for Wnt5a and ephrin type-A receptor 2 (EphA2) proteins in hGBM, MDB, low grade (LG), and ganglioglioma surgical samples. In FIG. 9a, immunolabeling of surgery specimens showed strong Wnt5a immunoreactivity in many cells of hGBM and MDB tissues compared to few positive cells in low grade (LG) and ganglioglioma tissues. Immunolabeling of hGBM tissue (130424) also showed infrequent co-expression of Wnt5a protein and the TPC marker protein EphA2. Wnt5a protein expression also was higher in the more aggressive and invasive medulloblastoma (Desmoplastic MDB 130920) compared to MDB 130221 (FIG. 9a). As shown in FIG. 9b, hGBM Mesenchymal (131030 and 130419) and Proneural (130424) tissues displayed widespread immunoreactivity for Wnt5a protein as compared to hGBM Classical tissues (Scale bars, 50 µm).

Example 2

Immunofluorescence Imaging and Quantitative Flow Cytometry Analysis of Wnt5a Protein Expression In this study, immunofluorescence imaging and quantitative flow cytometry were used to detect Wnt5a protein expression in Mesenchymal and Proneural hGBM-derived TPCs as compared to Classical cells.

Figure 10:
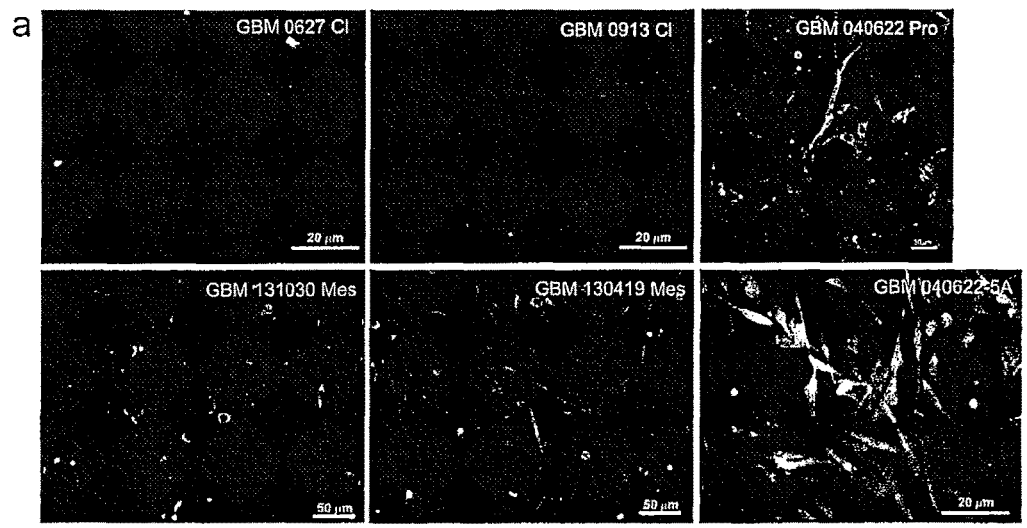
FIG. 10 shows immunofluorescence of Wnt5a in Mesenchymal and Proneural hGBM-derived tumor propagating cells with stem-like characteristic (hGBM-derived TPCs) versus Classical subtype, and in growth factor dependent (GFD) TPCs versus growth factor independent (GFI) TPCs.
Figure 10:
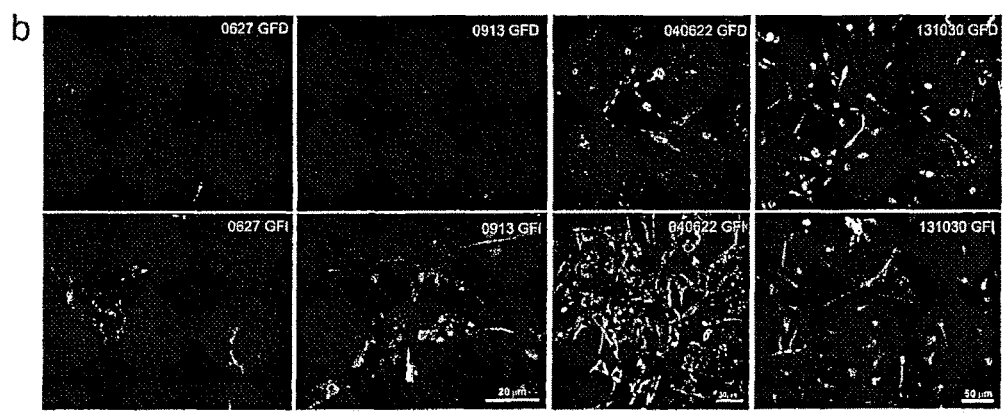
Figure 10:
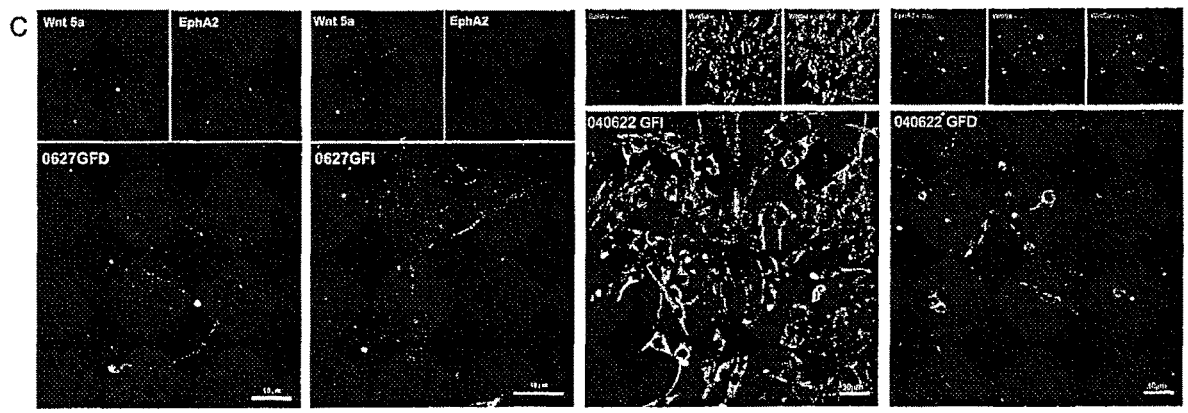

Immunofluorescence images showed a strong positivity for Wnt5a protein in Mesenchymal (131030 and 130419) and Proneural (040622) hGBM-derived TPCs compared to weaker labeling in the Classical (0627 and 0913) cells. Lentiviral-mediated over-expressed Wnt5a (040622-5A) was used as a positive control (Scale bars, 20, 30 and 50 µm) (FIG. 10a). Wnt5a protein expression also correlated with copy number variation (data not shown).

Growth factor independent hGBM TPCs (GFI TPCs), isolated either from the cognate pre-established growth factor dependent lines (GFD TPCs) or from patient's primary tumor tissue, showed a clear and intense immunoreaction (FIGS. 10b and 10c). GFI cells displayed higher Wnt5a protein expression as compared to their GFD counterpart (Scale bars, 20, 30 and 50 µm) (FIGS. 10b and 10c). Confocal images showed infrequent co-expression of Wnt5a and EphA2 protein, in GFD and GFI TPCs in which the signal for EphA2 was less obvious and intense (Scale bars, 10 and 50 µm) (FIGS. 10b and 10c).

Figure 11:
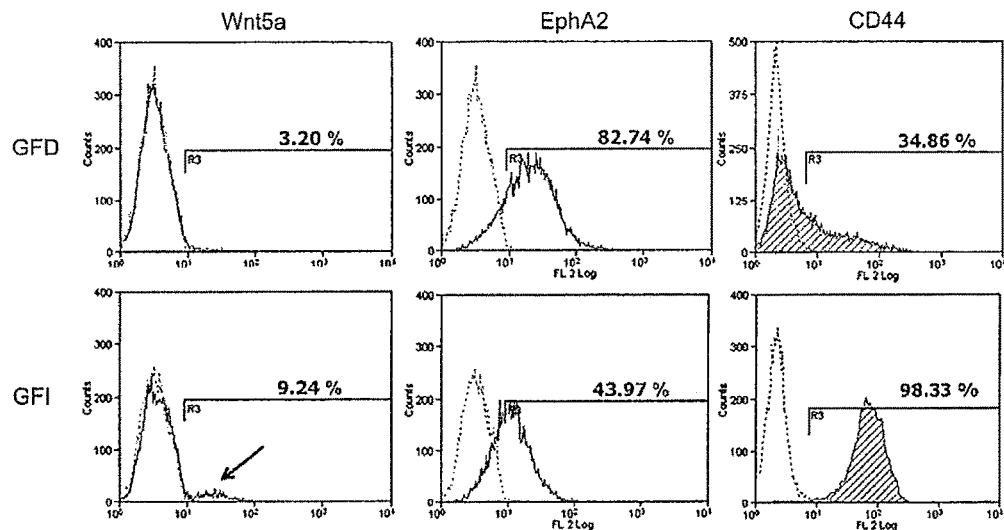
FIG. 11 shows quantitative flow cytometry analysis of Wnt5a, EphA2 and CD44 as well as quantitation of Wnt5a and Dlx2 or Wnt5a and Wnt3a mRNA levels by qPCR in GFD versus GFI TPCs.
Figure 11:
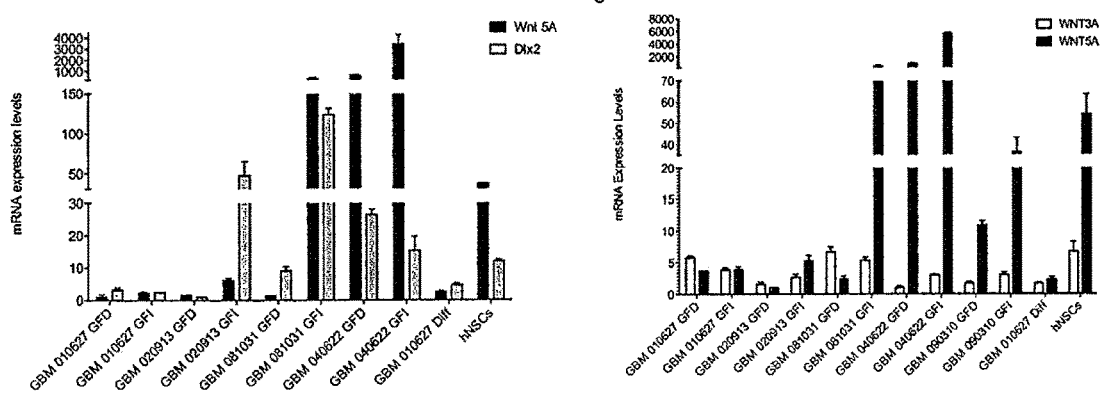
Figure 11:
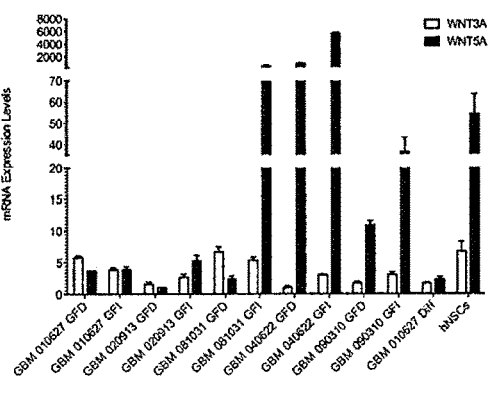
Figure 11:
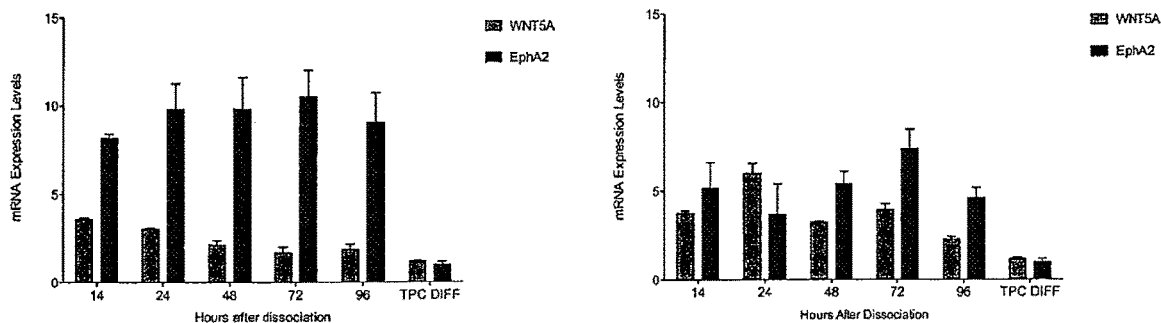

As shown in FIG. 11a, quantitative flow cytometry analysis confirmed the infrequent co-expression of Wnt5a and EphA2 proteins in GFD and GFI TPCs, which express high levels of CD44, the putative marker of cell adhesion and migration.

FIGS. 11b and 11c shows the quantification of Wnt5a and Dlx2 or Wnt5a and Wnt3a mRNA levels by qPCR in GFD and GFI TPC cells as compared to differentiated TPCs and human normal neural stem cells (hNSCs). The Dlx2 gene encodes Homeobox protein DLX2 which is a marker for transit-amplifying cells and is thought to play a role in forebrain and craniofacial development.

FIG. 11d shows time-course quantification of Wnt5a and EphA2 mRNA levels in either in GFD (left) or in GFI TPCs (right) compared to differentiated TPCs as determined by qPCR.

Figure 23:
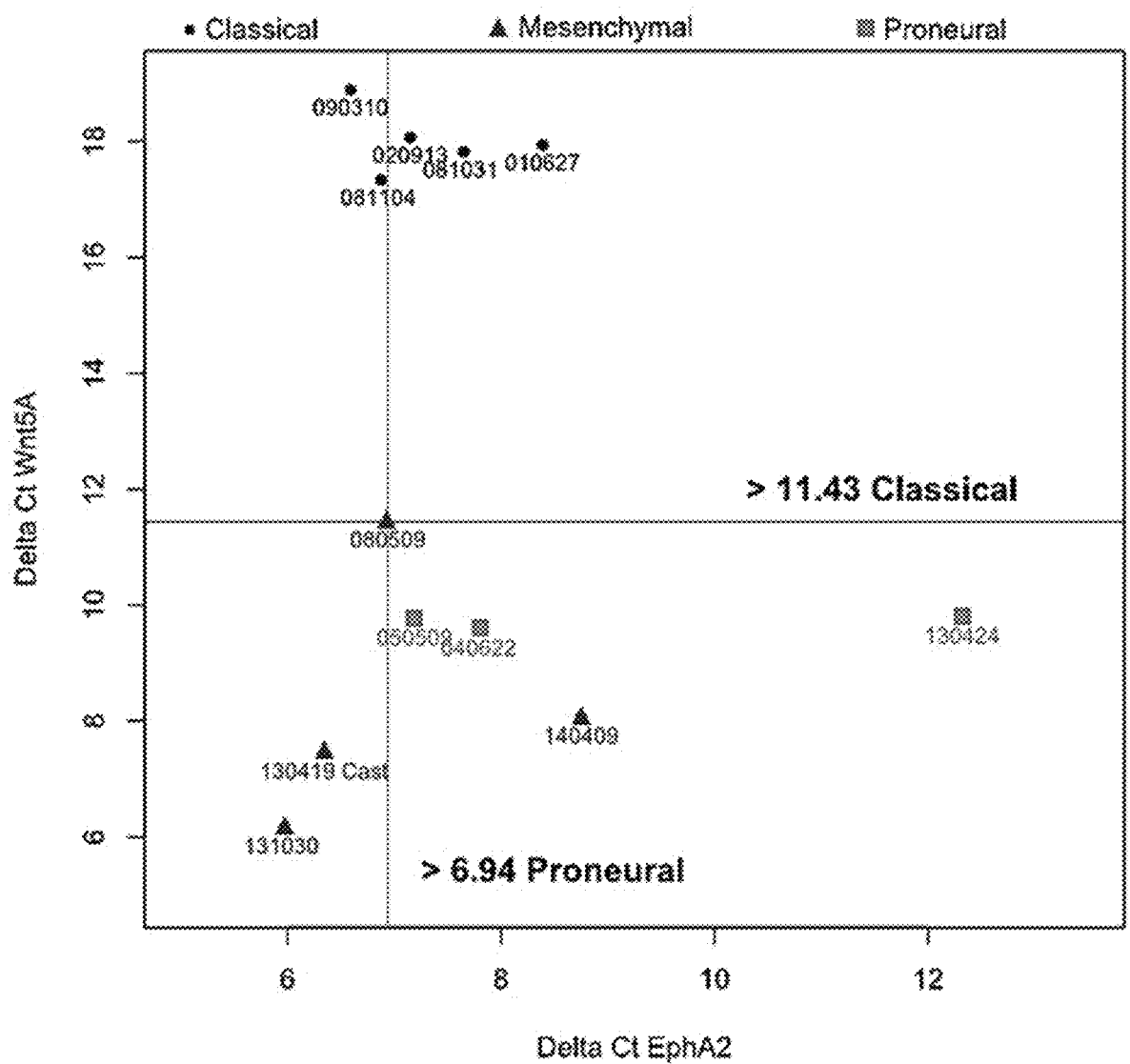
FIG. 23 shows a graph of Wnt5 gene expression (y-axis) versus EphA2 receptor gene expression (x-axis) for three subclasses of glioblastoma multiforme cells: (i) classical (circles); (ii) mesenchymal (triangles); and (iii) proneural (squares). The numbers below the shapes represent cell identification numbers.

FIG. 23 shows the correlation of Wnt5a expression to EphA2 expression for the cell lines shown. Units of the figure are Wnt5a expression on the Y-axis, and receptor expression on the X-axis. The higher the Wnt5 expression, the more the cells migrate, and the higher the receptor expression, the more the cells proliferate. By correlating Wnt5a expression to receptor expression, each cell line can be allocated to the indicated clusters. The most aggressive cell types fall into the classical subtype (circles).

Example 3

Bioinformatic Analysis of Wnt5a Gene Expression in hGBM

In this study, bioinformatics analysis was performed on hGBM specimens stained, gated and sorted according to level of Wnt5a expression.

Figure 12:
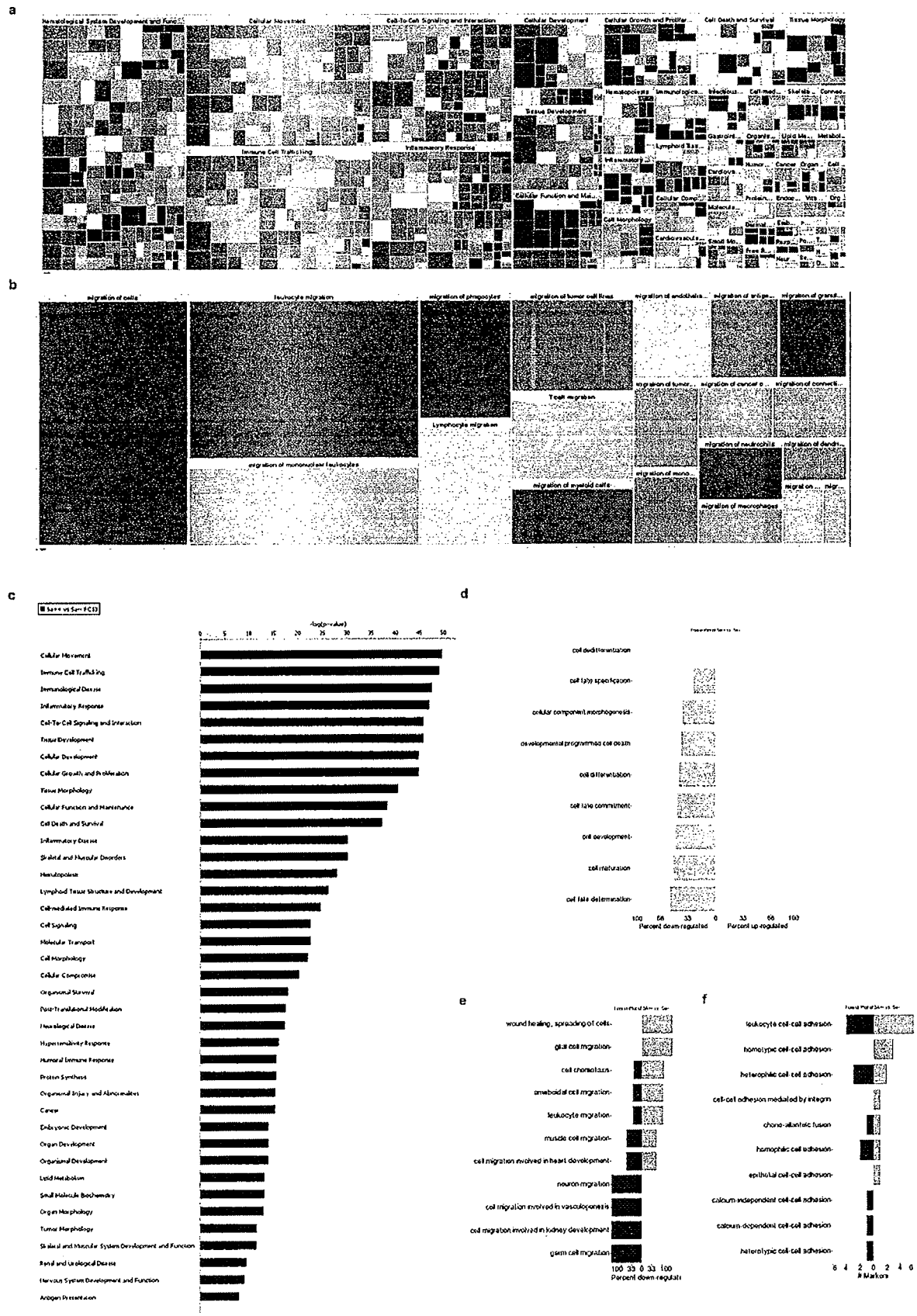
FIG. 12 shows bioinformatic analysis on hGBM specimen stained, gated and FACS sorted according to Wnt5a expression as well as Wnt5a gene signature/activation correlates with a more invasive and angiogenic phenotype.

FIGS. 12a and 12b show bioinformatic analysis performed on hGBM specimens stained, gated and FACS sorted according to Wnt5a expression. Wnt5aHigh vs Wnt5aLow gene signature/activation in TPCs and in tumor associated macrophages correlated with a more invasive and angiogenic phenotype. Without being bound by theory, this data suggests that Wnt5a regulates activities in both tumor cells and in tumor macrophages, thus resulting in increased tumor invasion (FIGS. 12a and 12b).

Gene ontology (GO) terms associated with Wnt5aHigh were sorted by statistical significance levels and represented by bars in FIG. 12c. The higher the bar, the lower the corresponding term's p-value.

FIGS. 12d and 12f show a Wnt5aHigh vs Wnt5aLow enriched set of biological processes involved in cell development, cell adhesion and cell migration.

Example 4

Expression and Correlation of Wnt5a, EphA2 and DLX2 in Human GBM Tissues

In this study, analysis of the publicly available data sets (TOGA, Phillips and Lee), and immunofluorescent staining of hGBM and MDB were used to determine whether the co-expression of Wnt5a with either EphA2 or DLX2 correlates with malignancy in, and/or survival of, glioma patients.

Figure 13:
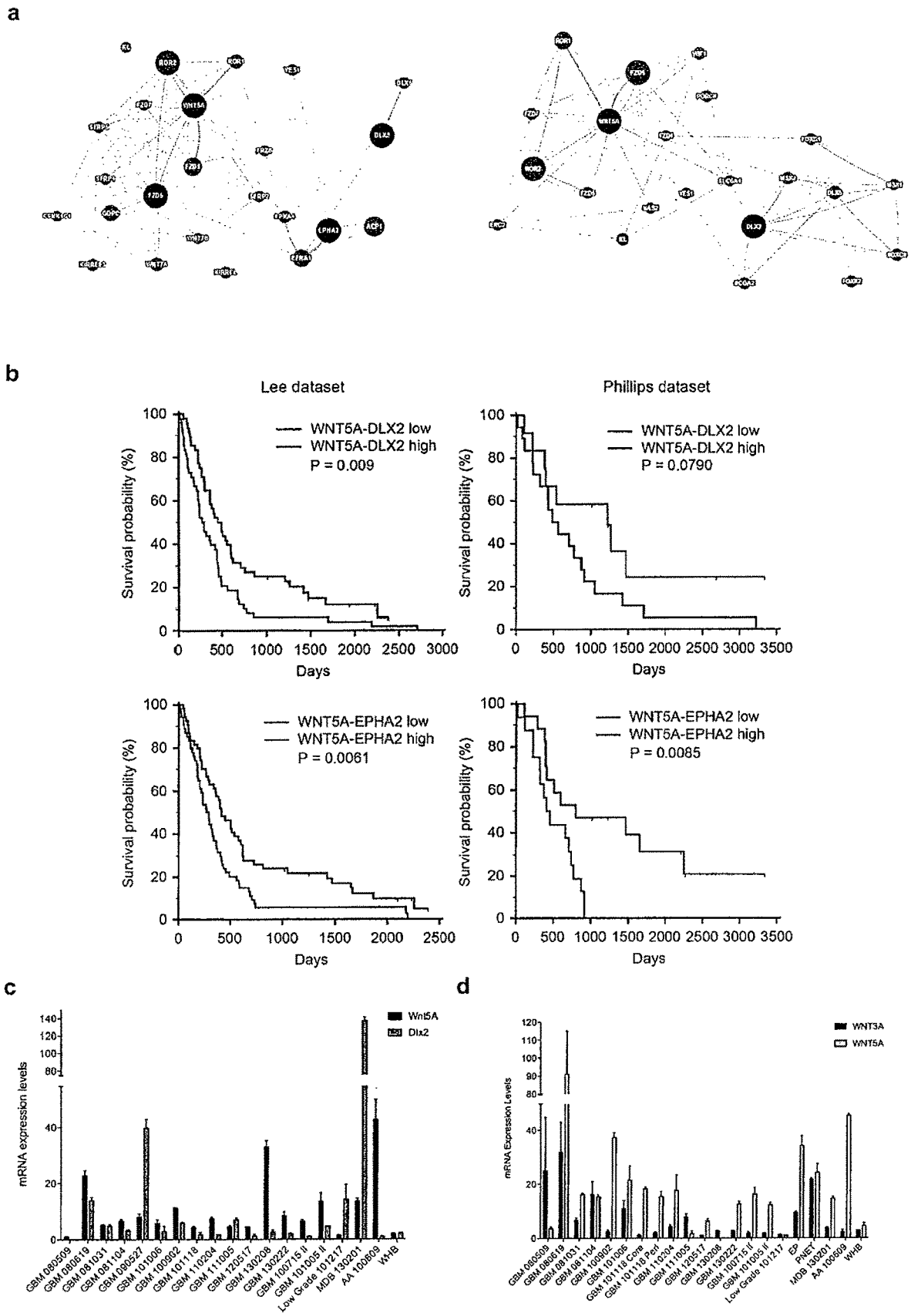
FIG. 13 shows Wnt5a, EphA2 and DlX2 correlation in human GBM tissues and survival of glioma patients.

FIG. 13 shows correlation of Wnt5a, EphA2 and DlX2 expression in human GBM tissues to survival of glioma patients. The TOGA data set highlighted a strong tendency toward mutual exclusion between Wnt5a and EphA2 or Wnt5a and Dlx2 genes (data not shown). As demonstrated in FIG. 13a, protein interaction network analysis of Wnt5a, EphA2 and Dlx2 signature showed that Wnt5a is linked with EphA2 through YES1, a non-receptor protein tyrosine kinase that is involved in the regulation of cell growth and survival, apoptosis, cell-cell adhesion, cytoskeleton remodeling and differentiation. In addition, the protein interaction network analysis showed that Wnt5a is linked to Dlx2 through SLC6A1, a GABA transporter that mediates its rapid removal and maintains low extracellular levels. Kaplan-Meier plots of patients from the Lee and Philips data sets showed significantly decreased survival of glioma patients with a high Wnt5a-Dlx2 or Wnt5a-EphA2 expression (FIG. 13b). FIG. 13c shows quantification of Wnt5a and Dlx2 mRNA levels by qPCR in primary hGBM, low grade glioma, anaplastic astrocytoma and medulloblastoma compared to whole human normal brain (WHB). FIG. 13d shows quantification of non-canonical Wnt5a versus canonical Wnt3a (known to inhibit Wnt5a expression) mRNA levels in the same primary samples and in other types of brain tissues (ependymomas; Ep, and primitive neuroectodermal tumors; PNET).

Figure 14:
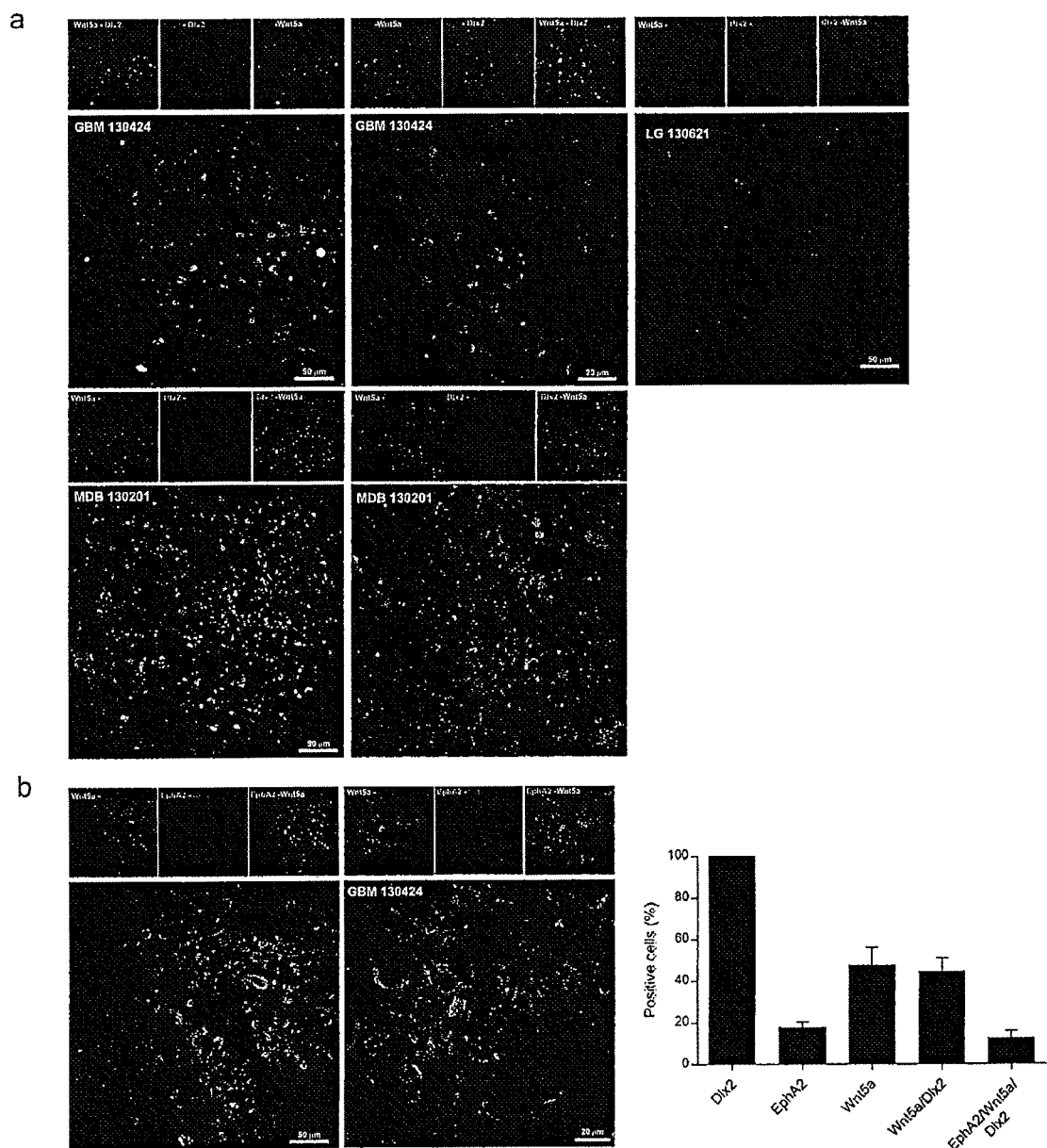
FIG. 14 shows co-expression of Wnt5a and the putative marker of transit-amplifying C cells and neuroblasts Dlx2 in hGBM and MDB versus low grade primary specimens.

FIG. 14a shows co-expression of Wnt5a and Dlx2, the putative marker of transit-amplifying C cells and neuroblasts, in hGBM and MDB versus low grade primary specimens (LG) (Scale bars, 20 and 50 µm). Confocal images at various magnifications show a widespread co-localization of Wnt5a and Dlx2 and a weaker co-expression of Wnt5a, Dlx2 and EphA2 on the surface of cells in hGBM tissue (FIG. 14b).

Figure 15:
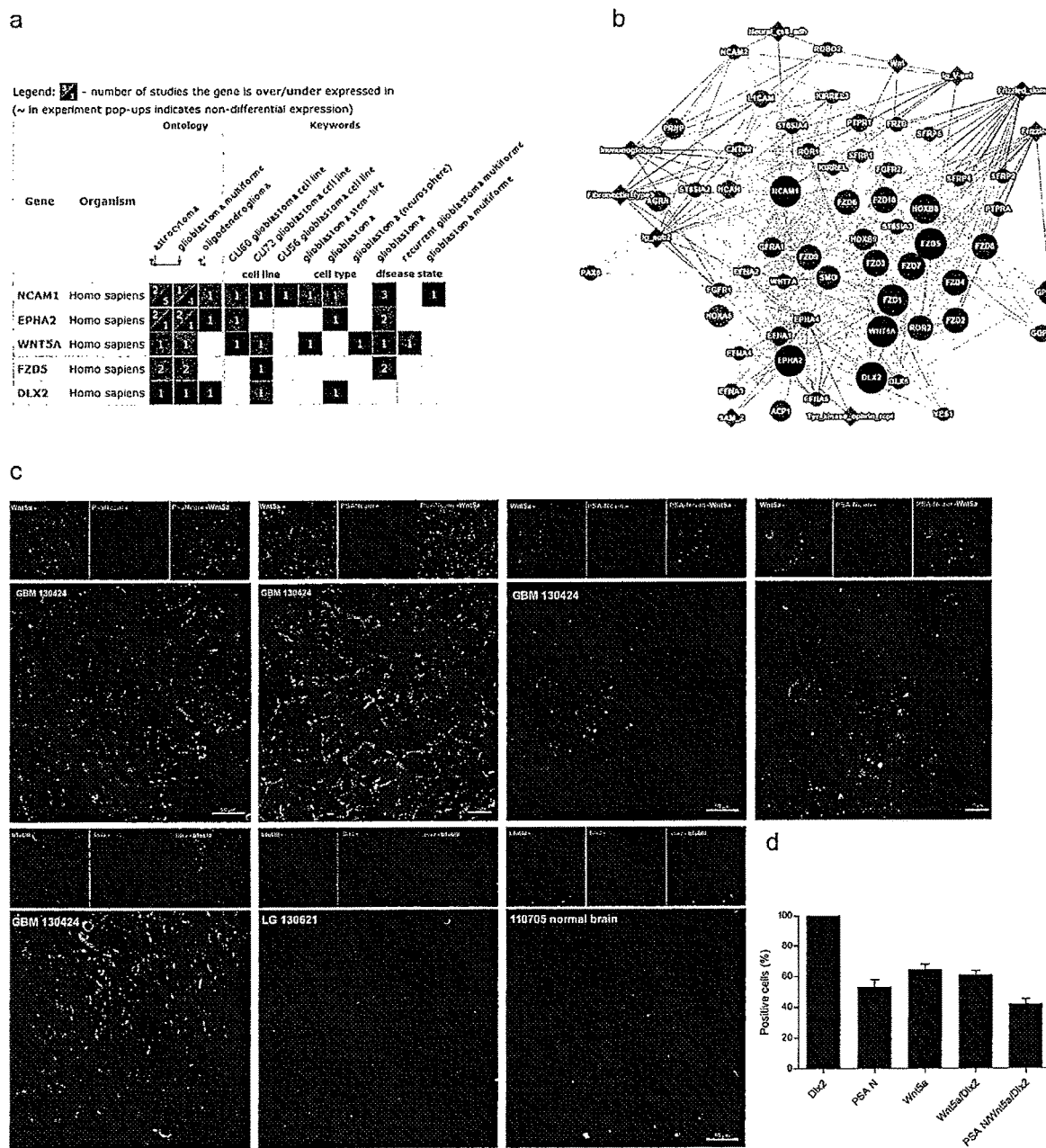
FIG. 15 shows Wnt5A, EPHA2, DLX2 and Neural Cell Adhesion Molecule 1 (NCAM1) gene expression in human brain tumors throughout the malignancy scale.

FIG. 15 shows Wnt5A, EPHA2, DLX2 and Neural Cell Adhesion Molecule 1 (NCAM1) gene expression in human brain tumors throughout the malignancy scale. FIG. 15a shows WNT5A, EPHA2, DLX2 and NCAM1 gene expression from the Gene Expression Atlas (TOGA) in human brain tumors throughout the malignancy scale (i.e. low-grade gliomas (astrocytoma, oligodendroglioma; WHO Grade I and II) and hGBM (Grade IV)) and in human glioblastoma cell lines. FIG. 15b shows protein interaction network analysis of Wnt5a, EphA2, Dlx2 and NCAM1 signatures. In the upper panels of FIG. 15c, immunolabeling of hGBM tissue (130424) at various magnifications shows that a high number of cells positive for Wnt5a ligand co-express the putative neuroblast marker PSA-NCAM with up to 60% of Wnt5a and Dlx2 positive cells immunoreactive for PSA-NCAM (Scale bars, 20 and 50 μm). In the lower panels of FIG. 15c, confocal images of the same hGBM tissue shown in the upper panels of FIG. 15c show the co-expression of Dlx2 and the marker of neural progenitor ☐Tubulin III on the surface of cells in the hGBM tissue compared to infrequent labeling in the primary low grade (LG) and normal brain tissues (Scale bars, 20 and 50 μm). Percentage of positive cells is shown in FIG. 15d. Each bar indicates the mean±SEM.

Without being bound by theory, the correlation of Wnt5a, EphA2 and DLX2 expression in hGBM tissues suggests the presence of over-expressing Wnt5a cell types subventricular zone (SVZ) astrocyte, Type B: Glial fibrillary acidic protein (GFAP+); transient amplifying progenitor, Type C: GFAP−, Dlx2+, PSA-NCAM− and neuroblast, Type A: GFAP−, Dlx2+, PSA-NCAM$^+$ in this tissue type.

Example 5

Expression and/or Activity Modulation of Wnt5a Affects Migration of hGBM TPCs and U87MG Cells In this study, the effect of Wnt5a on tumor development, migration and invasiveness were determined in vitro and in vivo using recombinant Wnt5a protein and lentiviral-mediated over-expression of Wnt5a protein.

Figure 16:
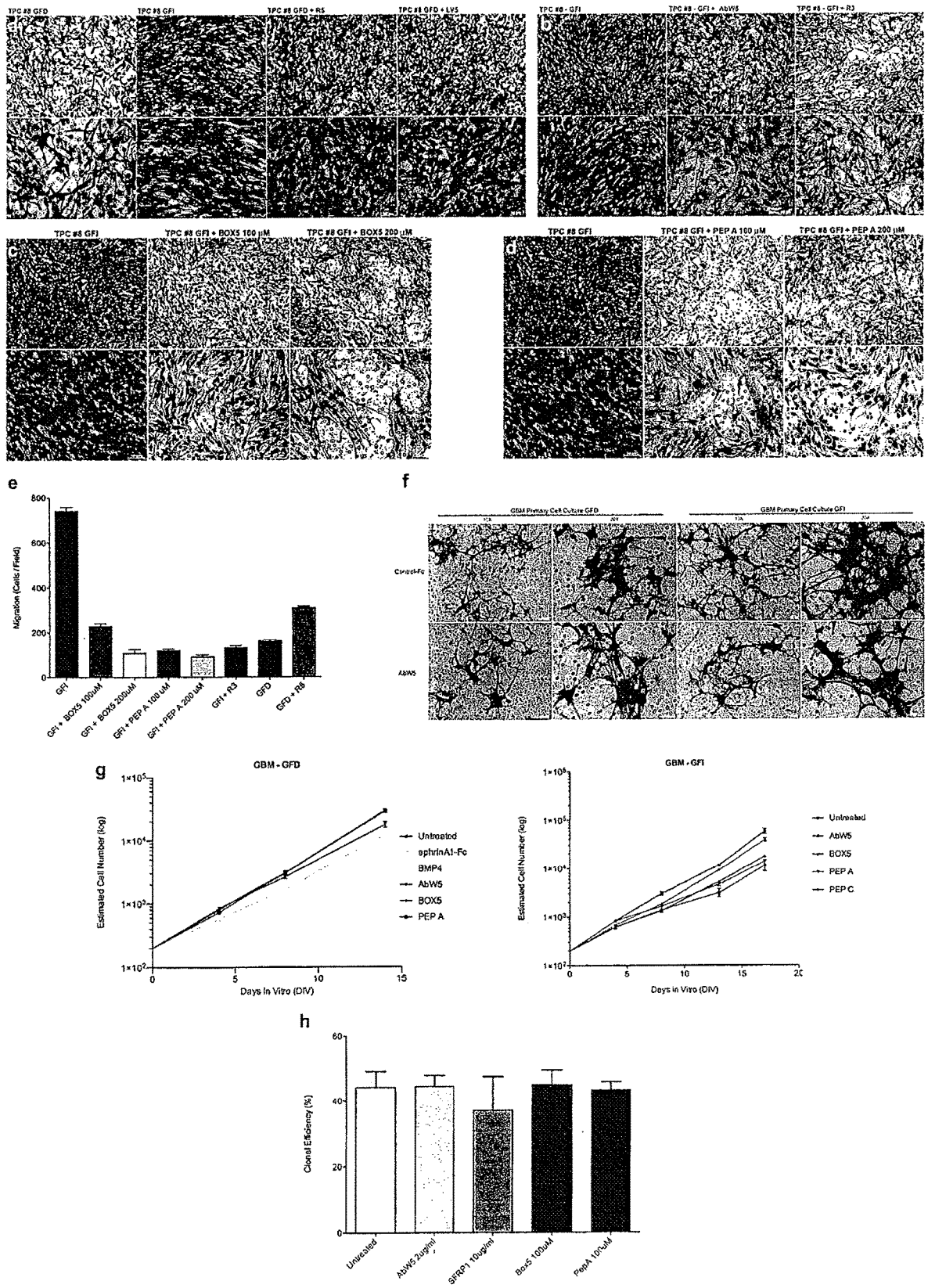
FIG. 16 shows the in-vitro migration and invasion assay of the Wnt5a overexpressing GFI TPCs versus the pre-established GFD counterpart.

FIG. 16 shows the in vitro migration and invasion of the Wnt5a overexpressing GFI TPCs versus the pre-established GFD counterpart. Matrigel invasion assays show that Wnt5a overexpressing GFI TPCs migrate and invade in vitro more efficiently than their pre-established GFD counterpart. Enhanced Wnt5a expression achieved by treating GFD cells with saturating concentrations of recombinant Wnt5a protein (GFD+R5) and by lentiviral-mediated over-expression (GFD+LV5), is paralleled by an increase in cell migration (FIG. 16a). The administration of a Wnt5a-blocking antibody (AbW5; R&D Systems), saturating concentrations of recombinant Wnt3a protein (R3; R&D System) or recombinant secreted frizzled-related protein 1 (R&D System; SFRP1) (an endogenous Wnt antagonist) decreased the invasiveness of GFI TPCs (FIG. 16b). GFI TPCs exposed to Wnt5a-derived peptides Box5, PEPA and PEPB also decreased the invasiveness of GFI TPCs in a dose-dependent fashion (FIGS. 16c and 16d). FIG. 16e shows the quantification of the rate of invasion through matrigel-coated transwell device (Histogram, mean+SEM). Upon exposure to AbW5, GFI cells isolated from primary-patient tumor tissue migrate less efficiently than GFDs (FIG. 16f). FIG. 16g shows that perturbation of Wnt5a activity with AbW5, Box5 and PEPA had negligible effects on the ability of GFI or GFD TPCs to expand as indirectly measured from the slope of the curves. The positive controls bone morphogenetic protein 4 (BMP4) and ephrinA1-Fc significantly triggered negative deviations from the growth kinetics (Figure (Galli et al., Cancer Res. 2004, 65:7011-7021). 16g). Wnt5a inhibition also had negligible effects on TPCs clonal efficiency (i.e., self-renewal ability) (FIG. 16h).

Figure 17:
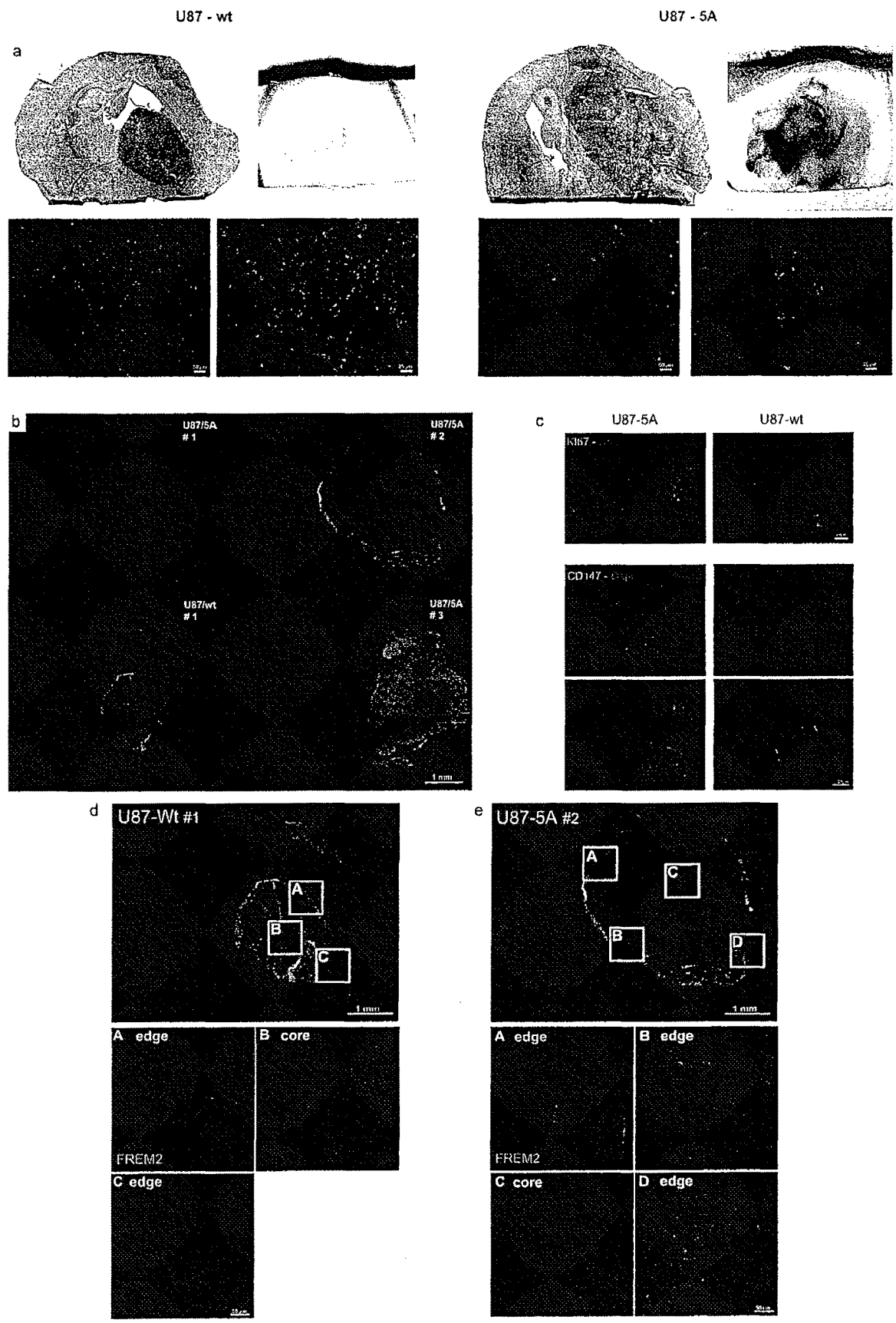
FIG. 17 shows a significantly enhanced tumor development and invasiveness by lentiviral-mediated Wnt5a over-expressing U87MG cells (U87-5A) compared with control cells (U87-wt).

FIG. 17 shows significantly enhanced tumor development and invasiveness by lentiviral-mediated Wnt5a overexpressing U87MG cells (U87-5A) compared with control cells (U87-wt). A representative brain section counterstained with hematoxylin and eosin (H&E) showed significantly enhanced tumor development and invasiveness by lentiviral-mediated Wnt5a overexpressing U87MG cells (U87-5A) as compared to U87-wt control cells (FIG. 17a). The same brain section showed widespread and homogeneous immunoreactivity for human leukocyte marker (HLA) in wild-type (U87-wt) versus Wnt5a-expressing U87MG xenografts (FIG. 17a) (scale bars, 25 and 50 μm). FIG. 17b shows serial histological reconstruction of mouse brain sections immunolabeled with green fluorescent protein (GFP). Transgenic U87MG cells (U87/5A) xenografted intracranially generated tumors with an enhanced capacity for migration, spreading and invasion compared to wt U87-derived tumors, which are quite large in size but do not exhibit any migratory capacity. These wt U87-derived tumors consisted of a progressively enlarging, well-defined mass confined to the site of injection (FIG. 17b). FIG. 17c shows a direct comparison of KI67 (a marker of mitotic index) and CD147 immunoreactivity of wild-type versus Wnt5a expressing-U87MG cells. Wnt5a over-expression significantly enhanced either intracranial proliferation or neo-angiogenesis both locally and distally (scale bars, 20 and 50 μm). FIGS. 17d and 17e show immunolabeling of xenografted tumors. Wild-type U87 sections displayed infrequent and weaker labeling for the putative marker of invasiveness, FRAS1-related extracellular matrix protein 2 (Frem2), as compared to a strong and frequent immunoreactivity in the U87-Wnt5a derived tumors, both in the core and at the tumor edge (scale bars, 50 μm).

Example 6

Wnt5a Perturbation Affects TPCs Tumorigenic Ability and Invasiveness In Vivo

In this study, GFD and GFI TPCs were implanted in immunodeprived adult SCID mice in order to determine the effect of Wnt5a on tumor growth and invasiveness, and on overall survival.

Figure 18:
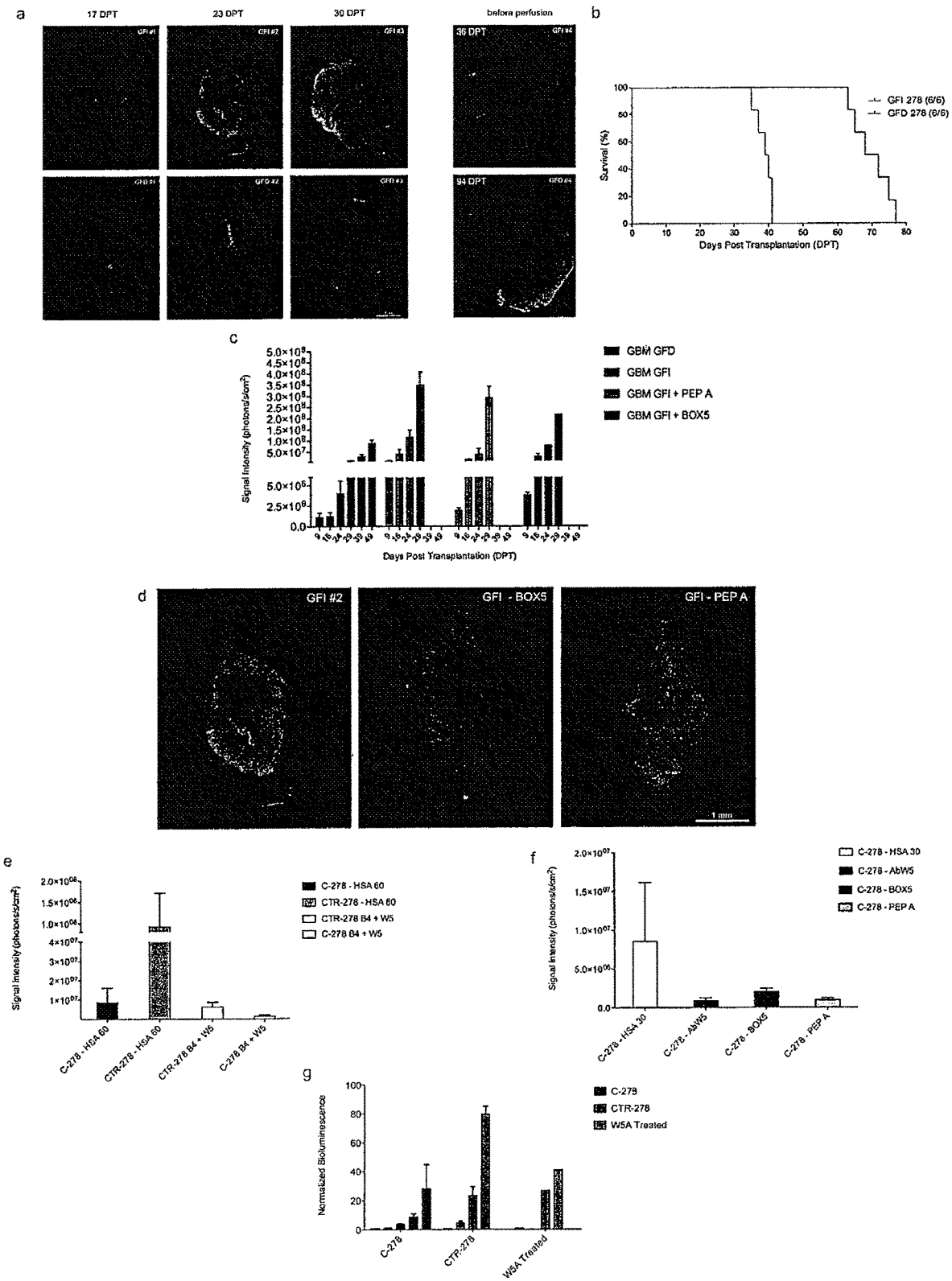
FIG. 18 shows that Wnt5a perturbation affects hGBM tumor-propagating cells with stem-like characteristic (TPCs) tumorigenic ability and invasiveness in vivo.
Figure 19:
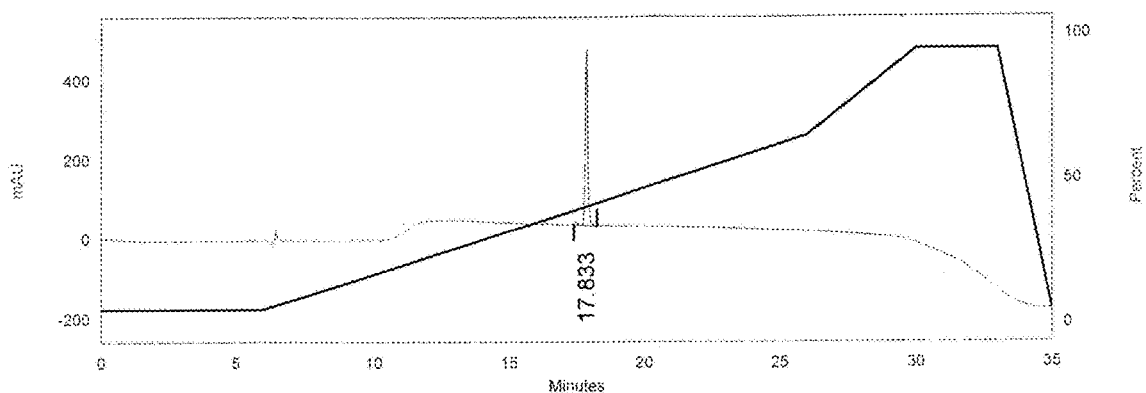
FIG. 19 shows a HPLC chromatogram of Peptide A.
Figure 20:
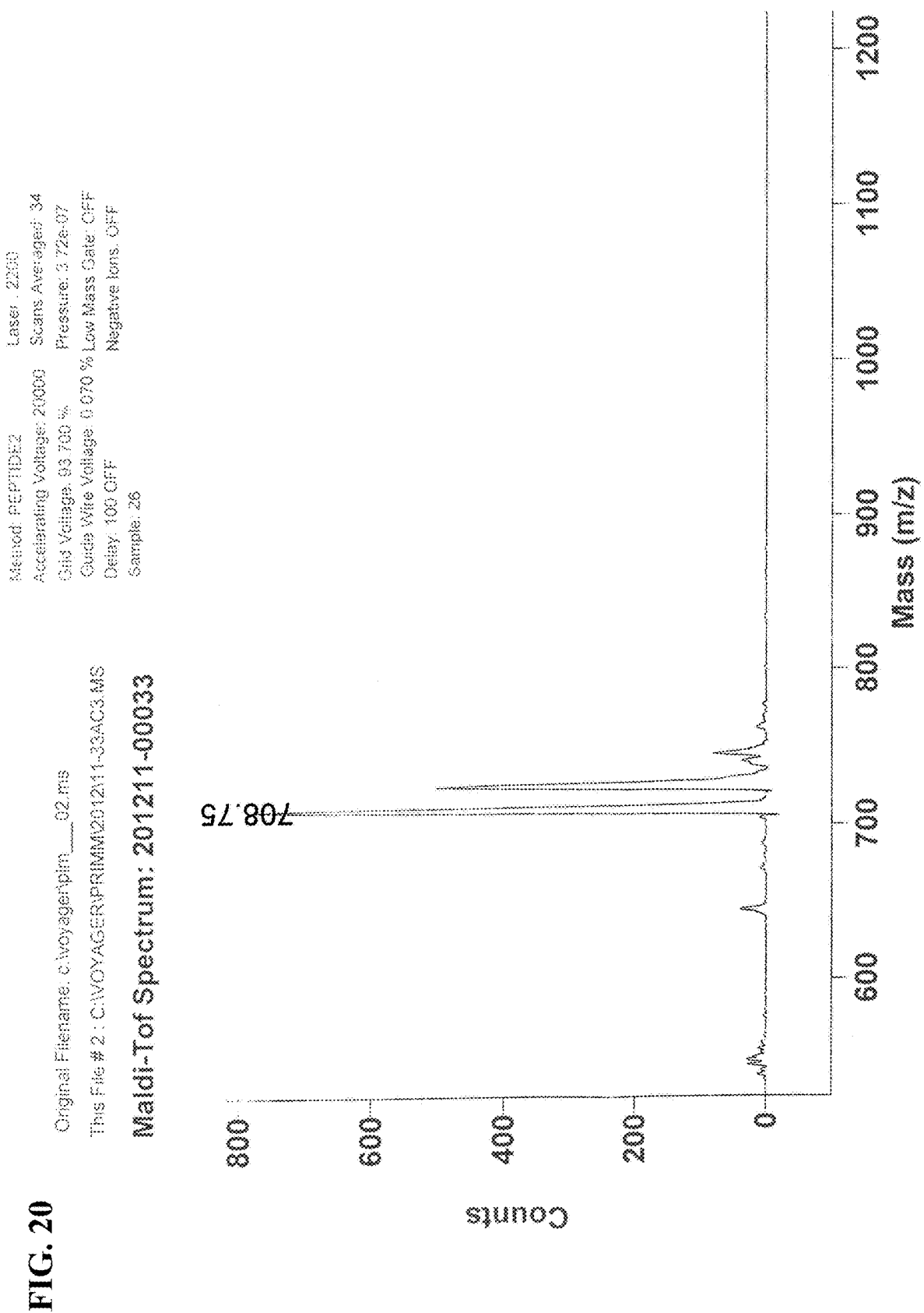
FIG. 20 shows a Maldi-Tof spectrum of Peptide A.
Figure 21:
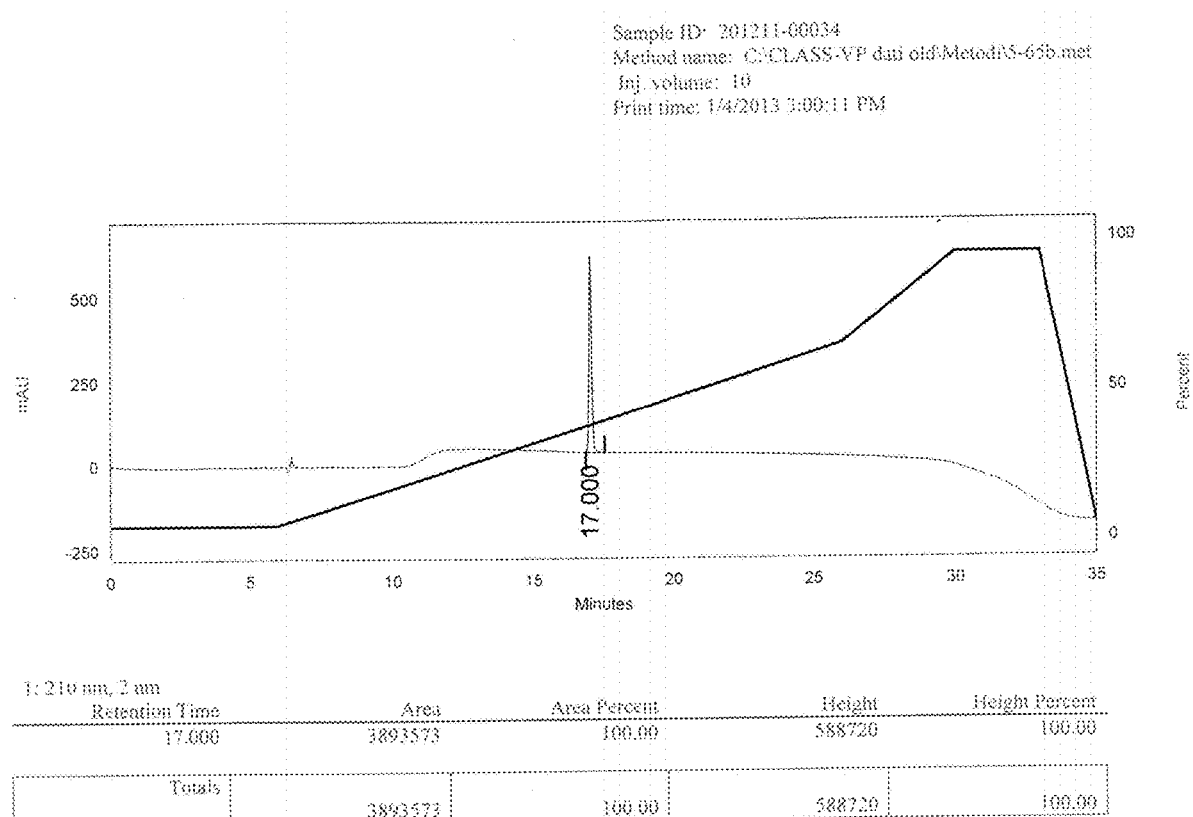
FIG. 21 shows a HPLC chromatogram of Peptide B.
Figure 22:
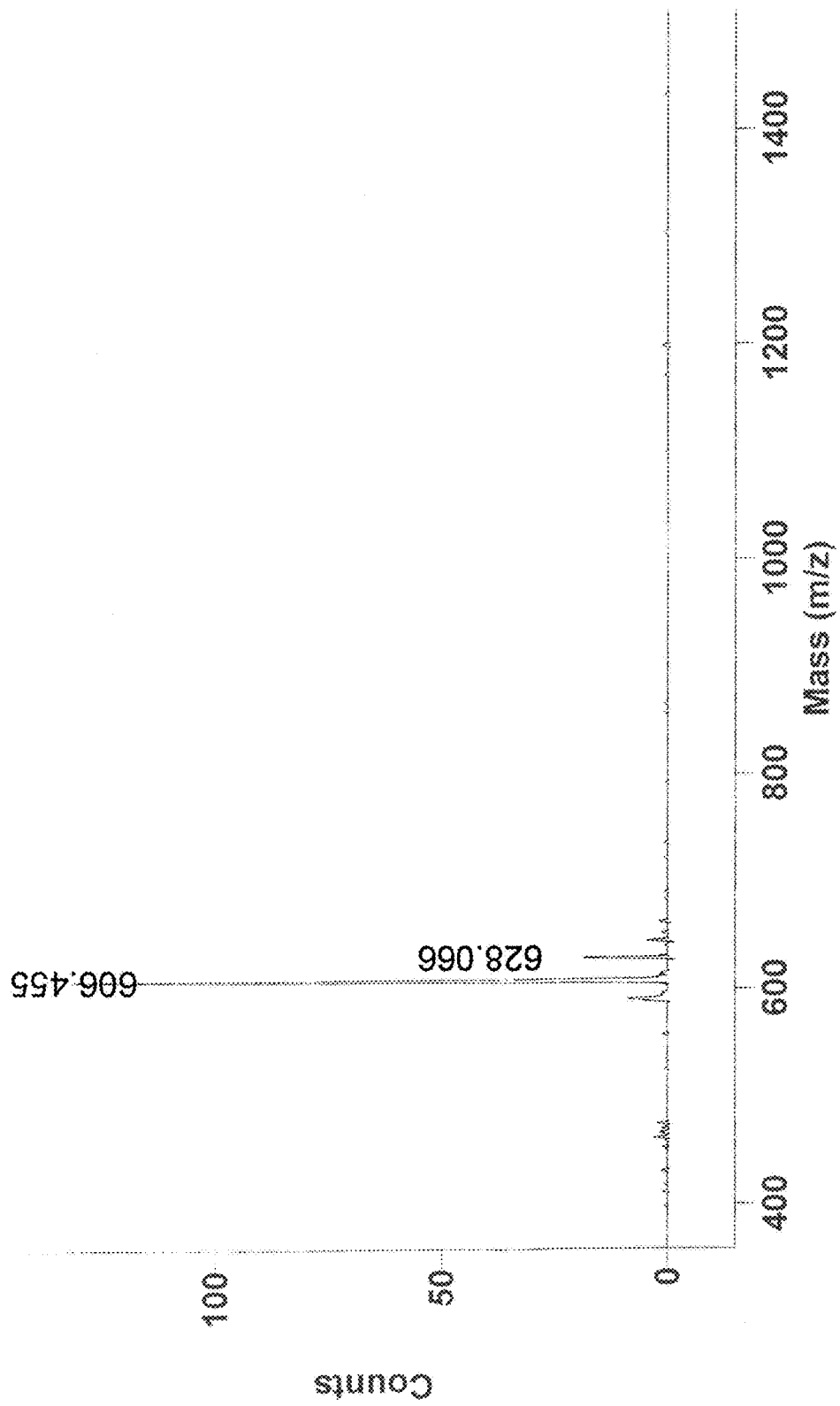
FIG. 22 shows a Maldi-Tof spectrum of Peptide B.

FIG. 18 shows that Wnt5a perturbation affects TPCs tumorigenic ability and invasiveness in vivo. Serial histological reconstruction of mouse brain sections immunolabeled for luciferase showed that, upon orthotopic transplantation into immunodeprived adult SCID mice, tumors generated from the implant of GFI TPCs were more extended and were able to infiltrate the brain parenchyma more efficiently than those generated by their GFD counterpart cells at different times post transplantation (DPT; days post transplantation) (FIG. 18a) (scale bar, 1 mm). Measurements of the rostro-caudal extension of GFD and GFI TPC-derived tumors, as early as 40 days post-transplantation, showed that tumors grown from GFI cells were more expanded than those from their GFD counterpart (data not shown). Kaplan-Meier plot of survival of animals transplanted with GFI-GFD TPCs showed that the enhanced tumorigenic capacity of GFI cells also is reflected in terms of overall survival (FIG. 18b). FIG. 18c shows quantitative time-course analysis of luciferase-tagged TPCs (luc-TPCs). By treating GFI cells with Box5 (SEQ ID NO: 1) and Peptide A (SEQ ID NO: 2) in culture prior to transplantation (pre-treatment), tumor growth is decreased (FIG. 18c) (Histogram, mean±SEM). Mouse brain sections immunolabeled for luciferase confirmed that tumors established from luc- GFI pre-treated with Box5 and PEPA spread through the brain parenchyma less than those established from untreated GFI TPCs (FIG. 18d) (scale bar, 1 mm). Quantitative time-course analysis of luc-TPC signals showed that co-injection (i.e., co-treatment) of either GFD or GFI TPCs with AbW5, alone or in combination with BMP4 (B4), inhibited Box5 and PepA tumor growth (FIGS. 18e and 18f) (Histogram, mean±SEM). Similar results were obtained by injecting AbW5 around the tumor by means of mini-osmotic pumps starting 10 days after GFI TPC transplantation (post-treatment). (FIG. 18g) (each bar indicates mean±SEM).

While the described invention has been described with reference to the specific embodiments thereof, it should be understood by those skilled in the art that various changes may be made and equivalents may be substituted without departing from the true spirit and scope of the Invention. In addition, many modifications may be made to adapt a particular situation, material, composition of matter, process, process step or steps, to the objective, spirit and scope of the described invention. All such modifications are intended to be within the scope of the claims appended hereto.

or amino acid sequence LEGDM (SEQ ID NO: 3), or a combination of peptide derivatives comprising LECGDM (SEQ ID NO: 2) and LEGDM (SEQ ID NO: 3), and wherein the peptide derivative is formulated per se or in salt form.

2. The method according to claim 1, wherein the solid tumor is selected from the group consisting of a brain tumor, a colon tumor, a prostate tumor, a breast tumor, a lung tumor, a skin tumor, a liver tumor, a bone tumor, an ovary tumor, a pancreas tumor, a head tumor, a neck tumor, a nerve tumor and a lymphoma.

3. The method according to claim 2, wherein the solid tumor is a brain tumor, and wherein the brain tumor is a glioma.

4. The method according to claim 3, wherein the glioma is a glioblastoma multiforme.

5. The method according to claim 1, wherein the peptide derivative is synthetic.

6. The method according to claim 1, wherein the peptide derivative is a hexapeptide consisting of amino sequence LECGDM (SEQ ID NO: 2).

7. The method of claim 6, wherein the hexapeptide is a t-butyloxycarbonyl peptide derivative.

The invention claimed is:

1. A method for treating a solid tumor comprising a population of tumor-propagating cells with stem-like characteristics (TPCs) in a subject, comprising administering to the subject a pharmaceutical composition comprising a peptide derivative of Wnt5a, wherein the peptide derivative comprises amino acid sequence LECGDM (SEQ ID NO: 2), 8. The method according to claim 1, wherein the peptide derivative is a pentapeptide consisting of amino acid sequence LEGDM (SEQ ID NO: 3).

9. The method of claim 8, wherein the pentapeptide is a t-butyloxycarbonyl peptide derivative.

10. The method according to claim 1, further comprising the step of administering a second therapeutic agent.

11. The method according to claim 10, wherein the second therapeutic agent is a chemotherapeutic agent.

12. The method according to claim 10, wherein the second therapeutic agent is a Wnt5a antagonist.

13. The method according to claim 1, wherein the pharmaceutical composition is administered to the subject orally, buccally, parenterally, intranasally, rectally, or topically.

14. The method according to claim 1, wherein the pharmaceutical composition comprises a therapeutic amount of the peptide derivative, and a pharmaceutically acceptable carrier, and wherein the therapeutic amount of the peptide derivative is effective:
  (1) to reduce tumor growth, migration, invasion or a combination thereof relative to a control by affecting a level of expression of Wnt5a; and
  (2) to increase survival of the subject relative to a control.

15. The method of claim 1, wherein the peptide derivative is up to thirty amino acids in length.

16. The method of claim 1, wherein the peptide derivative further includes a chemical modification.

17. The method of claim 1, wherein the peptide derivative is a t-butyloxycarbonyl peptide derivative.

18. The method of claim 1, wherein the pharmaceutical composition comprises the combination of peptide derivatives comprising LECGDM (SEQ ID NO: 2) and LEGDM (SEQ ID NO: 3).

* * * * *